US012636428B2

(12) United States Patent
Yodfat et al.

(10) Patent No.: US 12,636,428 B2
(45) Date of Patent: May 26, 2026

(54) SYSTEMS, APPARATUSES AND METHODS FOR FLUID INFUSION INTO A BODY

(71) Applicant: Triple Jump Israel Ltd., Yokneam Illit (IL)

(72) Inventors: Ofer Yodfat, Modi'in (IL); Guy Shinar, Ramat Gan (IL); Yishai Ben-David, Givaat Ella (IL)

(73) Assignee: TRIPLE JUMP ISRAEL LTD., Yokneam Illit (IL)

( * ) Notice: Subject to any disclaimer, the term of this patent is extended or adjusted under 35 U.S.C. 154(b) by 325 days.

(21) Appl. No.: 17/989,645

(22) Filed: Nov. 17, 2022

(65) Prior Publication Data

US 2023/0256160 A1    Aug. 17, 2023

Related U.S. Application Data

(63) Continuation of application No. 16/789,274, filed on Feb. 12, 2020, now Pat. No. 11,554,209, which is a
(Continued)

(51) Int. Cl.
*A61M 5/142* (2006.01)
*A61M 5/14* (2006.01)
(Continued)

(52) U.S. Cl.
CPC ...... *A61M 5/14244* (2013.01); *A61M 5/1407* (2013.01); *A61M 5/14248* (2013.01);
(Continued)

(58) Field of Classification Search
CPC .......... A61M 5/16831; A61M 5/14248; A61M 5/14244; A61M 2005/16863; A61M 2005/14268
See application file for complete search history.

(56) References Cited

U.S. PATENT DOCUMENTS 4,306,976 A    12/1981   Bazzato
5,092,856 A     3/1992   Johnston
(Continued)

FOREIGN PATENT DOCUMENTS

CN           1471413 A      1/2004
CN           1874809 A     12/2006
(Continued)

OTHER PUBLICATIONS

Extended European Search Report, dated Apr. 26, 2021, for European Application No. 18851689.2, 9 pages.
(Continued)

*Primary Examiner* — James D Ponton
*Assistant Examiner* — Hong-Van N Trinh
(74) *Attorney, Agent, or Firm* — FENWICK & WEST LLP

(57) ABSTRACT

Embodiments of the current disclosure are directed toward systems, devices and methods for diabetes management. In particular, the present disclosure relates to devices and methods for dispensing insulin to a patient. A portable fluid infusion device, comprising a disposable part (DP) and a reusable part (RP) is disclosed. The DP comprises a first reservoir and a second reservoir, the second reservoir less than or equal to the first reservoir in length, while the RP comprises a first compartment configured to receive the first reservoir, a second compartment configured to receive the second reservoir and a gasket for sealing a junction between the second reservoir and the second compartment upon connection of the RP and the DP.

14 Claims, 43 Drawing Sheets

Related U.S. Application Data continuation of application No. 15/526,736, filed as application No. PCT/IL2016/050481 on May 5, 2016, now Pat. No. 10,583,244.

(60) Provisional application No. 62/159,158, filed on May 8, 2015.

(51) Int. Cl.
 A61M 5/168 (2006.01)
 A61M 5/172 (2006.01)

(52) U.S. Cl.
 CPC ...... *A61M 5/16831* (2013.01); *A61M 5/1723* (2013.01); *A61M 2005/14268* (2013.01); *A61M 2005/14284* (2013.01); *A61M 2005/16863* (2013.01); *A61M 2205/18* (2013.01); *A61M 2205/33* (2013.01); *A61M 2205/3584* (2013.01); *A61M 2205/50* (2013.01); *A61M 2205/8206* (2013.01); *A61M 2230/201* (2013.01)

(56) References Cited

U.S. PATENT DOCUMENTS

| | | | |
|---|---|---|---|
| 5,135,485 A | 8/1992 | Cohen et al. | |
| 5,803,712 A | 9/1998 | Davis et al. | |
| 6,485,461 B1 | 11/2002 | Mason et al. | |
| 6,558,346 B1* | 5/2003 | Yoshioka | A61M 5/1483 604/141 |
| 8,262,617 B2 | 9/2012 | Aeschlimann et al. | |
| 8,277,415 B2 | 10/2012 | Mounce et al. | |
| 8,529,513 B2 | 9/2013 | Peter et al. | |
| 8,573,027 B2 | 11/2013 | Rosinko et al. | |
| 9,227,010 B2 | 1/2016 | Neta et al. | |
| 9,250,106 B2 | 2/2016 | Rosinko et al. | |
| 9,314,564 B2 | 4/2016 | Imhof et al. | |
| 9,364,185 B2 | 6/2016 | Strickland | |
| 9,415,158 B2 | 8/2016 | Miller et al. | |
| 9,750,873 B2 | 9/2017 | Brown et al. | |
| 9,798,859 B2 | 10/2017 | Yodfat et al. | |
| 9,942,091 B2 | 4/2018 | Harvey et al. | |
| 10,010,674 B2 | 7/2018 | Rosinko et al. | |
| 10,434,254 B2 | 10/2019 | Imhof et al. | |
| 10,438,696 B2 | 10/2019 | Shapley et al. | |
| 10,583,244 B2 | 3/2020 | Yodfat et al. | |
| 10,811,129 B2 | 10/2020 | Bush et al. | |
| 11,241,534 B2 | 2/2022 | Miller et al. | |
| 11,554,209 B2 | 1/2023 | Yodfat et al. | |
| 11,596,733 B2 | 3/2023 | Yodfat et al. | |
| 12,168,113 B2 | 12/2024 | Yodfat et al. | |
| 12,214,156 B2 | 2/2025 | Ben-David et al. | |
| 2005/0101912 A1 | 5/2005 | Faust et al. | |
| 2007/0088271 A1 | 4/2007 | Richards | |
| 2008/0255516 A1 | 10/2008 | Yodfat et al. | |
| 2009/0088694 A1 | 4/2009 | Carter et al. | |
| 2009/0099521 A1 | 4/2009 | Gravesen et al. | |
| 2009/0287180 A1 | 11/2009 | Diperna | |
| 2010/0008795 A1 | 1/2010 | Diperna | |
| 2010/0145303 A1 | 6/2010 | Yodfat et al. | |
| 2010/0262078 A1* | 10/2010 | Blomquist | A61M 5/16831 73/40 |
| 2011/0054399 A1 | 3/2011 | Chong et al. | |
| 2011/0137255 A1 | 6/2011 | Nielsen et al. | |
| 2011/0160654 A1* | 6/2011 | Hanson | A61M 5/1684 340/603 |
| 2011/0196308 A1 | 8/2011 | Kodgule et al. | |
| 2012/0022453 A1 | 1/2012 | Yodfat et al. | |
| 2012/0192951 A1 | 8/2012 | Yodfat et al. | |
| 2013/0012917 A1 | 1/2013 | Miller et al. | |
| 2013/0123743 A1* | 5/2013 | Adams | A61M 5/16831 604/151 |
| 2013/0237955 A1 | 9/2013 | Neta et al. | |
| 2013/0345658 A1* | 12/2013 | Browne | A61M 5/14232 604/67 |
| 2014/0039392 A1 | 2/2014 | Geipel et al. | |
| 2014/0135699 A1 | 5/2014 | Gyory | |
| 2015/0029816 A1 | 1/2015 | Beyer et al. | |
| 2015/0038906 A1 | 2/2015 | Cane' | |
| 2015/0157788 A1 | 6/2015 | Gescheit et al. | |
| 2015/0265765 A1 | 9/2015 | Yavorsky et al. | |
| 2015/0265768 A1 | 9/2015 | Vazquez et al. | |
| 2016/0296695 A1 | 10/2016 | Michael et al. | |
| 2017/0189270 A1 | 7/2017 | David et al. | |
| 2017/0246379 A1 | 8/2017 | Kruse | |
| 2019/0015582 A1 | 1/2019 | Naftalovitz et al. | |
| 2019/0099551 A1 | 4/2019 | Yodfat et al. | |
| 2019/0160258 A1 | 5/2019 | Kristen | |
| 2019/0321544 A1 | 10/2019 | List | |
| 2020/0013495 A1 | 1/2020 | Torai | |
| 2020/0179594 A1 | 6/2020 | Yodfat et al. | |
| 2020/0206417 A1 | 7/2020 | Yodfat et al. | |
| 2020/0345929 A1 | 11/2020 | Ben-David et al. | |
| 2024/0001028 A1 | 1/2024 | Yodfat et al. | |

FOREIGN PATENT DOCUMENTS

| | | |
|---|---|---|
| CN | 101563120 A | 10/2009 |
| CN | 101772359 A | 7/2010 |
| CN | 101808679 A | 8/2010 |
| CN | 102186515 A | 9/2011 |
| CN | 102596289 A | 7/2012 |
| CN | 102813976 A | 12/2012 |
| CN | 102985124 A | 3/2013 |
| CN | 103370007 A | 10/2013 |
| CN | 103442749 A | 12/2013 |
| CN | 203647799 U | 6/2014 |
| CN | 203815967 U | 9/2014 |
| CN | 104203311 A | 12/2014 |
| CN | 104474606 A | 4/2015 |
| CN | 104717991 A | 6/2015 |
| CN | 106659845 A | 5/2017 |
| DE | 3708857 A1 | 9/1988 |
| EP | 0236543 A1 | 9/1987 |
| EP | 1704886 A1 | 9/2006 |
| EP | 2295093 A2 | 3/2011 |
| EP | 2295098 A1 | 3/2011 |
| EP | 2365453 A2 | 9/2011 |
| EP | 2698178 A2 | 2/2014 |
| EP | 2719410 A2 | 4/2014 |
| EP | 2763064 A2 | 8/2014 |
| EP | 2919831 A1 | 9/2015 |
| EP | 3095255 A1 | 11/2016 |
| EP | 3284507 A1 | 2/2018 |
| EP | 3335745 A1 | 6/2018 |
| JP | S56116470 A | 9/1981 |
| JP | H0388547 U | 9/1991 |
| JP | 2002248168 A | 9/2002 |
| JP | 2006512114 A | 4/2006 |
| JP | 2010-523167 A | 7/2010 |
| JP | 2011-516097 A | 8/2010 |
| JP | 2011-518634 A | 6/2011 |
| JP | 2012513786 A | 6/2012 |
| JP | 2013503691 A | 2/2013 |
| JP | 2013503706 A | 2/2013 |
| JP | 2013544161 A | 12/2013 |
| JP | 2014050686 A | 3/2014 |
| JP | 2014531922 A | 12/2014 |
| WO | WO-2004052725 A1 | 6/2004 |
| WO | WO-2007108987 A2 | 9/2007 |
| WO | WO-2008024808 A2 | 2/2008 |
| WO | WO-2008122983 A1 | 10/2008 |
| WO | WO-2009045779 A2 | 4/2009 |
| WO | WO-2010076275 A1 | 7/2010 |
| WO | WO-2011009224 A2 | 1/2011 |
| WO | WO-2011028846 A2 | 3/2011 |
| WO | WO-2013033421 A2 | 3/2013 |
| WO | WO 2014/004159 A1 | 1/2014 |
| WO | WO-2018/229783 A1 | 4/2016 |
| WO | WO-2016145094 A2 | 9/2016 |
| WO | WO-2016157638 A1 | 10/2016 |

(56) References Cited

FOREIGN PATENT DOCUMENTS

| WO | WO-2016181384 A2 | 11/2016 |
| WO | WO-2017060899 A2 | 4/2017 |
| WO | WO-2019043702 A1 | 3/2019 |

OTHER PUBLICATIONS

Extended European Search Report, dated Jan. 9, 2019, for European Application No. 16792303.6, 6 pages.
Extended European Search Report, dated Sep. 23, 2020, for European Application No. 18818197.8, 7 pages.
Extended European Search Report for European Application No. EP22184226.3 dated Jan. 23, 2023, 8 Pages.
International Preliminary Report on Patentability, dated Dec. 17, 2019, for International Application No. PCT/IL2018/050668, 6 pages.

International Preliminary Report on Patentability, dated Mar. 3, 2020, for International Application No. PCT/IL2018/050952, 7 pages.
International Preliminary Report on Patentability, dated Nov. 14, 2017, for International Application No. PCT/IL2016/050481, 6 pages.
International Search Report and Written Opinion, mailed Dec. 6, 2016, for International Application No. PCT/IL2016/050481, 9 pages.
International Search Report and Written Opinion, mailed Dec. 6, 2018, for International Application No. PCT/IL2018/050952, 9 pages.
International Search Report and Written Opinion, mailed Oct. 4, 2018, for International Application No. PCT/IL2018/050668, 8 pages.
Invitation to pay additional search fees, mailed Sep. 20, 2016, for International Application No. PCT/IL2016/050481, 2 pages.
Office Action in Japanese Patent Application No. 2021-036270 mailed Dec. 27, 2021, and English translation, 7 pages.
N/A.

* cited by examiner

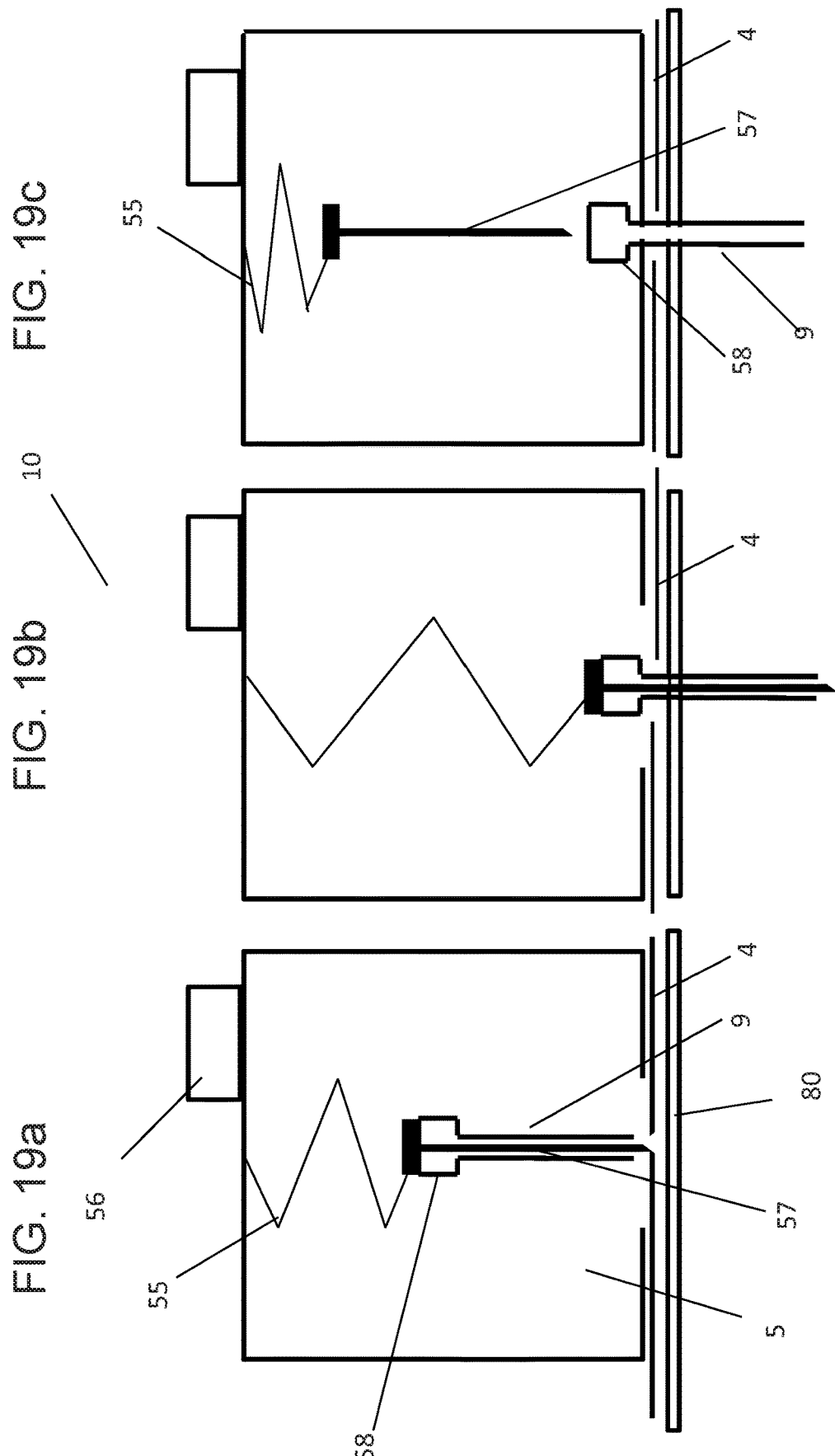

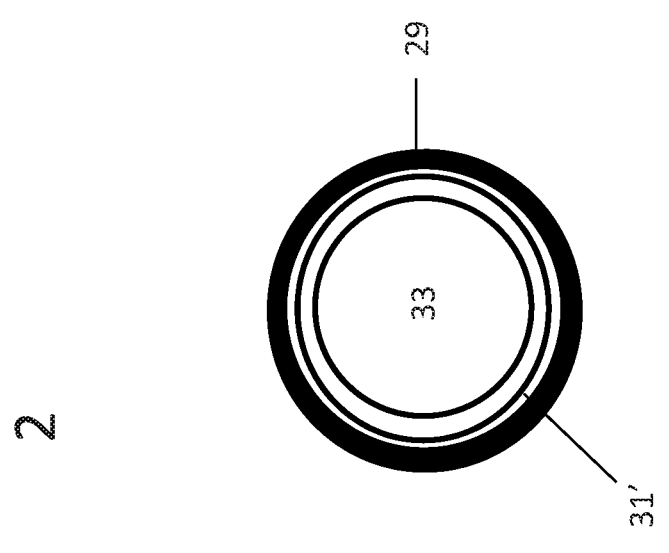
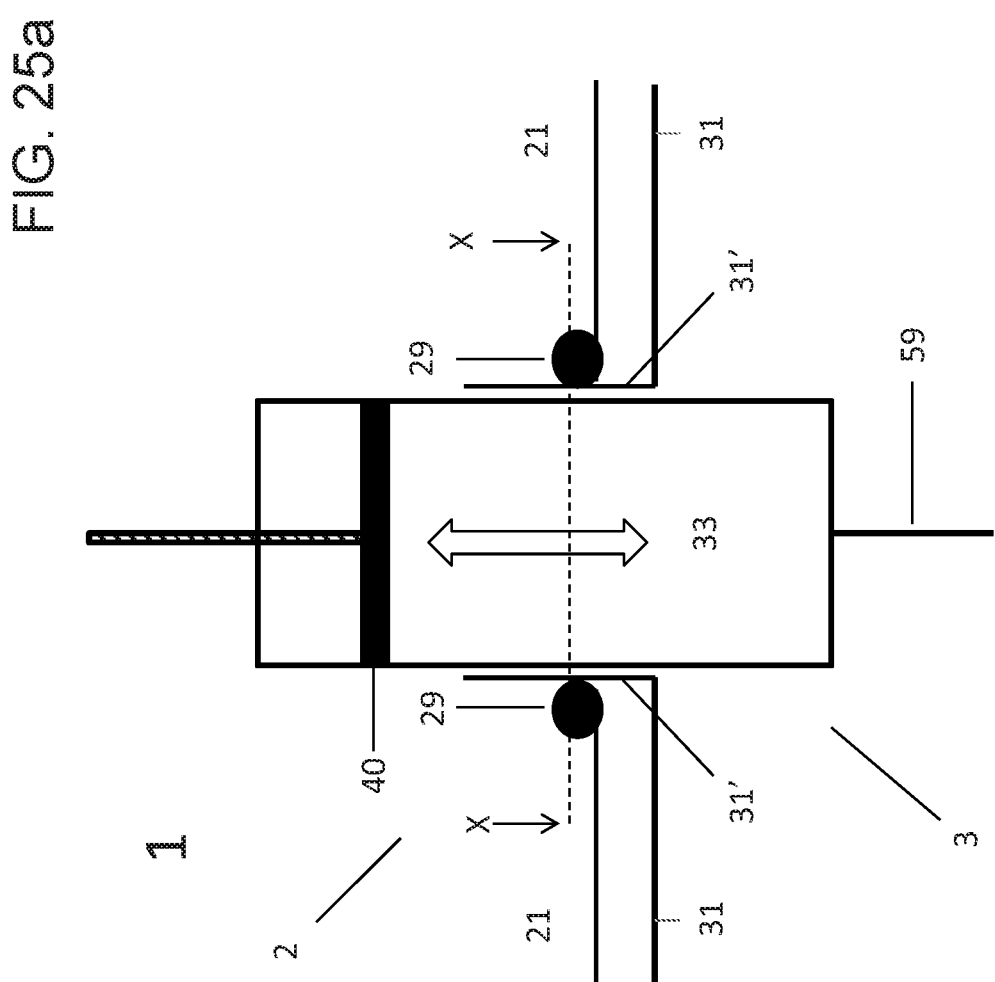
FIG. 25a

SYSTEMS, APPARATUSES AND METHODS FOR FLUID INFUSION INTO A BODY

This application is a continuation of U.S. patent application Ser. No. 16/789,274, filed Feb. 12, 2020, entitled "Systems, Apparatuses and Methods for Fluid Infusion Into A Body", which is a continuation of U.S. patent application Ser. No. 15/526,736 filed May 12, 2017, entitled "Systems, Apparatuses and Methods for Fluid Infusion Into A Body" (U.S. Pat. No. 10,583,244), which is a national stage entry of, and claims priority to, International Patent Application No. PCT/IL2016/050481, filed May 5, 2016, entitled "Systems, Apparatuses and Methods for Fluid Infusion into a Body," which in turn claims priority to U.S. Provisional Patent Application No. 62/159,158, filed May 8, 2015, entitled "Systems, Apparatuses and Methods for Fluid Infusion into a Body." The present application incorporates herein by reference the disclosures of each of the above-referenced applications in their entireties.

FIELD OF THE DISCLOSURE

Embodiments of the current disclosure are directed toward systems, devices and methods for diabetes management. In particular, the present disclosure relates to devices and methods for dispensing insulin to a patient. More particularly, the present disclosure relates to a miniature portable skin securable insulin patch pump.

BACKGROUND OF THE INVENTION

Diabetes mellitus patients require administration of varying amounts of insulin throughout the day to control their blood glucose levels. Ambulatory portable insulin infusion pumps can be used as superior alternatives to multiple daily syringe injections of insulin. However, although these devices represent an improvement over multiple daily injections, they nevertheless all suffer from several drawbacks. One drawback is the large size and weight of the devices, caused by the configuration and the relatively large size of the driving mechanism and syringe. These relatively bulky devices have to be regularly carried in a patient's pocket or attached to his/her belt.

SUMMARY OF SOME OF THE EMBODIMENTS

Embodiments of the present disclosure are directed at a diabetes management system that includes a miniature insulin patch pump. The patch pump may be controlled by any electronic device (a "bridge" device) having an RF communication means such as Bluetooth or Bluetooth Low Energy (BLE). Software that includes patient and pump control parameters may be stored in a remote server and may be downloaded to the bridge device after receiving user authentication. The bridge device may provide two way communication between the patch pump and a remote station such as physician office PC or remote smartphone of a diabetic child parent. The patch pump may be integrated in a diabetes management system that includes a continuous glucose monitor (CGM) and a blood glucose monitor (BGM). An artificial pancreas algorithm on patch pump processor automatically controls insulin delivery according to continuous glucose readings received from a remote CGM ("closed loop system"). The bridge device processor includes bolus calculator software that may calculate and recommend bolus doses. Calculations of bolus doses is done by a bridge processor after receiving blood glucose readings from remote BGM, glucose level trends from remote CGM, and meal carb content from a bridge user interface (i.e. touch screen). The patch pump may continuously deliver insulin according to CGM glucose readings; receive bolus commands from the bridge device at meals, or both. The patch pump may include: 1) a reusable part (RP) that may comprise one or more of a battery, actuation module having a driving rod ("rod") and electronic module, 2) a disposable part (DP) that may comprise one or more of a first reservoir, a second reservoir ("doser"), an exit port, 3) a disposable cradle/cannula/inserter assembly, and 4) a charger. The patch pump may be ready for insulin delivery after filling the reservoir, connecting the RP and the DP, and air purging (priming). After cannula insertion and cradle adhesion to skin, the patch may be connected to cradle and may be disconnected and reconnected at the patient's discretion. When the patch pump is disconnected the reservoir may be refilled and the RP may be replaced by a second RP having a charged battery. The pumping mechanism may comprise a first reservoir having a first plunger, a second reservoir (doser) having a second plunger, a first conduit connecting first and second reservoir, a second conduit connecting second reservoir and an exit port, and the exit port. The second reservoir may be linearly displaced relative to the first reservoir by linear displacement of the second plunger by the actuation module and driving rod. When the second plunger is displaced in one direction, the second reservoir is linearly displaced at the same first direction and fluid is delivered from first reservoir via first conduit to second reservoir. When second plunger is displaced in the opposite direction the second reservoir is displaced in the same opposite direction and fluid is delivered from second the reservoir via second conduit to exit port.

Some of the advantages of the embodiments of the present disclosure include the miniature size of the devices (e.g., conveniently portable), their accuracy and ease of integration. For example, the devices and systems possess the ability to integrate with closed and open loop diabetes management systems. Further, they can be utilized for a much longer duration of use than can be the case with conventional systems. In addition, the present embodiments disclose methods of removing air bubbles from fluids, a feature that distinguishes these features from conventional methods and systems. In some embodiments, a portable device that contains an insulin reservoir in communication with a subcutaneous cannula and a method for continuous (basal) and on-demand (bolus) delivery of insulin is disclosed. Basal and bolus administration rates may contribute to enhanced accuracy for the delivery of insulin. In some embodiments, an ambulatory skin adherable insulin pump (patch pump) that is substantially smaller, less bulky, thinner and lighter than previously known insulin delivery systems is disclosed. Further, the skin adherable patch pump can be concealable. In some embodiments, the device may not have operating buttons and may be remotely controlled. In some embodiments, the patch pump comprises a reusable part and a disposable part. The reusable part can include most or all relatively expensive components including plunger threaded rod, battery, driving mechanism and electronics. Further, the patch pump can be waterproof and allow for pressure equilibrium between surrounding environment and reservoir. In addition, the patch pump can be controlled with a variety of consumer electronic devices that may be used by the patient such as smartphone, smart-watch, tablet, or PC.

In some embodiments, a portable fluid infusion device comprises a first reservoir; a second reservoir including a plunger and a hollow needle, the hollow needle configured to allow flow of fluid into and/or out of the second reservoir; a dual chamber assembly comprising a first chamber compartment and a second chamber compartment; an exit port; a first conduit configured to communicate fluid between the first reservoir and the first chamber compartment of the dual chamber assembly; and a second conduit configured to communicate fluid between the exit port and the second chamber compartment of the dual chamber assembly; wherein a tip or an opening of the hollow needle is configured to transition from the second chamber compartment to the first chamber compartment upon displacement of the second reservoir in a first direction and from the first chamber compartment to the second chamber compartment upon displacement of the second reservoir in a direction opposite to the first direction.

In some embodiments, the first reservoir further comprises a filling port for receiving fluid into the first reservoir. The first reservoir may also be configured as a prefilled replaceable reservoir. In addition, the first reservoir comprises a second plunger configured to transition between two ends of the first reservoir in the first direction and/or in the direction opposite to the first direction, wherein the advancement of the second plunger in the direction opposite to the first direction causes fluid flow from the first reservoir to the second reservoir.

In some embodiments, the portable fluid infusion device further comprises an electronic module and an actuation module for operating the displacement of the plunger in the first and/or opposite to the first directions, wherein the electronics module comprises a power source, a processor, a transceiver, a buzzer, and/or a sensor, and wherein the sensor includes one or more of a motion sensor, a power source level sensor, air bubble sensor, revolution sensor, occlusion sensor, reservoir level sensor, second reservoir motion sensor, second reservoir position sensor, and/or plunger position sensor. Further, the actuation module comprises an actuator and a rod, the rod configured to operably couple to the plunger to drive the displacement of the plunger and/or the second reservoir. The actuation module further comprises a rod coupling means coupled to the rod and a plunger coupling means coupled to the plunger; wherein a connection between the rod coupling means and the plunger coupling means allows the rod to operably couple to the plunger; wherein the connection between the rod coupling means and the plunger coupling means is mechanical and/or magnetic; and wherein distal end of the first reservoir aligns with or extends beyond distal end of the rod upon maximum displacement of the plunger in the first direction.

In some embodiments, the portable fluid infusion device further comprises a first stopper configured to block a proximal end of the second reservoir upon the displacement of the second reservoir in the first direction; and a second stopper configured to block a distal end of the second reservoir upon the displacement of the second reservoir in the direction opposite to the first direction. In some embodiments, the hollow needle is rigidly coupled to the second reservoir. In some embodiments, a displacement of the plunger in the first direction is configured to causes fluid flow from the first reservoir to the first chamber compartment via the first conduit, and displacement of the plunger opposite to the first direction is configured to causes fluid flow from the second reservoir to the exit port via the second conduit, wherein the plunger and the second reservoir are operably coupled so as to cause displacement of the second reservoir in a same direction as direction of displacement of the plunger until one of the first stopper and the second stopper blocks the second reservoir.

In some embodiments, a portable fluid infusion device comprises a disposable part (DP) comprising a first reservoir and a second reservoir, the second reservoir having a length which is less than or equal to the length of the first reservoir; and a reusable part (RP) comprising: a first compartment configured to receive the first reservoir; a second compartment configured to receive the second reservoir; and a gasket for sealing a junction between the second reservoir and the second compartment upon connection of the RP and the DP. Further, the portable fluid infusion device comprises a vent configured to vent the first compartment, wherein the vent comprises an aperture arranged on the device to vent the first compartment. In addition, the vent may be configured to operate upon connection of the RP and the DP. In some embodiments, after connection of the RP and the DP, the second compartment is sealed and the first compartment is vented.

In some embodiments, the RP includes a rigid housing, wherein after connection of the RP and the DP, at least one of the first reservoir and the second reservoir are not in contact with the housing. In some embodiments, after connection of the RP and the DP, the first reservoir and the second reservoir do not contact with the housing. In some embodiments, the portable fluid infusion device further comprises a water resistant member arranged between the RP and the DP and configured to allow air to pass through the member and substantially restrict or prevent the passage of liquid, wherein the first compartment includes a non-round opening for allowing the reception of the first reservoir into the first compartment, and/or the second compartment includes a round opening for allowing the reception of the second reservoir into the second compartment. In some embodiments, maximal height of the second reservoir is about equal to maximal height of the first reservoir. In some embodiments, the first reservoir includes a filling port for receiving fluid into the first reservoir, wherein the filling port comprises an opening punctured from a silicone membrane of a shell of the first reservoir. In some embodiments, the first reservoir is configured as a prefilled replaceable reservoir.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 19A-C show schemes of infusion site interface (e.g., inserter, cradle, and cannula) and insertion mechanism, according to some embodiments.

FIGS. 22A-D show schemes of the priming process, according to some embodiments.

FIGS. 25A and 26A-B show an enlarged scheme of active valve system, according to some embodiments.

FIGS. 27A-F show schemes of pumping mechanism employing the active valve system, according to some embodiments.

FIGS. 29A-C show cross section (A and B) and spatial (C) views of active valve system of FIG. 28, according to some embodiments.

FIGS. 39A-D shows examples of bridge devices, according to some embodiments.

FIG. 40 shows a schematic diagram of server, according to some embodiments.

FIG. 41 shows a schematic diagram of bridge device, according to some embodiments.

DETAILED DESCRIPTION OF SOME OF THE EMBODIMENTS

Figure 1:
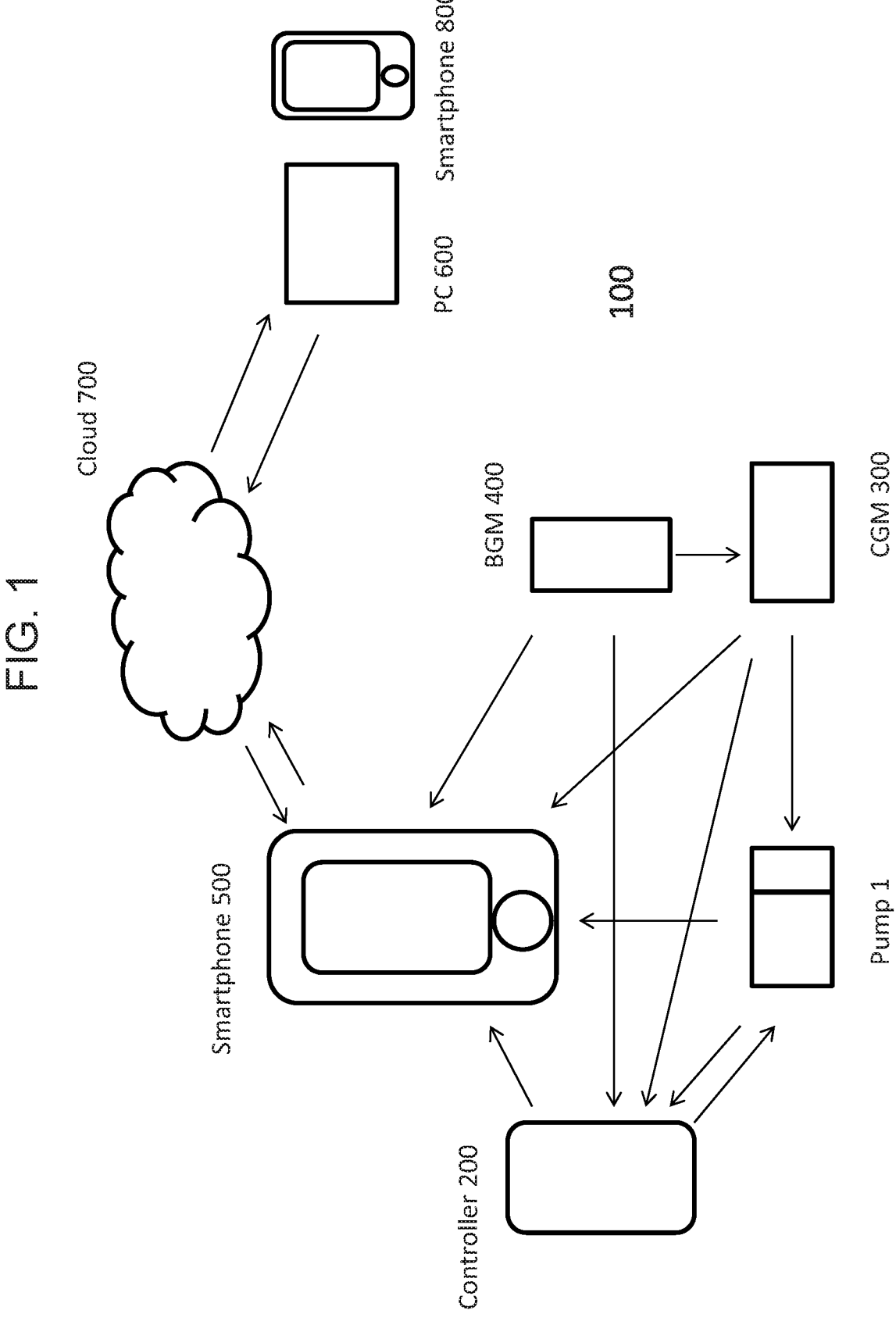
FIG. 1 shows a scheme of a diabetes management system, according to some embodiments.

With reference to FIG. 1, in some embodiments, a scheme of a diabetes management system 100 is shown. The system includes at least one of the following components: insulin pump 1, continuous glucose monitor (CGM) 300, blood glucose monitor (BGM) 400, controller 200, smartphone 500, PC 600, and cloud 700. System 100 components may wirelessly communicate in two way communication (i.e. pump 1-controller 200) or one way communication (i.e. pump 1-smartphone 500). Communication protocols could be, for example, Bluetooth, Bluetooth Low Energy (BLE), or any other proprietary RF protocol. Pump controller 200 may provide an interface for the user with pump 1 for commanding basal and bolus doses and profiles and for receiving alerts and alarms. Communication between CGM 300 and pump 1 may provide artificial pancreas (closed loop system) functionality in which insulin doses are automatically administered according to monitored glucose levels of CGM 300. Transmitted readings from BGM 400 and/or CGM 300 to pump controller 200 and/or smartphone 500 provide the user with glucose readings for calculating insulin dosing. Real time and stored data from pump 1, pump controller 200, CGM 300, and BGM 400 may be transmitted to smartphone 500 to be presented or stored. Two way cellular communication of smartphone 500 with cloud 700 may provide the patient with ability to download personal data stored at a remote server. Data in cloud 700 may be downloaded, processed and transmitted to and from a PC 600 or a remote smartphone 800. Examples: 1) a glucose reading measured with a child BGM 400 is transmitted to mother's smartphone 800 in real time. 2) Physician downloads patient's last month's stored data from cloud 700 to office PC 600 (insulin administrations and glucose readings). Accordingly physician tailors basal profile setting and sends message to patient's smartphone 500.

Figures 2A, 2B:
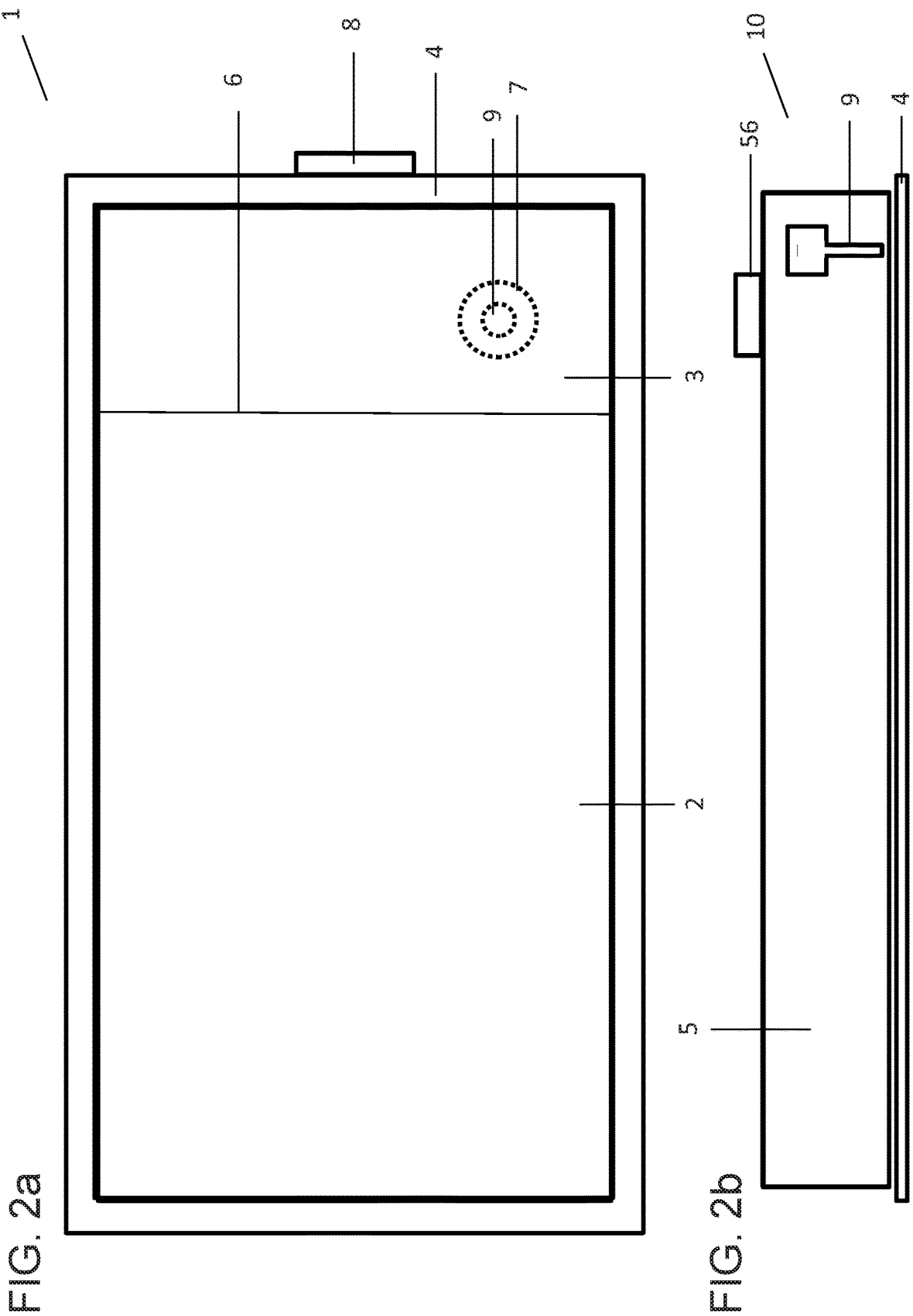
FIGS. 2A-B show schemes of a fluid infusion device and infusion site interface, respectively, according to some embodiments.

With reference to FIGS. 2A-B, in some embodiments, schemes of a fluid infusion device 1 (2a) (hereinafter "device") and infusion site interface 10 (2*b*) are shown. In some embodiments, device 1 may infuse a fluid into the body of a patient via a cannula or a needle which is in direct fluid communication with device 1, without external tubing. The fluid may be a drug such as, for example, a biologic, a hormone, or a chemotherapeutic. The hormone may be insulin, or, for example, glucagon. Device 1 may be configured to deliver a fluid according to a predetermined program. Device 1 may also be a component of a system 100 in which the device 1 is in wireless communication with one or more of system 100 components—BGM, CGM, pump controller, smartphone or any other designated remote transceiver. FIG. 2*a* shows device 1. Device 1 may comprise a reusable part (RP) 2, a disposable part (DP) 3, a cradle 4, and a cannula 9. RP 2 and DP 3 may be reversibly connected to each other to form a functioning fluid infusion pump 6. DP 3 may comprise an exit port 7, through which infusion fluid may exit DP 3 on its way into a patient's body. Pump 6 may be reversibly connected to cradle 4 by, for example, a snap mechanism 8. One side of the cradle (e.g., bottom side) may be connected to a patient's body by means of, for example, an adhesive. FIG. 2*b* shows the infusion site interface 10. Infusion site interface 10 comprises an inserter 5, a cradle 4, and cannula 9. Cradle 4 faces the patient's skin and is opposite inserter 5. When infusion site interface 10 is attached to the patient's skin, cradle 4 adheres to skin by cradle adhesive. Inserter 5 may be used to automatically insert a cannula 9 into the patient's body by pushing button 56. After cannula insertion, inserter 5 is disposed, cradle 4 remains adhered to skin, and cannula 9 transverse exit port 7 and resides in patient's subcutaneous tissue below the skin.

Figure 3:
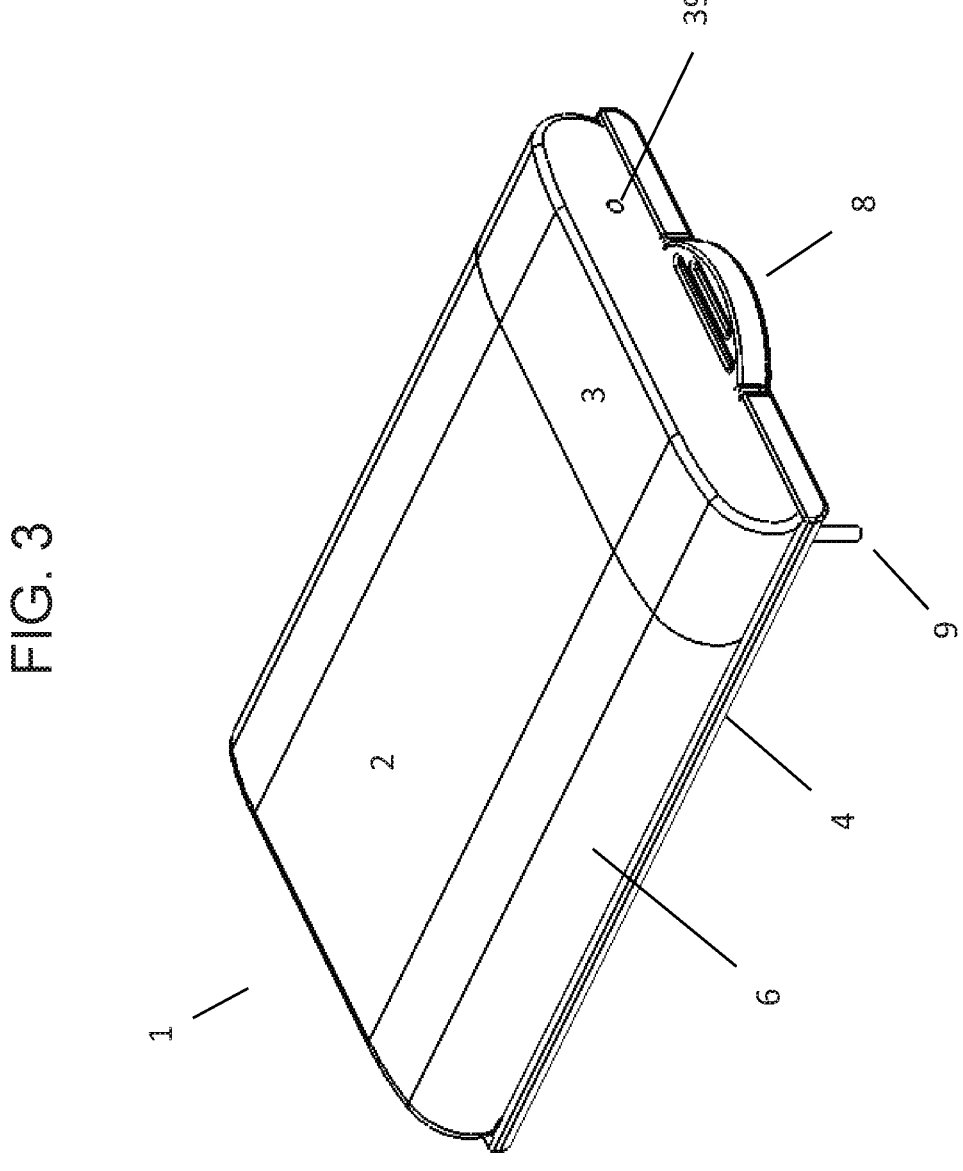
FIG. 3 shows a spatial view of a fluid infusion device, according to some embodiments.

With reference to FIG. 3, in some embodiments, a spatial view of device 1 is shown. Device 1 includes a pump 6 that is comprised of RP 2 and DP 3, a cradle 4 with snap 8, and a cannula 9. DP includes a filling port 39.

Figures 4A, 4B:
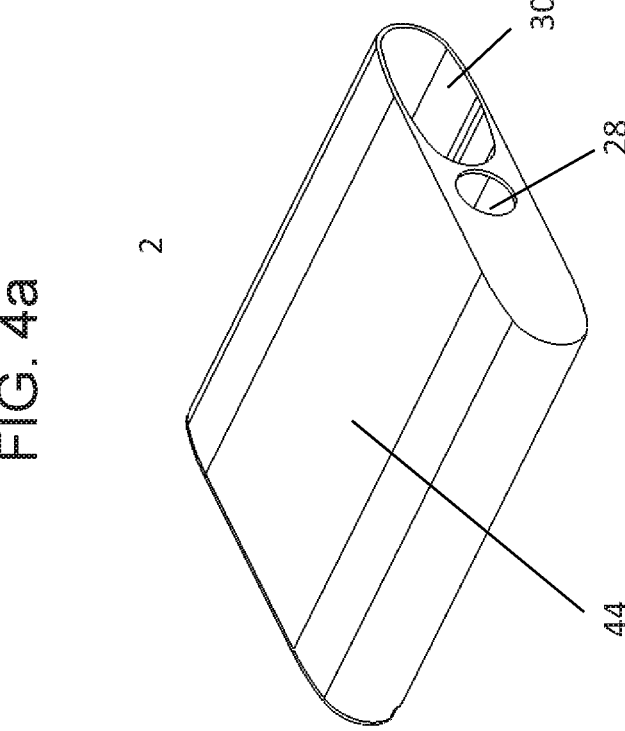
FIGS. 4A-B shows spatial views of the reusable part (RP) and the disposable part (DP), according to some embodiments.

With reference to FIGS. 4A-B, in some embodiments, spatial views of RP 2 and DP 3 are shown. RP 2 includes a rigid shell 44 and two openings—oval opening 30 and round opening 28. DP 3 includes a reservoir 32, a doser 33, and a filling port 39.

Figure 5B:
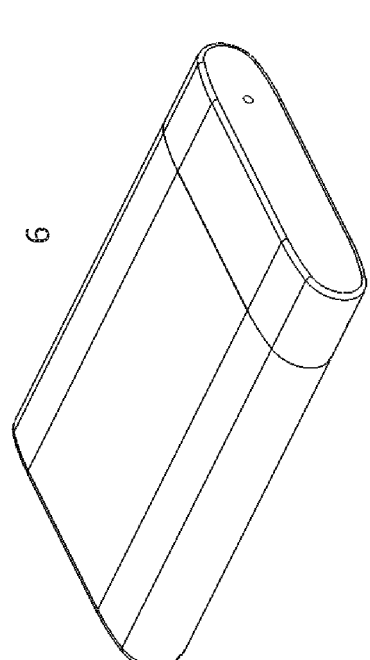
FIGS. 5A-B show spatial views before and after connection of the reusable part and the disposable parts, according to some embodiments.
Figure 5A:
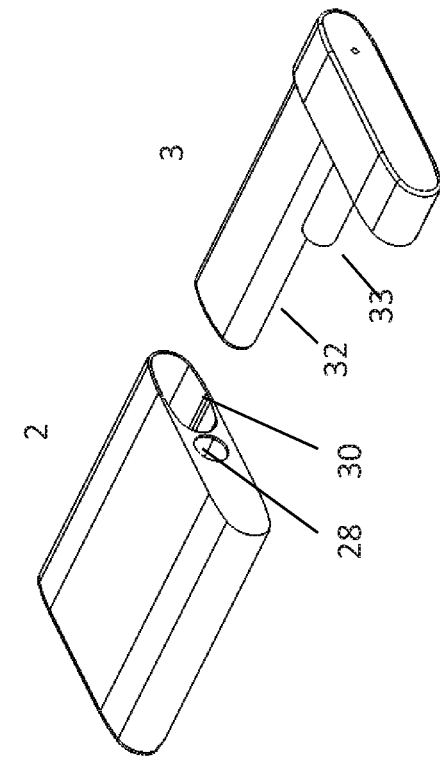

With reference to FIGS. 5A-B, in some embodiments, spatial views before and after connection of RP 2 and DP 3 forming pump 6, respectively, are shown. Oval reservoir 32 and round doser 33 are aligned with openings 30 and 28 respectively.

Figure 6:
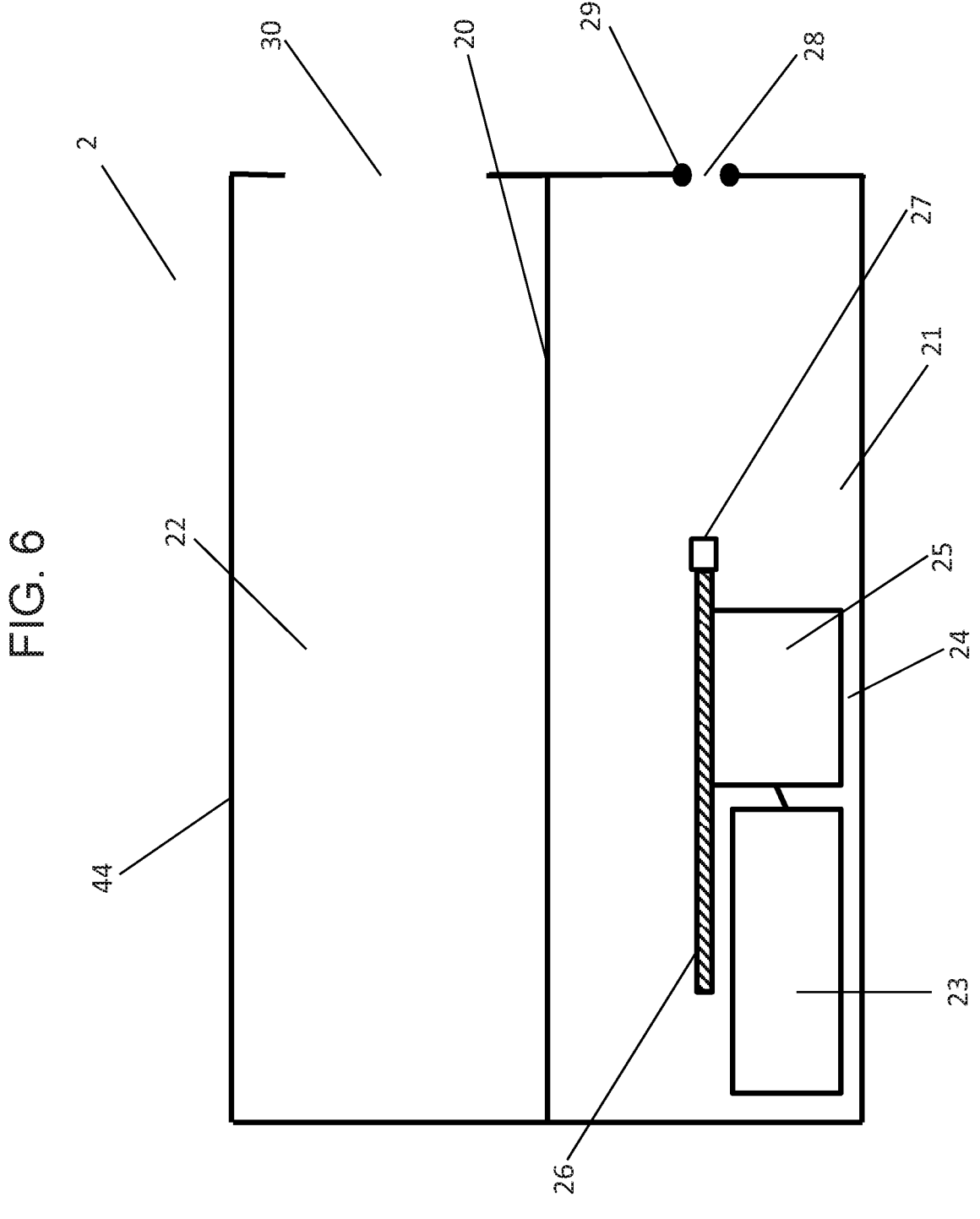
FIG. 6 shows a scheme of the reusable part, according to some embodiments.

With reference to FIGS. 6, in some embodiments, a scheme of RP 2 is shown. RP 2 comprises a shell 44 and a septum 20. Septum 20 separates RP 2 into a first compartment 21 and a second compartment 22. Shell 44 is rigid and may be made, for example, from metal or plastic. First compartment 21 contains an electronics module 23 and an actuation module 24. Actuation module 24 may comprise an actuator 25 (i.e. motor and gear), a rod 26 (i.e. driving screw), and a rod coupling means 27. First compartment 21 comprises an opening 28 having a circular or round cross-sectional shape, and a gasket 29 disposed around the circumference of opening 29. Gasket 29 seals first compartment 21 in watertight fashion whenever RP 2 and DP 3 are connected. Second compartment 22 has an opening 30, which may have a non-circular cross-section, such as, for example, an oval cross-section. When RP 2 and DP 3 are connected, compartment 22 may not be sealed.

Figure 7:
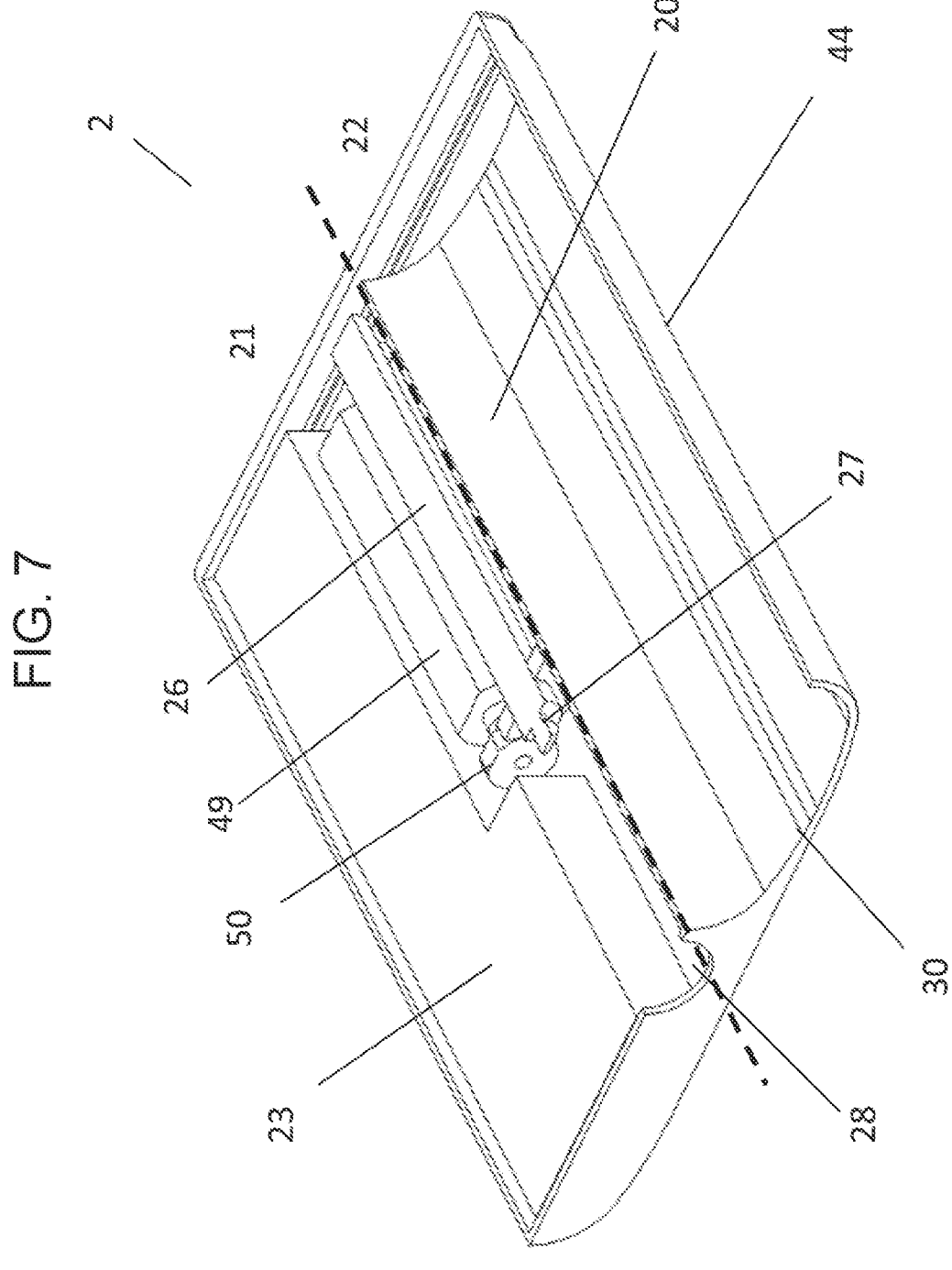
FIG. 7 shows a cross section spatial view of the reusable part, according to some embodiments.

With reference to FIG. 7, in some embodiments, a cross section spatial view of RP 2 is shown. RP 2 comprises the rigid shell 44 and the septum 20 that divides RP 2 (dashed line) into the sealed compartment 21 and the non-sealed ("vented") compartment 22. Non sealed compartment 22 has the opening 30 that may have an oval shape, a round shape, or a four arches shape. Sealed compartment 21 includes opening 28 that has a round shape. Gasket (not shown) is disposed around the circumference of opening 28. Compartment 21 may include electronic unit 23, motor 49, gear 50, rod 26, and rod coupling means 27.

Figure 8:
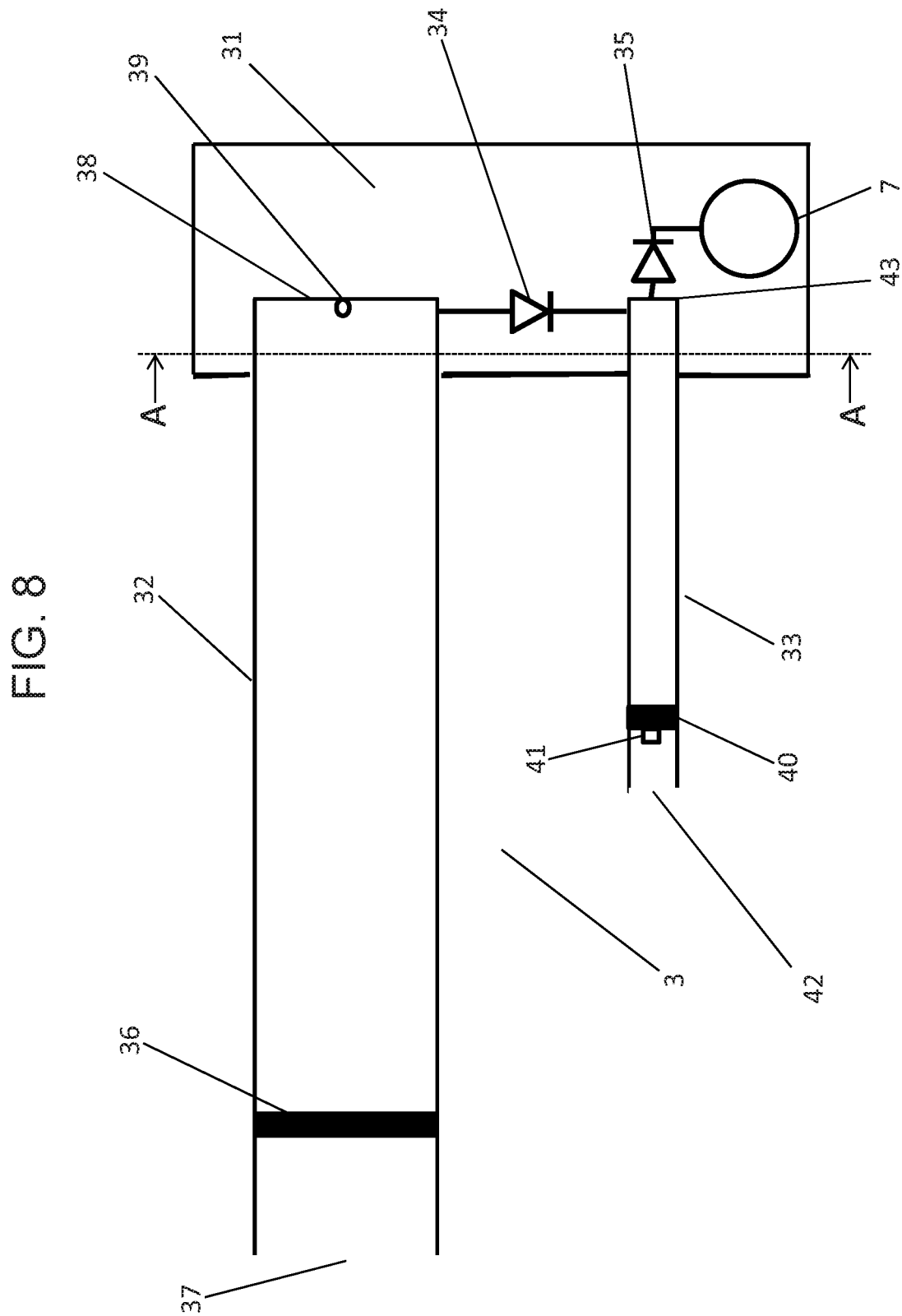
FIG. 8 shows an example scheme of the disposable part, according to some embodiments.

With reference to FIG. 8, in some embodiments, a scheme of one embodiment of DP 3 is shown. DP 3 comprises a base 31, a reservoir 32 for storing infusion fluid, a doser 33 for administering the infusion fluid to the patient in accurate fashion, and an exit port 7. Reservoir 32 and doser 33 may be rigidly connected to base 31. A first check valve 34 may be disposed in base 31 between reservoir 32 and doser 33, such that fluid flow is possible only from reservoir 32 to doser 33 but not in the opposite direction. A second check valve 35 may be disposed in base 31 between doser 33 and exit port 7, such that fluid flow is possible only from doser 33 to exit port 7 but not in the opposite direction. Reservoir 32 may comprise a filling port 39 and a reservoir plunger 36 configured to advance from a first open end 37 of reservoir 32 to a second closed end 38 of reservoir 32. Plunger 36 may also advance from second reservoir end 38 to first reservoir end 37. Filling port 39 may comprise a thin membrane (i.e. a silicone membrane) that may be punctured using a needle and self-resealed upon needle retraction. Doser 33 may comprise a doser plunger 40 configured to advance from a first open end 42 of doser 33 to a second end 43 of doser 33. Doser plunger 40 may also be advanced from second end 43 to first end 42. Doser plunger 40 may be fitted with a plunger coupling means 41. The end-to-end length of doser 33 may be smaller than the end-to-end length of reservoir 32. More specifically, the length of doser 33 may be less than or equal to approximately one half of the length of reservoir 32. The diameter of doser 33 may be less than 8 mm. More specifically, the diameter of doser 33 may be less than about 5 mm.

Figure 9:
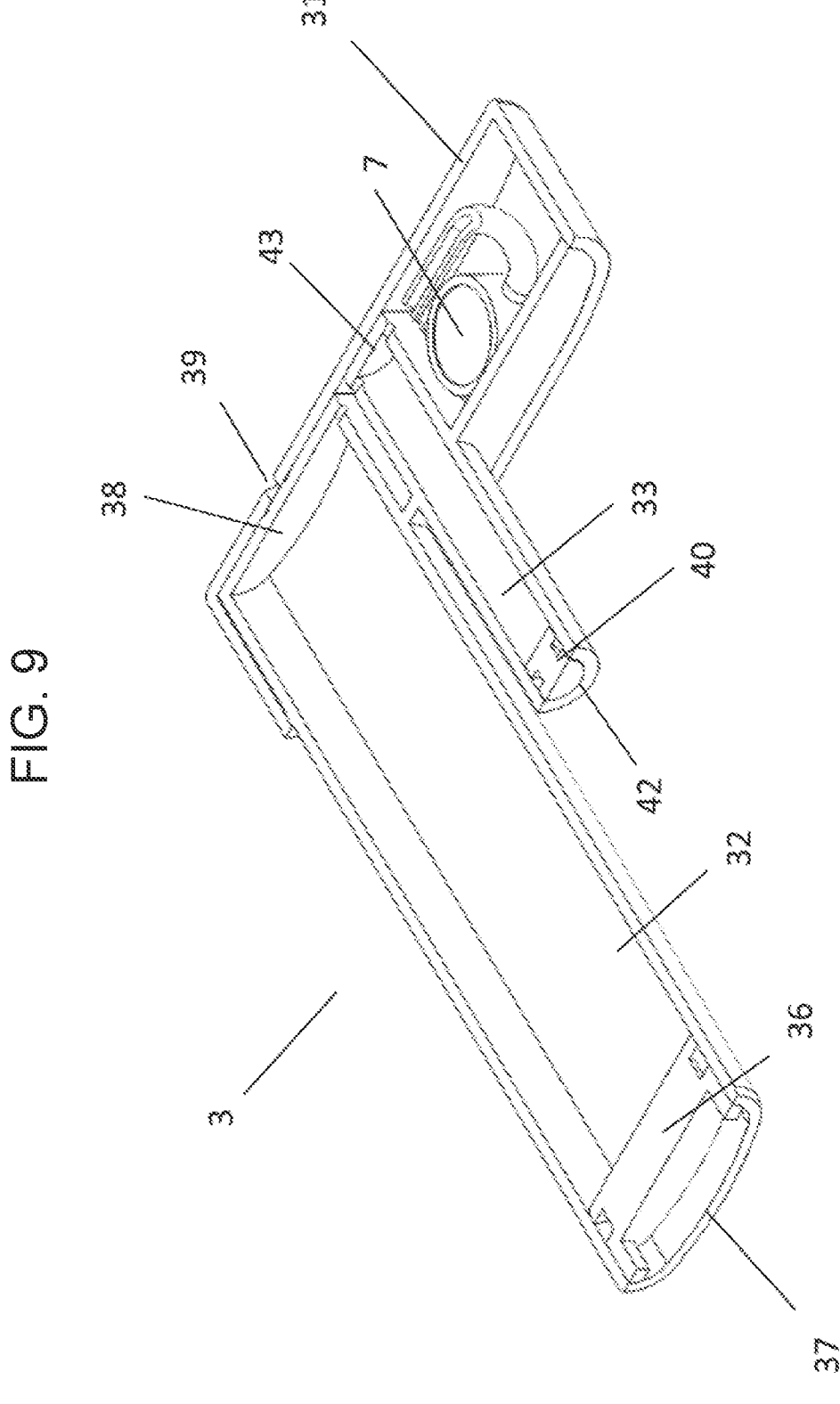
FIG. 9 shows a cross section spatial view of the disposable part, according to some embodiments.

With reference to FIG. 9, in some embodiments, a cross section spatial view of DP 3 is shown. DP 3 includes base 31, exit port 7, reservoir 32 and doser 33. Reservoir 32 includes plunger 36 and filling port 39. Doser 33 includes doser plunger 40. Plunger 36 and doser plunger 40 may move in both directions between first (open) ends 37 and 42 and second ends 38 and 43, respectively.

Figure 10:
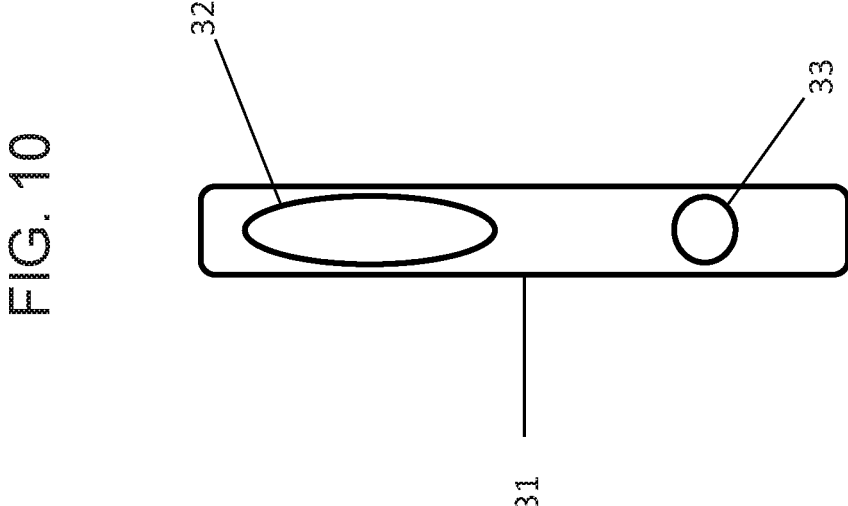
FIG. 10 shows a cross-section view of the disposable part base, according to some embodiments.

With reference to FIG. 10, in some embodiments, a cross-section view of DP base 31 taken at plane A-A of FIG. 8 is shown. The cross section of doser 33 may be circular, thereby allowing for a watertight seal with gasket 29 of RP 2. The cross section of reservoir 32 may be non-circular, for example, elliptical, oblong, or oval, thereby allowing the reservoir to hold a suitable volume of infusion fluid while maintaining the z dimension (thickness) of pump 6 thin. In some embodiments of the present disclosure pump 6 may be less than 10 mm thick, or even less than 8 mm thick, or even less than 6 mm thick.

Figure 11:
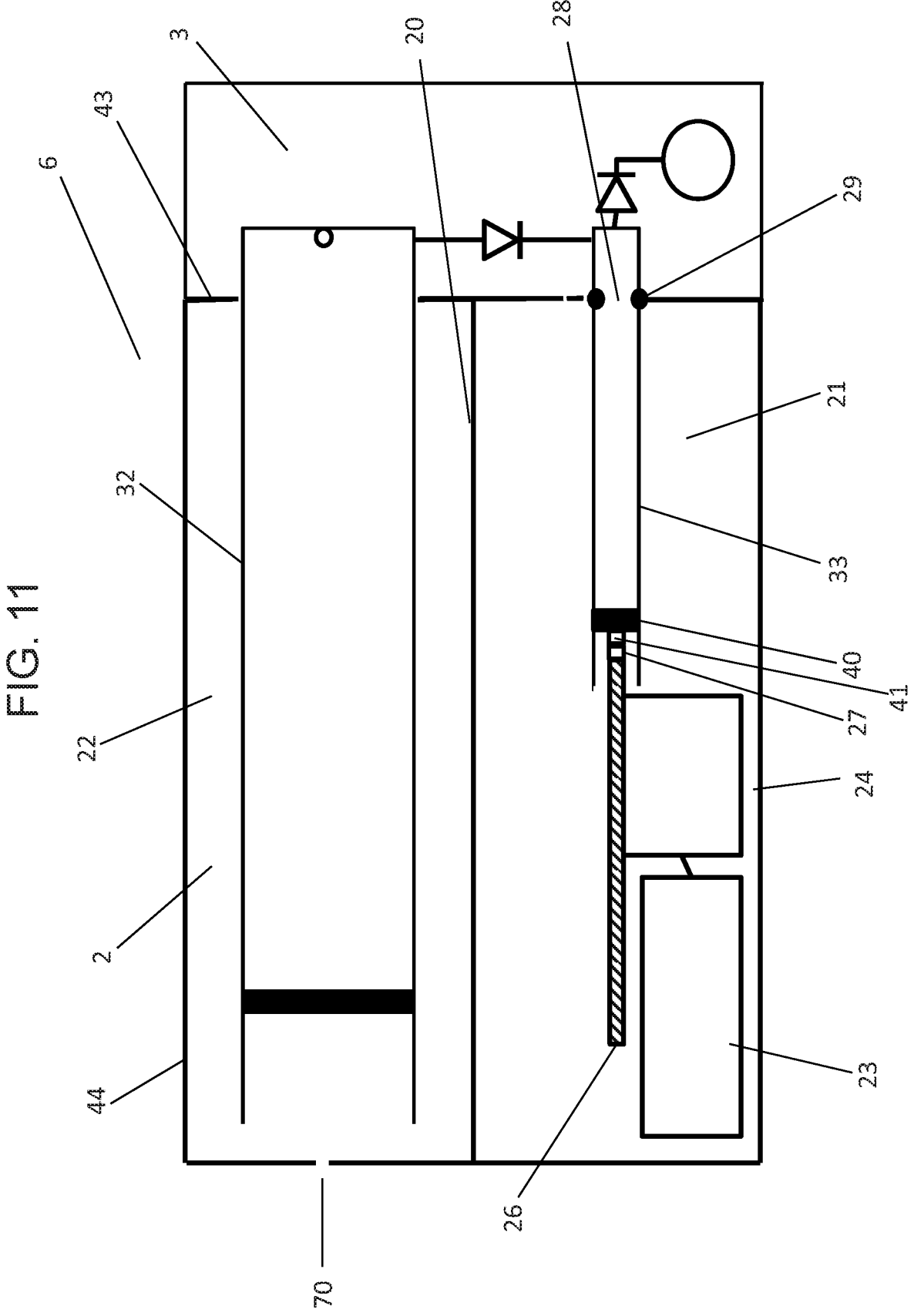
FIG. 11 shows a scheme of the fluid infusion pump, according to some embodiments.
Figure 33:
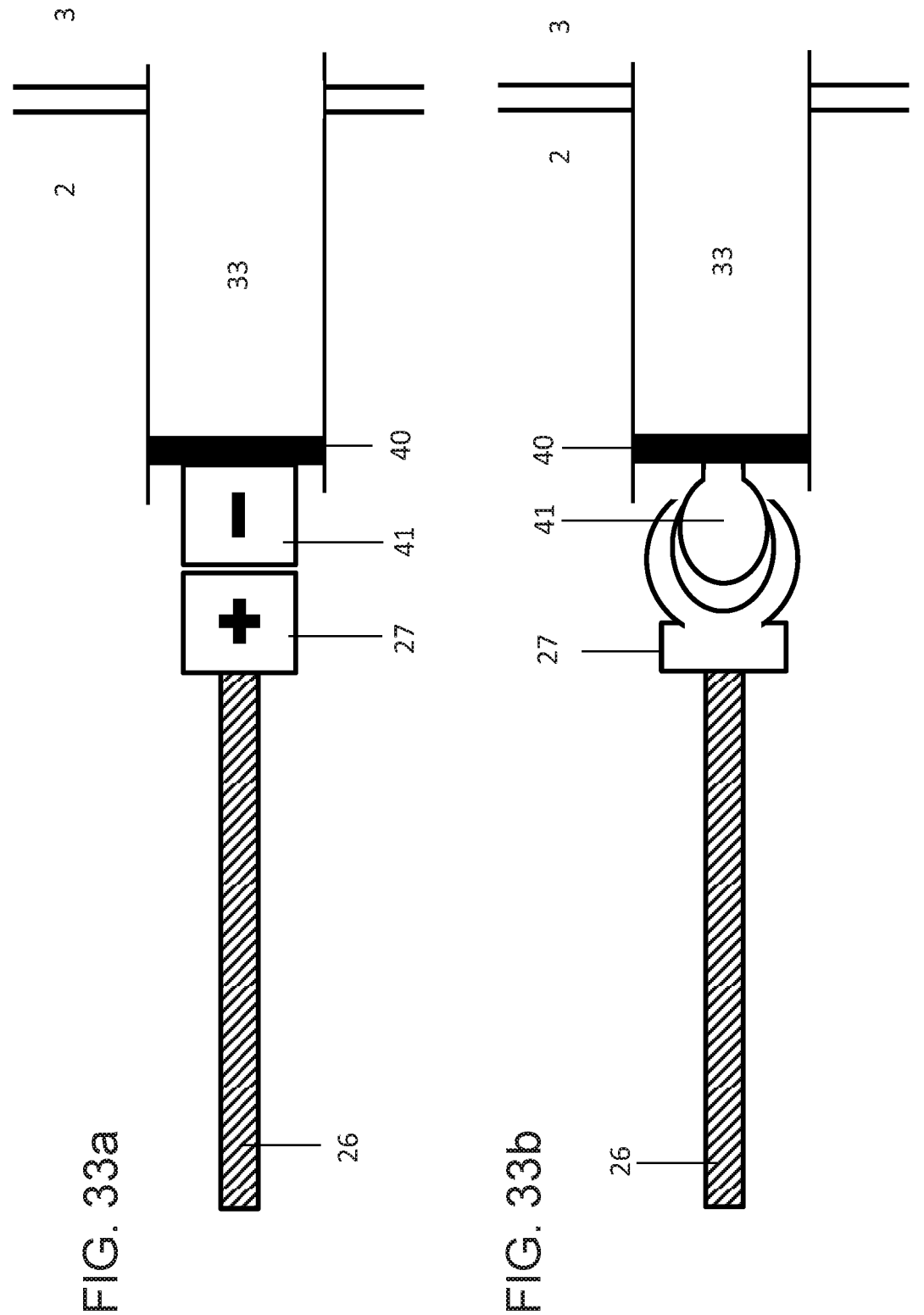
FIGS. 33A-B show schemes of magnetic (A) and mechanical (B) reversible connections of driving screw with doser plunger, according to some embodiments.

With reference to FIG. 11, in some embodiments, a scheme of pump 6 is shown. Pump 6 is obtained by reversibly connecting RP 2 and DP 3. Whenever RP 2 and DP 3 are connected to form pump 6, second reservoir (or "doser") 33 is received within first compartment 21 of RP 2, and first reservoir 32 (or "reservoir") may be received within second compartment 22 of RP 2. Septum 20 may provide a complete sealed separation between the two compartments. Gasket 29, which may be situated at opening 28 of RP 2 may form a watertight seal around doser 33, thereby allowing for watertight sealing of compartment 21 of pump 6. Water and moisture may thus be kept away from all components situated in compartment 21, including electronics module 23 and actuation module 24. Interface 43 between compartment 22 and DP 3 may or may not accommodate a watertight seal. In some embodiments of the present disclosure, a semiper-meable seal is disposed on interface 43, which prevents dirt from entering compartment 22 but allows air to communi-cate freely between the compartment and the exterior envi-ronment. This may allow for pressure equilibration between compartment 22 and the surrounding atmosphere. In another embodiment, pressure equilibration may be achieved with a small opening 70 in shell 44. In some embodiments, reser-voir 32 within compartment 22 is not touching shell 44. Thus, shell 44 provides reservoir 32 protection against compression by external forces and subsequent uninten-tional release of infusion fluid from reservoir 32. Whenever RP 2 and DP 3 are connected to form pump 6, rod 26 and doser plunger 40 may be engaged. Engagement may be achieved by means of a reversible connection between rod coupling means 27 and doser plunger coupling means 41. In some embodiments of the present disclosure, rod coupling means 27 may comprise a magnet having a certain polarity and a plunger coupling means 41 may have the opposite polarity. In some embodiment of the present disclosure, coupling means 27 and 41 may be a "male-female" engage-ment mechanism such as snap mechanism or any other known in art engagement mechanism. Once coupling means 27 and 41 are connected, linear movement of rod 26 causes doser plunger 40 to make a corresponding linear motion. Detailed description of coupling mechanisms is shown in FIG. 33.

Figure 12:
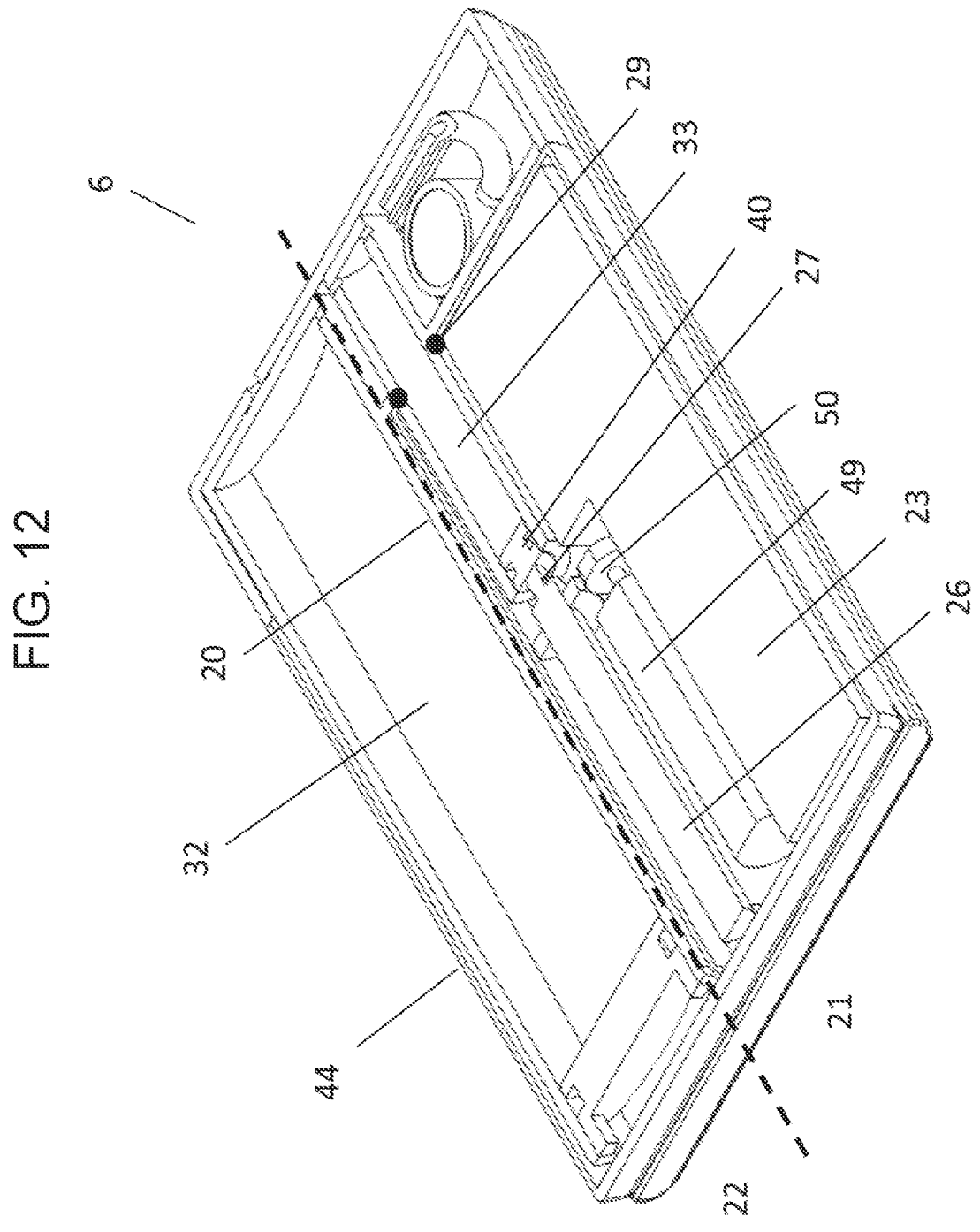
FIG. 12 shows a cross section spatial view of the pump after connection of the reusable part and the disposable part, according to some embodiments.

With reference to FIG. 12, in some embodiments, a cross section spatial view of pump 6 after connection of RP 2 and DP 3 is shown. Doser 33 and reservoir 32 are received within sealed compartment 21 and vented compartment 22 of RP 2 respectively. Doser 33 and reservoir 32 are protected from outside pressure by rigid shell 44. Septum 20 provides a complete sealed separation between the two compartments (dashed line). Sealing of compartment 21 is achieved with gasket 29. Sealed compartment 21 includes electronics mod-ule 23, motor 49, gear 50, rod 26, and coupling means 27. After connection of DP 3 and RP 2, rod coupling means 27 and plunger coupling means (not shown) are engaged.

Figure 13:
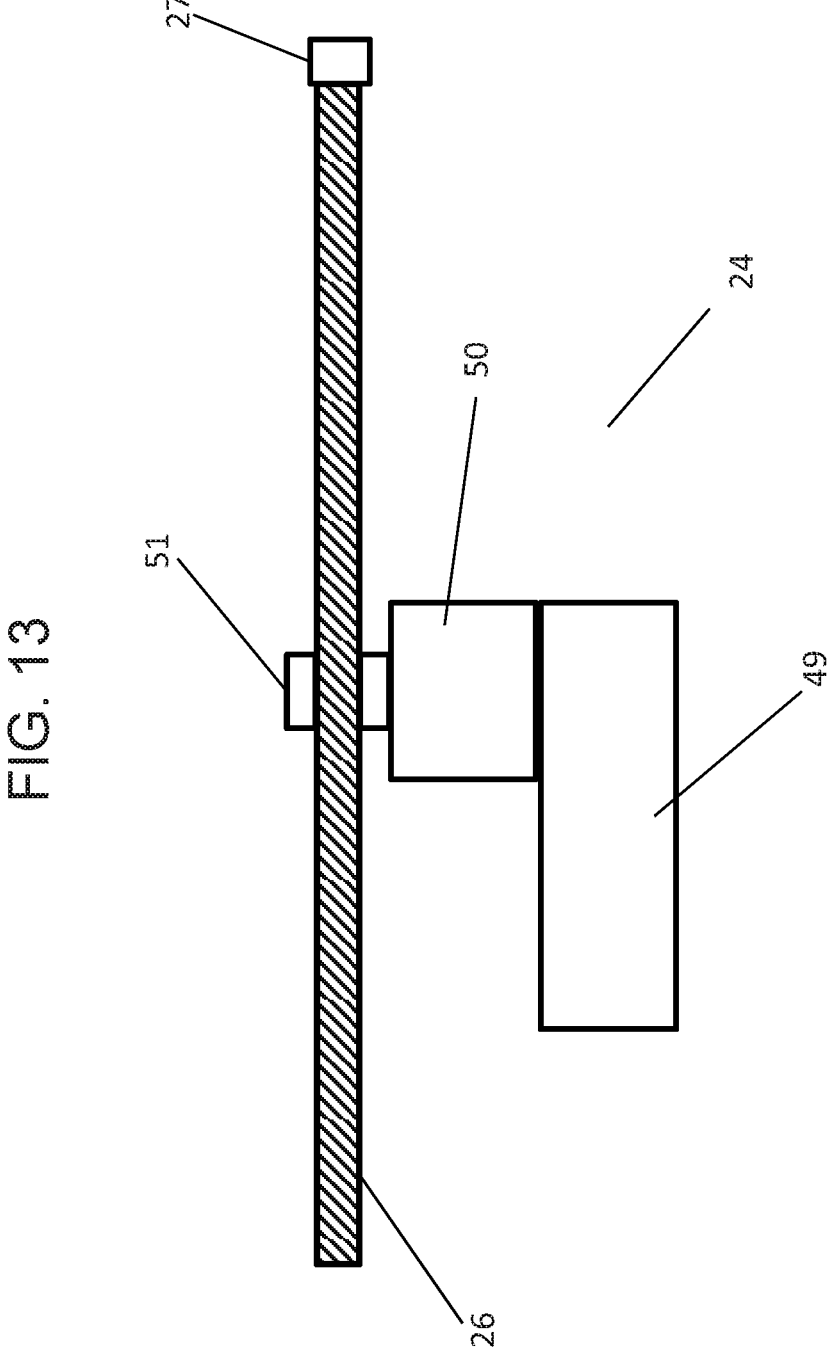
FIG. 13 shows a scheme of the actuation module, according to some embodiments.

With reference to FIG. 13, in some embodiments, a scheme of actuation module 24 is shown. Actuation module 24 may comprise motor 49, 1$^{st}$ gear 50, rotatable nut 51 (hereinafter "nut"), rod 26, and rod coupling means 27. Motor 49 may be an electrical motor. In some embodiments of the present disclosure motor 49 may be of the following types: a DC motor, a universal motor, an AC motor, a stepper motor, a permanent magnet motor, a brushed DC motor, a brushless DC motor, a switched reluctance motor, a coreless DC motor, a printed armature or pancake DC motor, an AC motor with sliding rotor, a synchronous electric motor, an induction motor, a doubly fed electric motor, a singly fed electric motor, and a torque motor. Gear 50 may be, for example, a planetary gear system configured to translate a rotational output of motor 49 into a linear motion of rod 26. In some embodiments of the present disclosure, gear 50 may comprise a rotatable nut 51. Nut 51 may be threaded, and rod 26 may be counter-threaded with respect to nut 51. Gear 50 may translate a rotational output provided by motor 49 into rotational motion of nut 51, which is then transmitted by the nut's thread to the rod's counter-thread thereby causing the rod to move forward or backward in the direction of the rod's axis.

Figure 14:
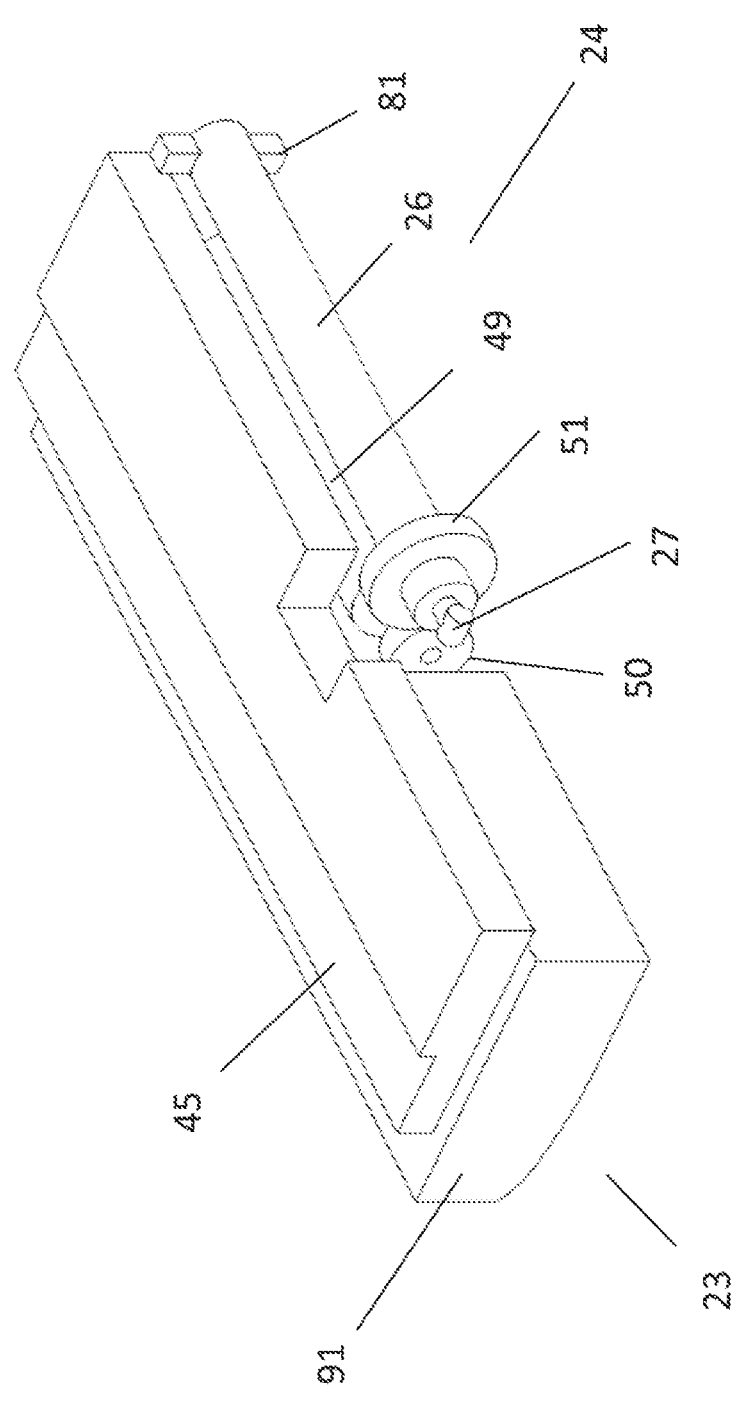
FIG. 14 shows spatial views of the electronic module and the actuation module, according to some embodiments.

With reference to FIG. 14, in some embodiments, spatial view of electronic module 23 and actuation module 24 is shown. Electronic module includes printed circuit board (PCB) 91 and battery 45. PCB comprises hardware and software components. Actuation module includes motor 49, gear 50, nut 51, rod 26, rod coupling means 27, and a revolution sensor 81.

Figures 15A, 15B, 15C, 15D, 15E, 15F:
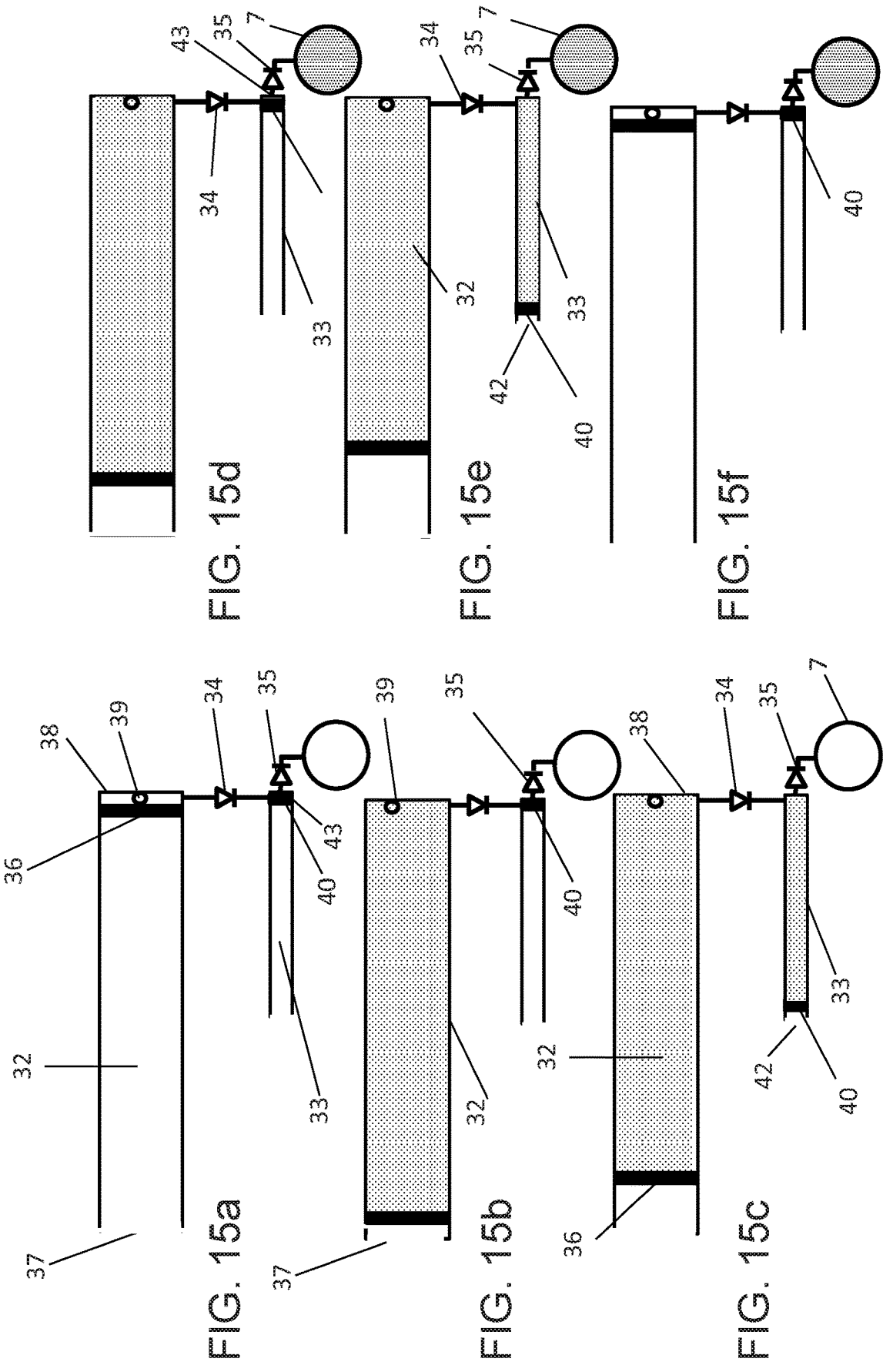
FIGS. 15A-F show a scheme of the pumping mechanism, according to some embodiments.

With reference to FIG. 15, in some embodiments, a scheme of pumping mechanism of pump 6 is shown. This configuration comprises two openings in reservoir 32, two openings in doser 33, and two check valves 34 and 35. For ease of understanding, only those components of the pump that come in contact with the infusion fluid are depicted. FIG. 15*a* shows the initial state of the pumping mechanism, before it is filled with infusion fluid. Reservoir plunger 36 is situated near second reservoir end 38, with filling port 39 disposed between plunger 36 and end 38. Doser plunger 40 is situated near second doser end 43. Doser plunger 40 seals the opening (not shown) through which fluid communica-tion is established between first check valve 34 and the interior of doser 33. FIG. 15*b* shows the state of the pumping mechanism immediately after reservoir 32 is filled with infusion fluid. Infusion fluid is injected into reservoir 32 through port 39 using, for example, a syringe. The infusion fluid is prevented from entering doser 33 by means of plunger 40 interrupting fluid communication between check valve 34 and the interior of doser 33. Thus, the infusion fluid fills reservoir 32, displacing plunger 36 in the direction of first opening 37 of reservoir 32. Filling concludes when, for example, plunger 36 reaches a stopper (not shown) situated near opening 37. FIG. 15*c* shows the state of the pumping mechanism immediately after doser plunger 40 reaches a position closest to first doser opening 42 after moving in the direction of first doser opening 42. (Movement of plunger 40 is caused by rod 26, which is not shown). The movement of plunger 40 towards end 42 causes fluid from reservoir 32 to flow into doser 33 through check valve 34, thereby filling doser 33. Note that fluid flow from exit port 7 into doser 33 is prevented by check valve 35. In transition between the states depicted in FIGS. 15*b* and 15*c*, the volume of fluid entering the doser 33 is substantially equal to the volume of fluid lost by the reservoir 32. Thus, reservoir plunger 36 moves in the direction of end 38 a distance equal to the doser volume divided by the cross sectional area of the reservoir 32. FIG. 15*d* shows the state of the pumping mechanism immediately after doser plunger 40 reaches its initial posi-tion near second end 43 of doser 33 once again. The movement of plunger 40 displaces the infusion fluid con-tained within doser 33 towards exit port 7 through second check valve 35. The fluid is prevented from flowing back into reservoir 32 by check valve 34. FIG. 15*e* shows the state of the pumping mechanism immediately after doser plunger 40 reaches yet again its position closest to first end 42 of doser 33. Upon reaching the position, the doser is refilled by infusion fluid flowing into it from reservoir 32 through check valve 34. Fluid residing between the doser and exit port 7 is prevented from re-entering the doser by means of check valve 35 FIG. 8*f* shows the state of the pump immediately after doser plunger 40 has cycled as many times as required between its two extreme positions to empty all of the infusion fluid in reservoir 32 through exit port 7. The pump has thus returned to its initial position as depicted in FIG. 15*a*, except that exit port 7 may not be completely empty of infusion fluid. Note that doser plunger 40 need not reach either of its extreme positions in order to displace fluid from the reservoir through the exit port. In some embodiments, the plunger 40 may be displaced by any amount. Plunger 40 may be displaced according to a pre-determined program stored, for example, on a microproces-sor in order to provide a predetermined infusion profile.

Figures 16A, 16B:
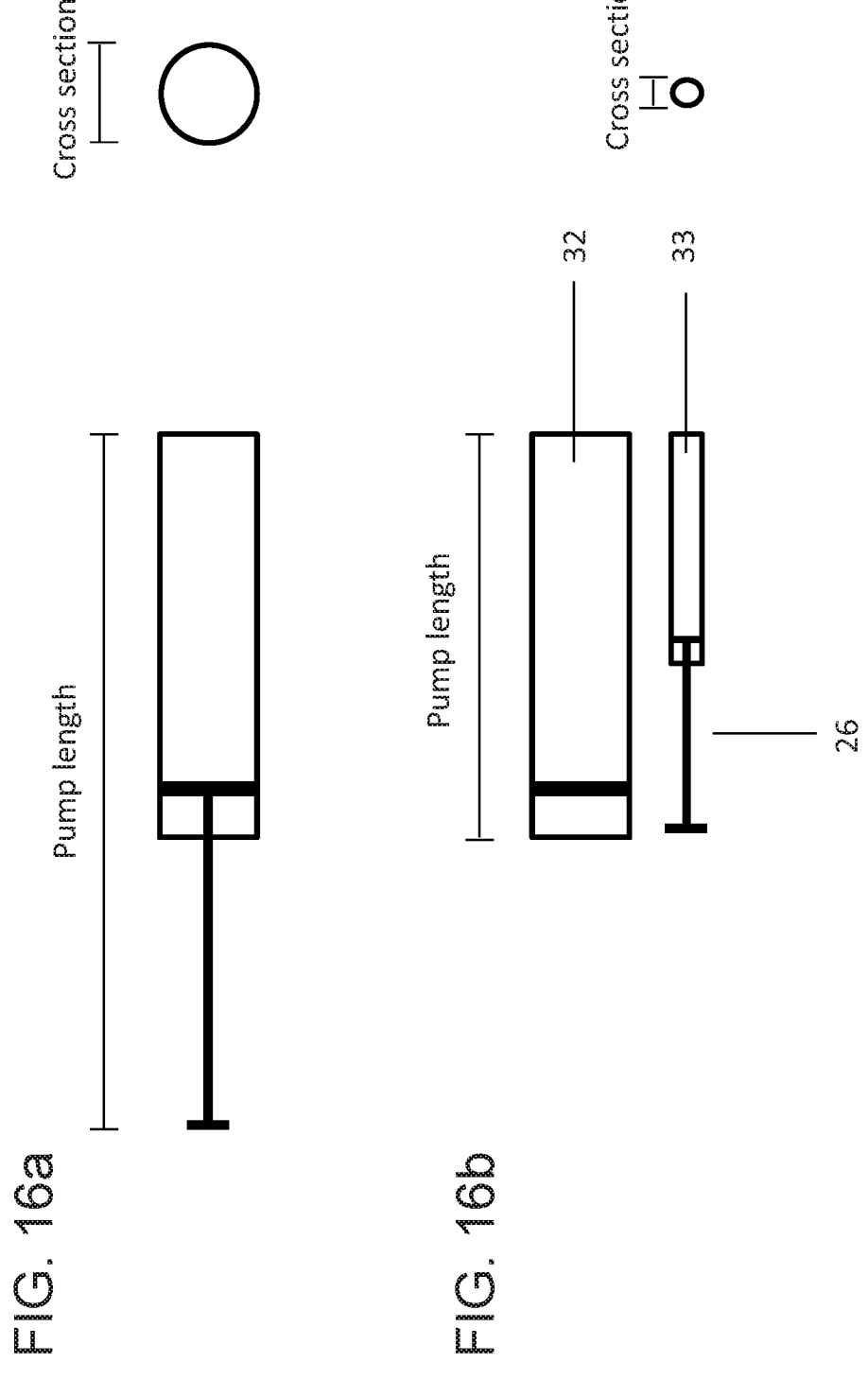
FIGS. 16A-B show schemes of pumping mechanism, according to some embodiments.

With reference to FIGS. 16A-B, in some embodiments, pumping mechanism schemes are shown. The pumping mechanism of pump 6 is advantageous in terms of both size and accuracy, discussed in more details below.

Size: Total pump length may be approximately the same as the reservoir length. This is because the combined length of doser 33 and rod 26 is roughly equal to the length of reservoir 32. In conventional syringe pumps, in which the doser and the reservoir are one and the same, the pump length needs to be greater than or equal to the combined lengths of the reservoir and a plunger rod. Thus, in some embodiments of the present disclosure the length of the pump may be less than or equal to one half the length of an equivalent conventional syringe pump.

Accuracy: Dosing may be much more accurate in some embodiments of the present disclosure than in an equivalent conventional syringe pump. This is because the cross sectional area of the doser 33 (denoted a) may be 10-100 times smaller than the cross sectional area A of the reservoir 32. Thus, in a conventional syringe pump a plunger displacement error d translates into a volume displacement error d*A (assuming that the cross sectional area of a conventional syringe pump is similar to the cross sectional area A of reservoir 32.). In some embodiments according to the present disclosure, the same plunger displacement error d would translate into a volume displacement error d*a, which is 10-100 smaller than in conventional syringe pumps.

Figures 17A, 17B:
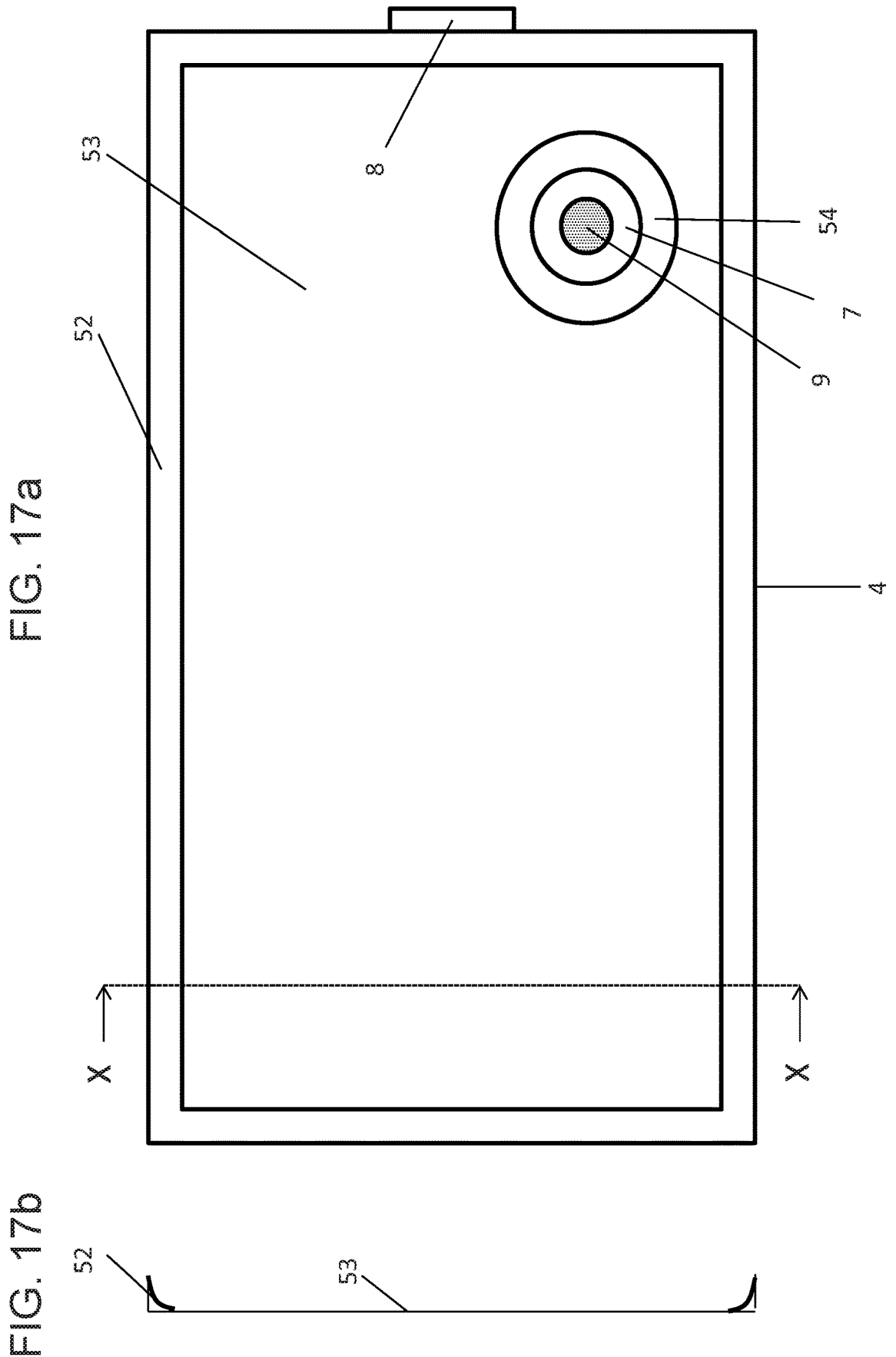
FIGS. 17A-B show schemes of upper and cross section views of the cradle, according to some embodiments.

With reference to FIGS. 17A-B, in some embodiments, schemes of upper view 17a and cross section view 17b of cradle 4 are shown. In some embodiments, cradle 4 comprises a frame 52 and a bottom side 53 (FIG. 17b). In some embodiments according to the present disclosure, frame 52 may have a cross-sectional area that is square, rectangular or slightly curved (FIG. 17b). The curved shape is configured to complement the cross-sectional curved shape of pump 6 (FIG. 3), thereby allowing the pump to fit into the cradle without increasing the thickness of the overall structure beyond the thickness of pump 6. Frame 52 may be rigid or flexible to accommodate strains caused by skin movement. Bottom side 53 of cradle 52 may be made of adhesive paper and protection liner to be removed before use. In some embodiments, bottom side 53 may comprise an opening 54 configured to receive exit port 7 and a cannula 9. Opening 54 may allow the patient to visually inspect skin in the close vicinity of cannula 9 for bleeding or irritation. In some embodiments of the present disclosure reversible connection between pump 6 and cradle 4 may be implemented using a snap mechanism 8.

Figures 18A, 18B:
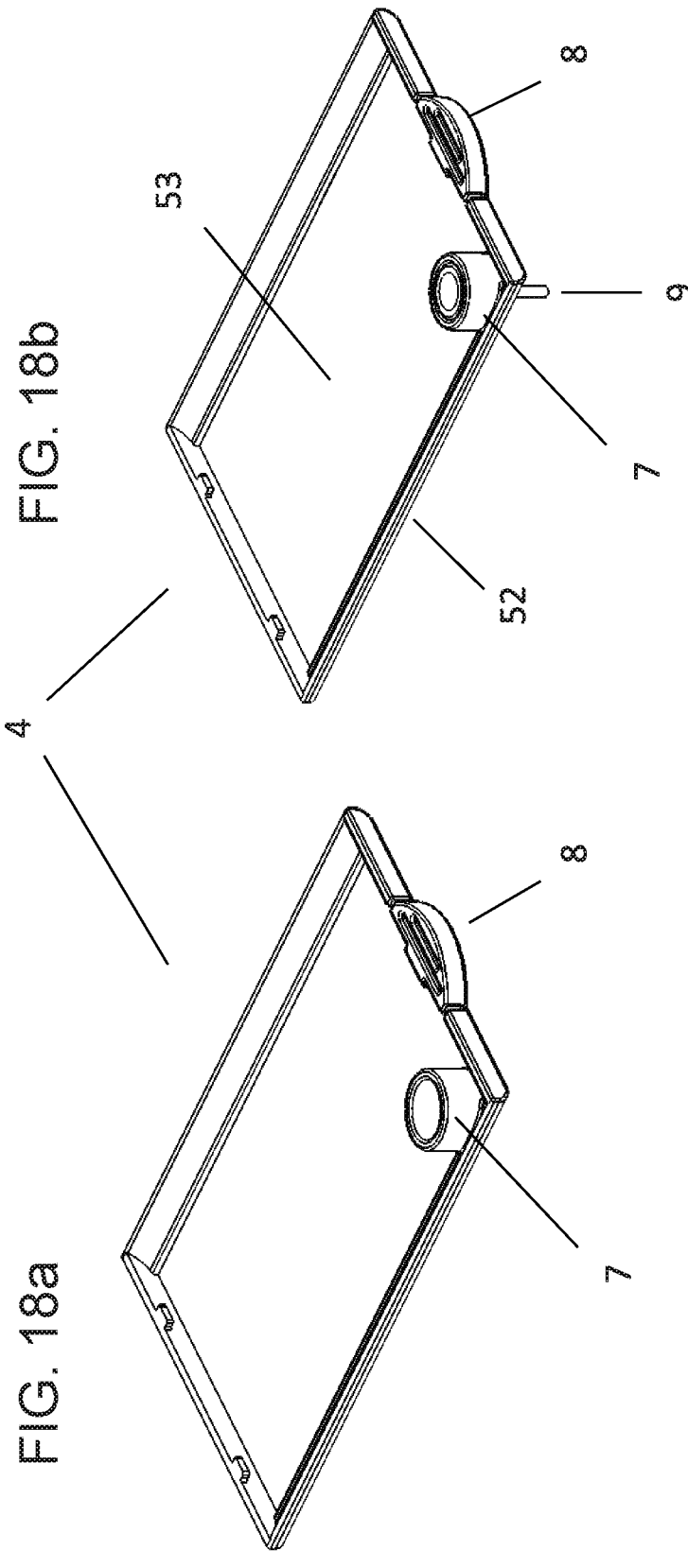
FIGS. 18A-B show spatial views of the cradle before (A) and after (B) cannula insertion, according to some embodiments.

With reference to FIGS. 18A-B, in some embodiments, spatial views of cradle 4 before (18a) and after (18b) cannula insertion are shown. In some embodiments, cradle 4 comprises frame 52, bottom side (i.e. adhesive) 53, exit port 7, and snap mechanism 8. After insertion, cannula 9 is received within exit port 7.

With reference to FIGS. 19A-C, in some embodiments, schemes of infusion site interface 10 are shown. Infusion site interface comprises a cannula inserter 5, cradle 4, and cannula 9. FIG. 19a shows infusion site interface 10 with inserter 5 in the un-deployed state. Inserter 5 comprises cannula 9, spring 55, and spring release button 56. Cannula 9 may comprise a sharp penetrating member 57 and an extra-cutaneous member 58. Member 58 may be comprised of a flexible septum (i.e. silicone) disposed at its top end. To deploy cannula 9 into the patient's body, infusion site interface 10 is attached to patient skin 80 and cradle 4 is adhered to skin 80. FIGS. 19b and 19c show the insertion process. Upon pressing button 56, spring 55 is released and shoots penetrating member 57 and cannula 9 into the skin 80. Subsequently, penetrating member 57 is retracted, maintaining cannula 9 within the body and member 58 external to the skin (FIG. 19c). Finally, inserter 5 including penetrating member 57 is disposed (not shown) and cradle 4 remains adhered to skin.

Figures 20A, 20B, 20C, 20D:
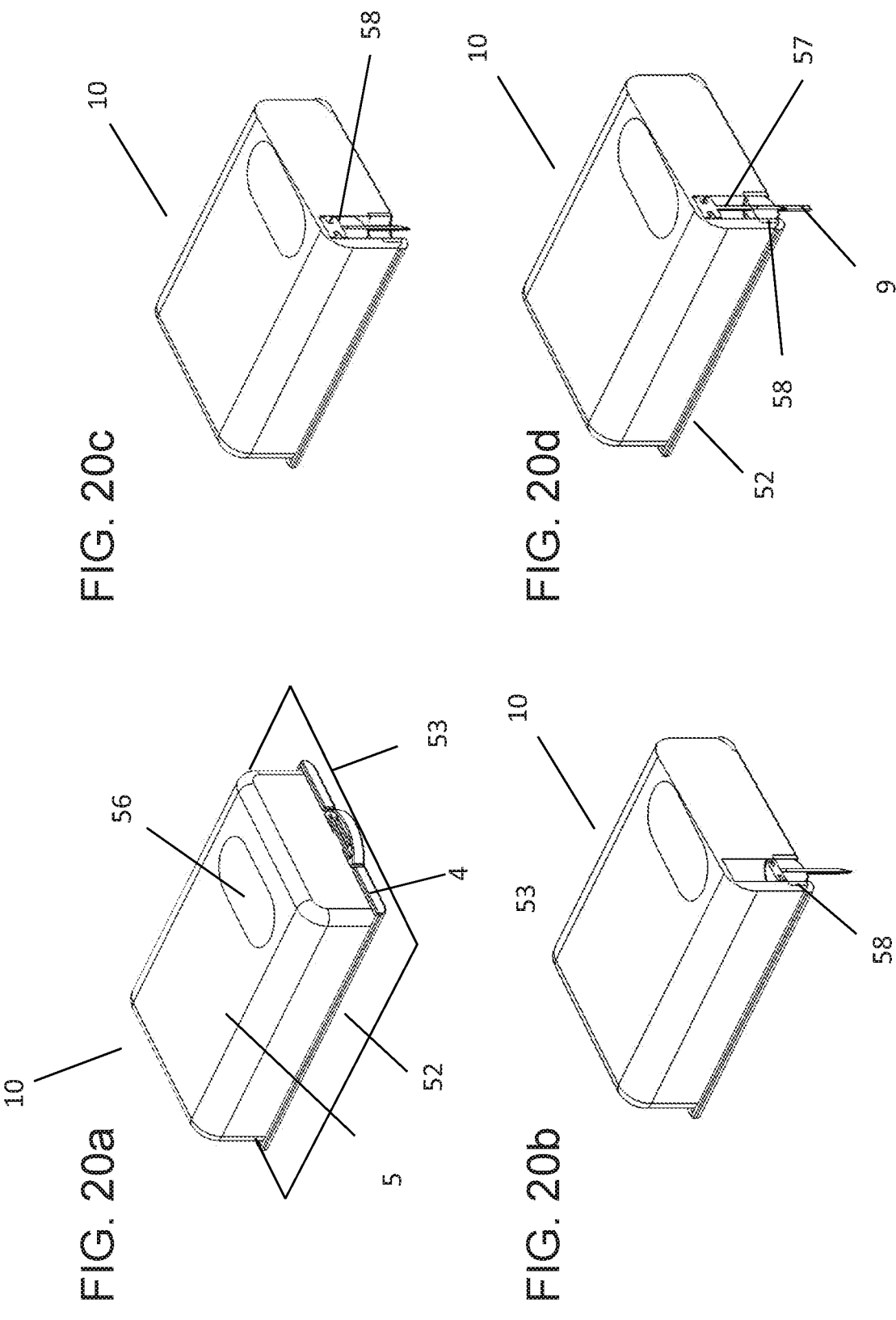
FIGS. 20A-D show spatial views of infusion site interface (e.g., inserter, cradle and cannula) and insertion mechanism, according to some embodiments.

With reference to FIGS. 20A-D, in some embodiments, spatial views of infusion site interface 10 are shown. Infusion site interface 10 comprises inserter 5, cannula 9, and cradle 4. In some embodiments, infusion site interface 10 is a disposable assembly that is preassembled with cannula 9 and cradle 4 at a sterile blister (not shown). After removal from blister and liner peeling of adhesive from cradle bottom side 53, the infusion site interface is attached to patient's skin at a desired location. Upon pressing button 56, cannula 9 is automatically inserted and subsequently, penetrating member 57 is retracted. FIG. 20a and FIG. 20b (cross section) show the infusion site interface 10 before insertion of cannula 9 by inserter 5. FIGS. 20c and 20d (cross sections) show insertion of cannula 9 and retraction of penetrating member 57 while maintaining member 58 above cradle frame 52. After insertion, cradle 4 is attached to skin and cannula 9 resides in the subcutaneous tissue below the skin.

Figures 21A, 21B, 21C, 21D:
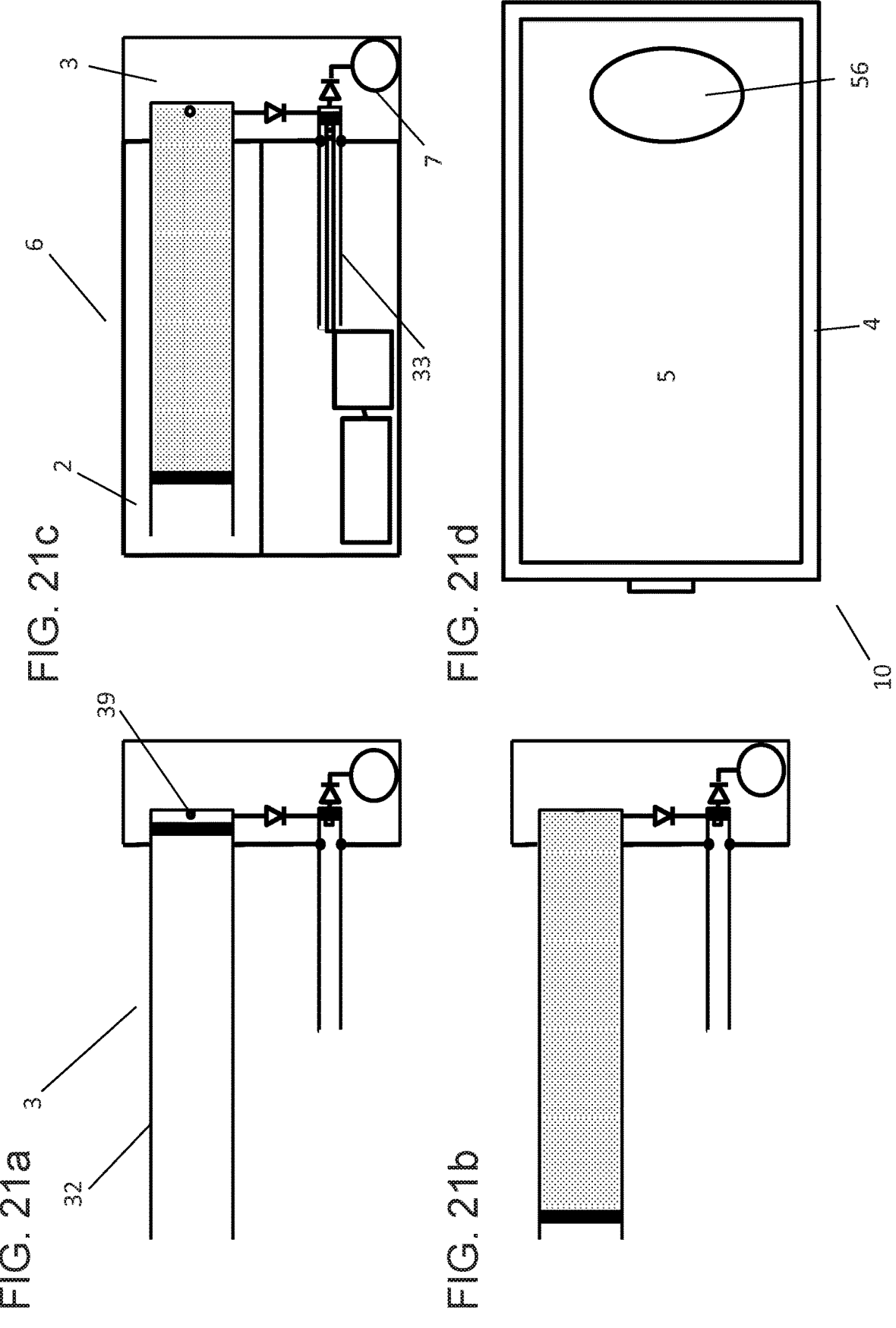
FIGS. 21A-F show schematically upside views of device preparation for operation, according to some embodiments.
Figures 21E, 21F:
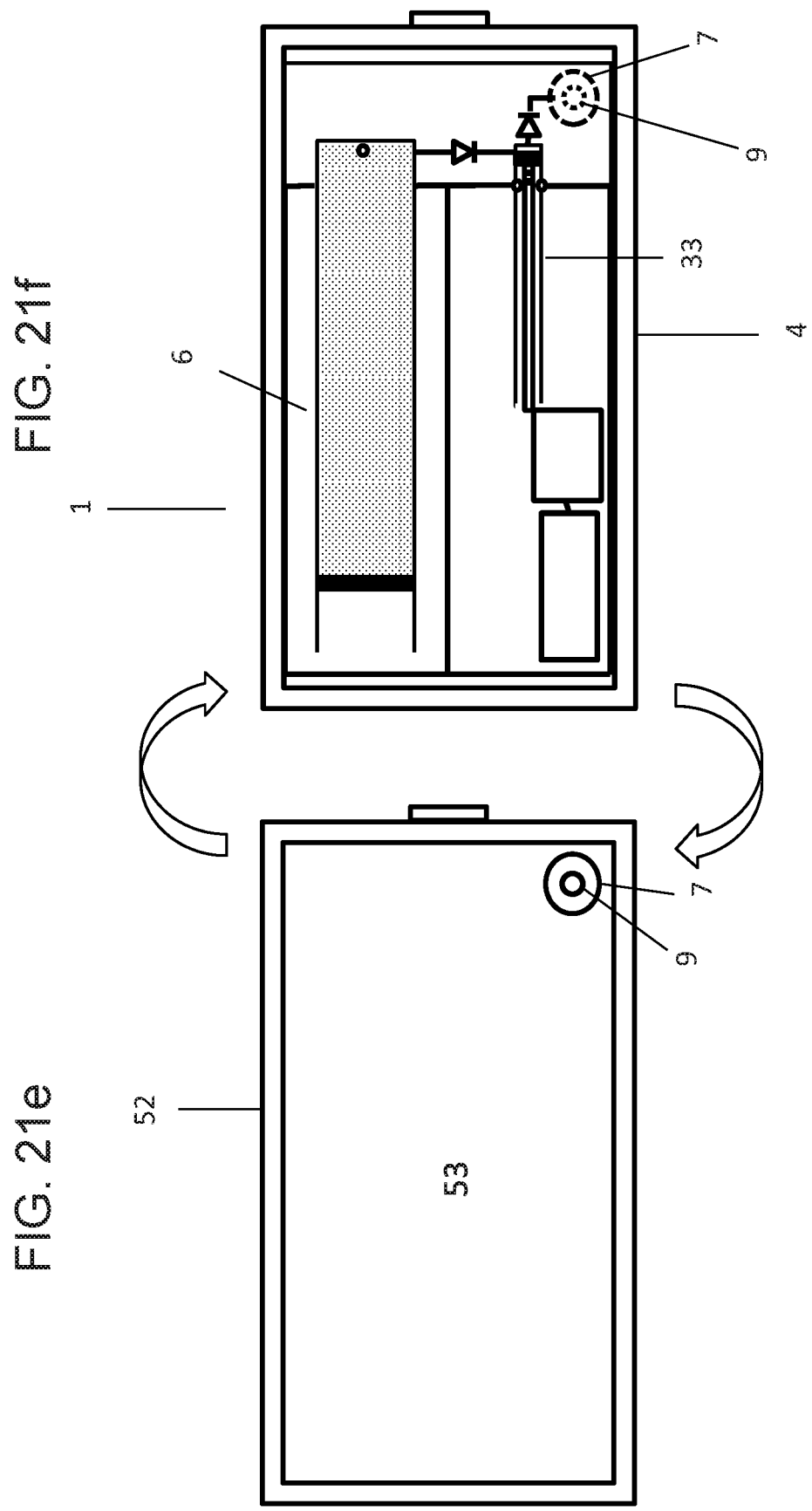

With reference to FIGS. 21A-F, in some embodiments, schematic upside views of device 1 preparation for operation are shown. First, the user extracts DP 3 from a sterile package (not shown) in its initial state (FIG. 21a). The user then fills reservoir 32 with infusible fluid through filling port 39 using a syringe configured with a needle (not shown). Once the reservoir is filled to the extent required by the user, the syringe needle is withdrawn from filling port 39 and the septum disposed therein self-seals. The situation is now shown in FIG. 21b. In the next step RP 2 and DP 3 are connected to form a pump 6 (FIG. 21c) and priming (air purging) is performed (detailed in FIG. 22). FIG. 21d shows the infusion site interface that comprises inserter 5 with operating button 56 and cradle 4. After cannula 9 insertion, inserter 5 is removed from cradle 4 (FIG. 21e), frame 52 is connected to adhesive 53 and cannula 9 resides within exit port 7. Finally (FIG. 21f, pump 6 is connected to cradle 4 and device 1 is ready to go. Connection of pump 6 to cradle 4 provides fluid communication between pump 6 and cannula 9 and fluid can be delivered from doser 33 to body. Connection of pump 6 and cradle 4 is reversible (curved arrows), thus patient can refill reservoir or replace RP (i.e. low battery) upon his/her discretion (detailed in FIG. 23).

Figures 22A, 22B, 22C, 22D:
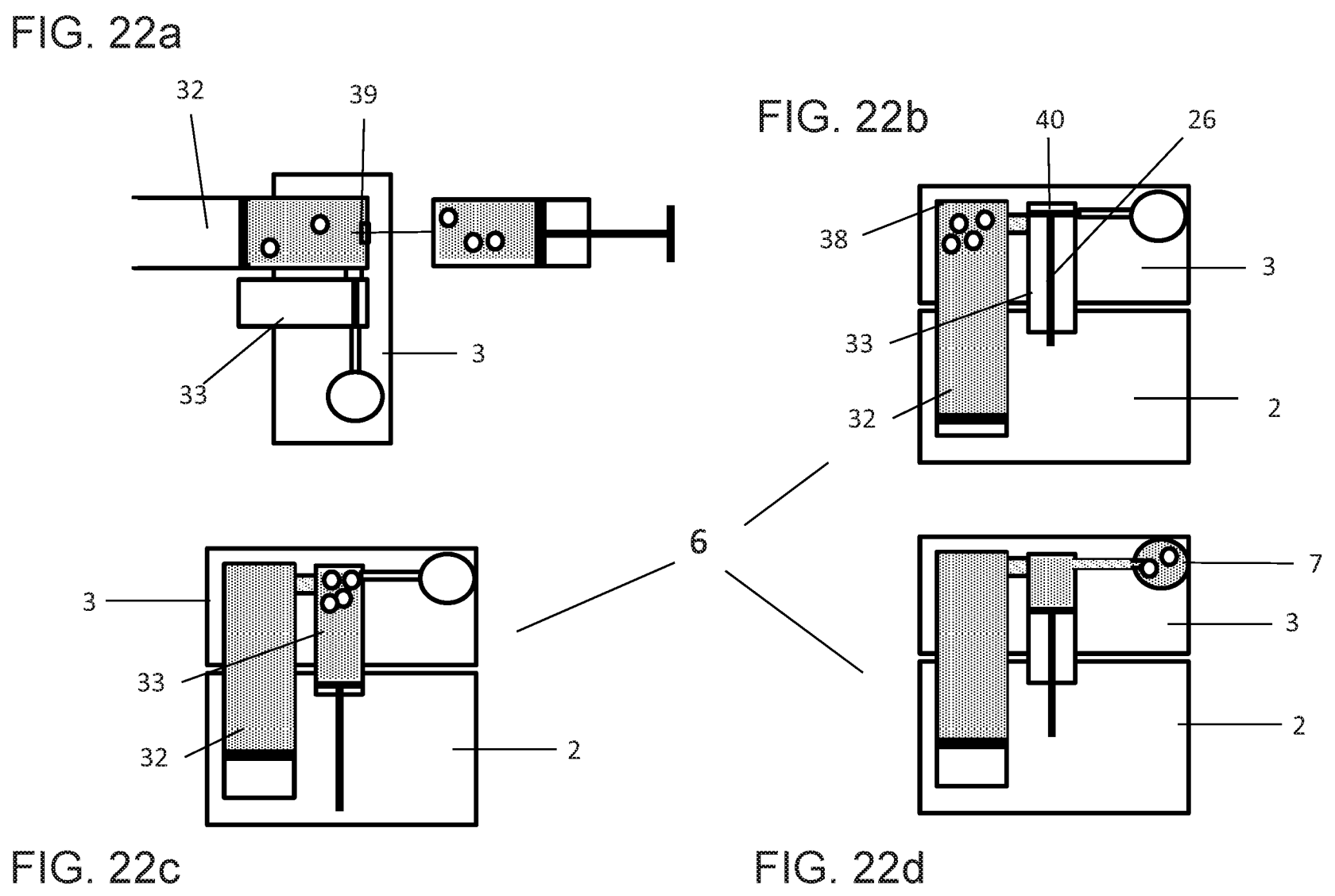

With reference to FIGS. 22A-D, in some embodiments, schemes of the priming process are shown. FIG. 22a shows reservoir 32 filling with external syringe. Patient holds DP 3 and aligns the syringe needle with opening 39. During fluid movement from syringe to reservoir, air bubbles are formed and randomly spread within reservoir 32. Next, the patient connects RP 2 and DP 3 and holds pump 6 in an upright position (FIG. 22b). In this position, air bubbles are gathered at the upper side of reservoir 32. Next, the patient operates pump 6 in a "priming mode" (i.e. command with remote controller). At the priming mode, the operation of the motor (not shown) automatically drives rod 26 and doser plunger 40 backward and forward at a pre-programmed sequence (or manually upon patient's discretion). The next priming step is shown in FIG. 22c. Doser 33 pumps fluid and bubbles from the upper part of reservoir 32 (second reservoir end 38) into the upper part of doser 33 (doser plunger 40 moves backward). Finally, fluid with bubbles is discharged from doser 33 into exit port 7 and further away drips externally (doser plunger 40 moves forward). The priming process may be repeated as much as needed until air bubbles are not seen. In some embodiments of the present disclosure, once the user visually inspects steady fluid flow through exit port 7 the pump may be instructed to end the priming sequence. RP 3 and reservoir 32 may be made of translucent plastic in order to make air bubbles visible. Sensors disposed between doser 33 and exit port 7 may also detect the presence or absence of bubbles (detailed in FIG. 31), and transmit a priming termination sequence whenever the absence of bubbles is detected. Once the termination sequence is ended, pump 6 is ready to use.

Figures 23A, 23B, 23C:
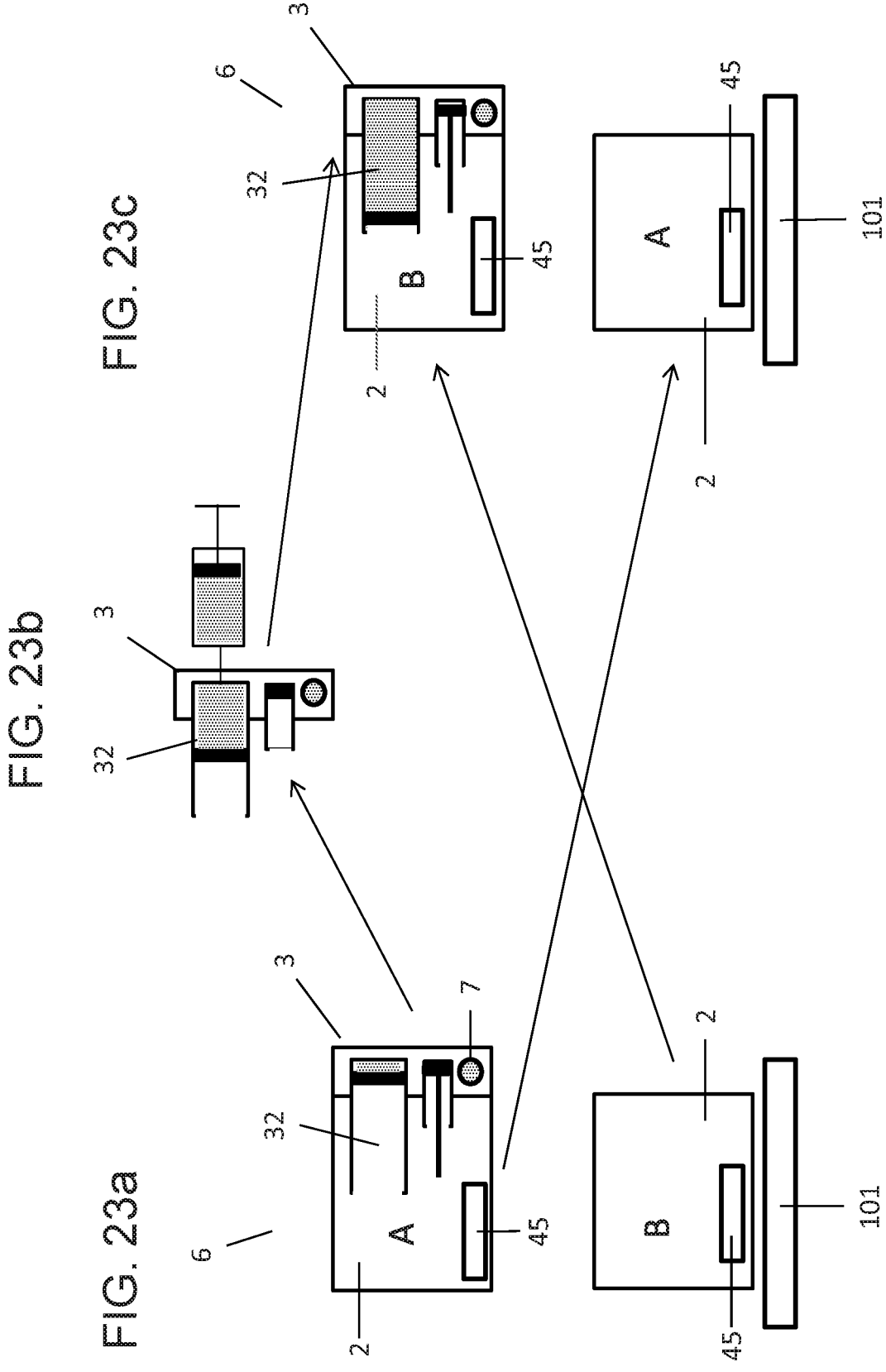
FIGS. 23A-C show method of battery exchange and reservoir refilling, according to some embodiments.

With reference to FIGS. 23A-C, in some embodiments, a method of battery exchange and reservoir refilling is shown. According to some embodiments of the present invention, duration use of the device may be extended at the patient's discretion while maintaining the small size of the device. In addition to increased patient comfort, this configuration saves money because less single-use pieces are disposed. Diabetes patients using durable (pager) or patch insulin pumps usually replace the infusion set or the entire pump every 2-3 day. There are mainly two parameters that limit the duration of pump use—the volume of the reservoir (amount of insulin units) and battery life time. Extension of pump operation time requires large reservoir and large battery, both of which enlarge pump volume. Device 1 is small and may be used for many days because the reservoir may be refilled and the battery may be replaced. Thus reservoir and battery volumes may be minimal. Patients may decide if they want to refill the reservoir, replace the battery or concomitantly do both. For example, in a current patch pump, the reservoir volume is 200 U and battery life time is 3 days. If the patient's total daily dose (TTD) is 100 units (U) then the patch pump should be replaced every 2 days (end of reservoir volume limitation). If the patient's TTD is 50 U then the patch pump should be replaced every 3 days (end of battery life limitation). In device 1, for example, reservoir volume is 100 U and battery life time is 1 day (smaller volumes than current pump), patient refills reservoir and replaces battery every 1 day as long as he/she wishes (for example, 1 week).

FIG. 23*a* shows pump 6 that comprise RP 2 (A) and DP 3. Battery 45 resides within RP 2. In this example, reservoir 32 is almost empty and should be refilled. Meanwhile, battery 45 of a second RP 2 (B) is being charge by inductive charger 101. When reservoir 32 is almost empty (patient receives "low reservoir" alert), the patient disconnects pump 6 from cradle and then disconnects RP 2 (A) from DP 3 (not shown). FIG. 23*b* shows refilling of reservoir 32 of DP 3 with external syringe. After reservoir 32 is filled, the patient reconnects DP 3 and a second RP 2 (B) that comprises the charged battery 45. Pump 6 is ready for another cycle of use (FIG. 23*c*). Battery 45 of first RP 2 (A) may then be recharged by charger 101 to be ready for the next cycle of use.

Figure 24C:
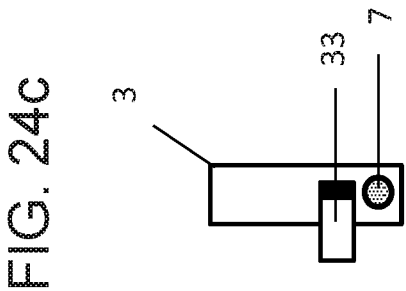
FIGS. 24A-F show schemes of a method for extension device duration of use, according to some embodiments.
Figure 24F:
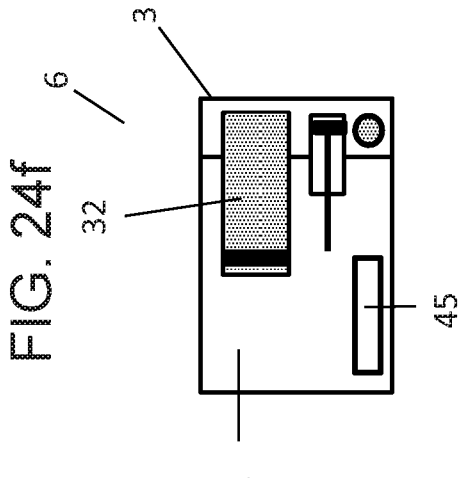
Figure 24B:
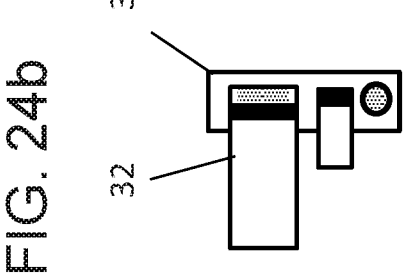
Figure 24E:
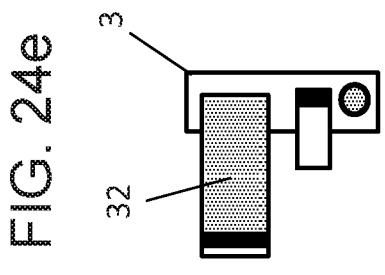
Figure 24A:
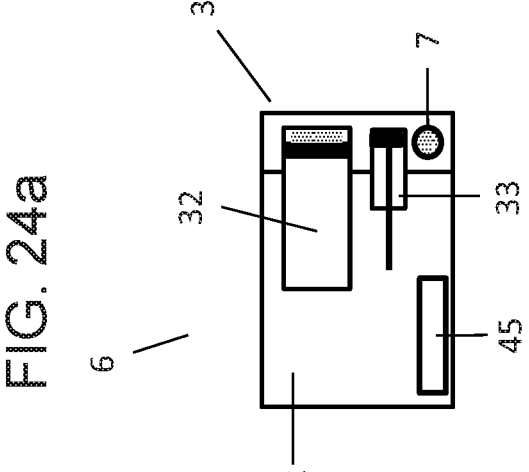
Figure 24D:

With reference to FIGS. 24A-F, in some embodiments, schemes of a method for extending the device's duration of use are shown. In this embodiment the reservoir is prefilled (by patient or manufacturer). The empty reservoir is replaced by a prefilled reservoir and the pump may be used again until the replaceable reservoir is empty. FIG. 24*a* shows device 6 that comprises RP 2 and DP 3. Reservoir 32 is reversibly disposed within DP 3. In this example, reservoir 32 and doser 33 are empty and the patient receives "end of reservoir" alert. Patient disconnects pump 6 from cradle (not shown) and disconnect RP 2 from DP 3 (not shown). FIG. 24*b* shows DP 3 that comprises empty reservoir 32. FIG. 24*c* shows DP 3 after removal of detachable reservoir. FIG. 24*d* shows a few prefilled reservoirs 32. These reservoirs may be filled by the patient in advance and can be stored in a refrigerator. Alternatively the reservoirs may be filled by the manufacturer as prefilled cartridges (vial). Reservoirs may be made of polymer (plastic) or glass. FIG. 24*e* shows DP 3 with prefilled reservoir 32 reassembled in DP 3. At the final step (FIG. 24*f*), the patient connects DP 3 (with filled reservoir) with RP 2 (battery 45 recharged), and pump 6 is ready for another cycle of use.

Figure 25:
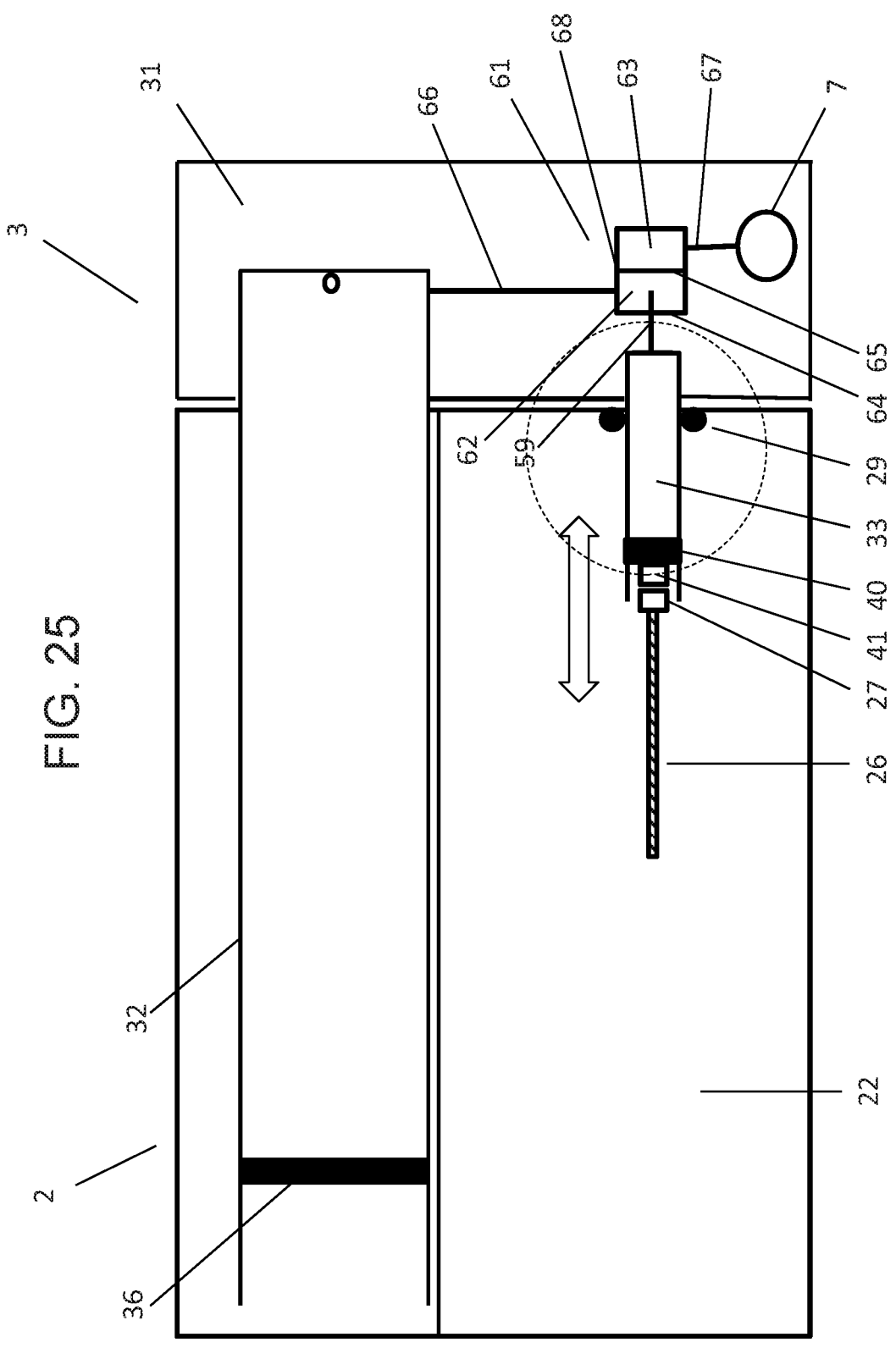
FIG. 25 show a scheme of an active valve system, according to some embodiments.

With reference to FIG. 25, in some embodiments, a scheme of an active valve system 61 is shown. In this embodiment doser 33 is floating (hereinafter "floating doser" 33) and may be moved forward and backward due to friction force between doser plunger 40 and floating doser 33. RP 2 is connected with DP 3 and rod 26 is coupled with doser plunger 40 by coupling means 27 and 41. Doser 33 resides within RP 2 and gasket 29 provides sealing of compartment 22. Doser plunger 40 moves forward or backward according to forward or backward linear movement of rod 26. Doser 33 may linearly move forward and backward (double arrow) relatively to gasket 29. DP 3 comprises base 31, reservoir 32, reservoir plunger 36, doser 33, active valve system 61, conduits 66 and 67, and exit port 7. Doser 33 comprises plunger 40, plunger coupling means 41, and sliding needle port 59 which is a hollow needle disposed at the distal end of doser 33 and provides an exit port of fluid from doser (hereinafter a "sliding needle"). Active valve system 61 is rigidly connected to base 31. Active valve system 61 comprises first conduit 66, second conduit 67, and dual chamber 68. Dual chamber 68 comprises first septum 64, first chamber 62, second septum 65, and second chamber 63. Conduit 66 establishes fluid communication between reservoir 32 and first chamber 62. Second conduit 67 establishes fluid communication between second chamber 63 and exit port 7. Both first septum 64 and second septum 65 are configured to prevent fluid leakage when punctured by sliding needle 59. Both first septum 64 and second septum 65 self-seal upon needle withdrawal from septum puncture site. First septum 64 and second septum 65 may each be made, for example, of a plastic, such as silicone.

FIG. 25*a* (1-2) shows an enlarged scheme of an example embodiment depicted in dotted circle of FIG. 25. DP 3 includes base 31 and cylindrical extension 31', doser 33, doser plunger 40 and sliding needle 59. RP 2 includes gasket 29. Doser 33 freely moves within cylinder 31' (directions of arrow). When RP 2 is connected with DP 3, cylinder 31' transverses gasket 29 and the tight junction between cylinder 31' and gasket 29 provides sealing of RP2 sealed compartment 21. When plunger 40 moves forward or backward, doser 33 freely follows the direction of movement because the friction between doser 33 and doser plunger 40 is much higher that the friction between doser 33 and cylinder 31'. FIG. 25*b* (2) shows a cross section view of plan X-X of FIG. 25*a* (1). Gasket 29 tightly encircles cylinder 31' and doser 33 may freely move backward and forward within cylinder 31'.

Figures 26A, 26B:
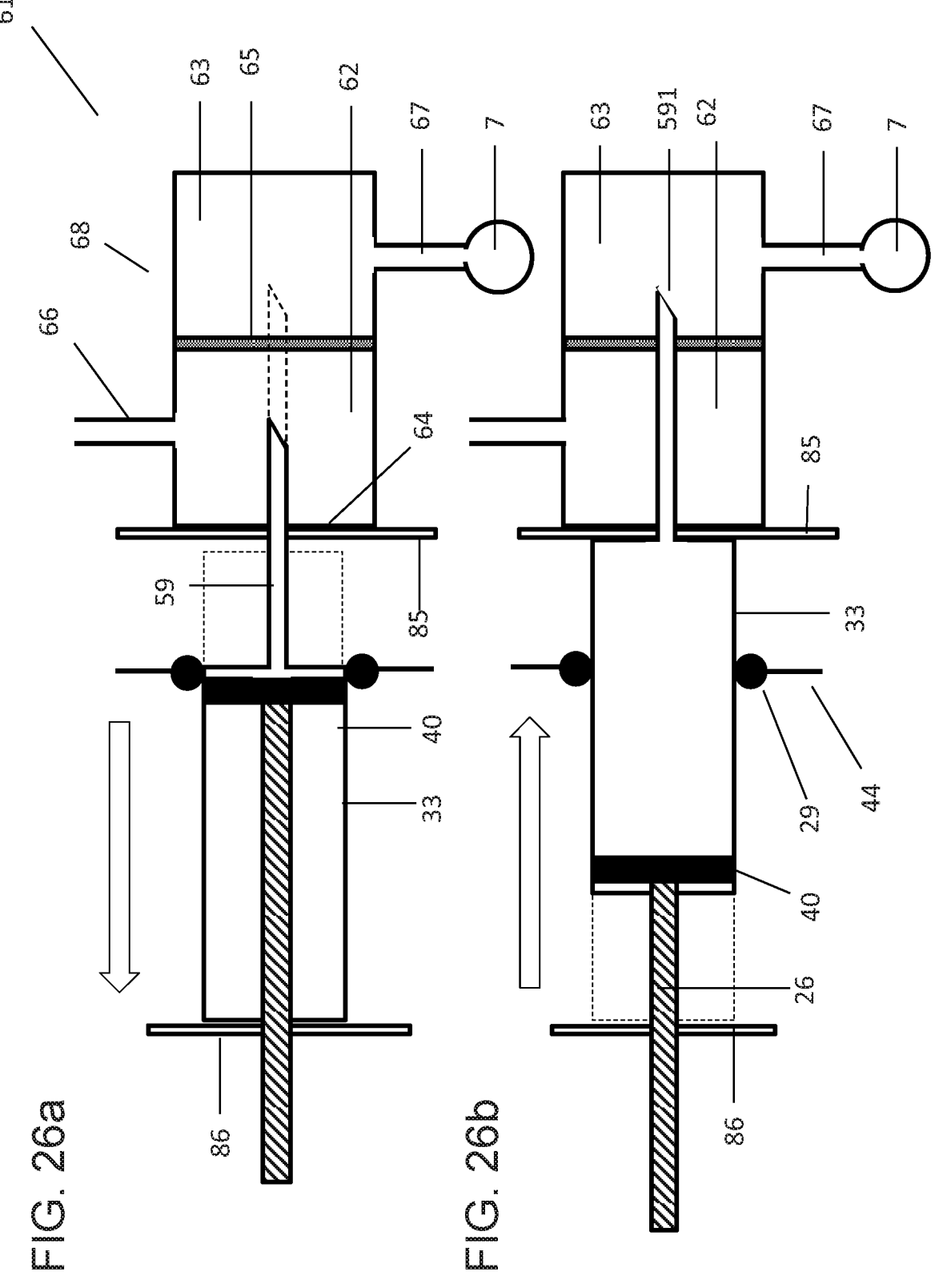

With reference to FIGS. 26A-B, in some embodiments, an enlarged scheme of active valve system 61 is shown. Active valve system 61 includes dual chamber 68 that comprises first septum 64, first chamber 62, second septum 65, second chamber 63, conduits 66 and 67, and exit port 7. Floating doser 33 may move linearly forward and backwards (arrows) between stopper 86 (rigidly connected to RP) and stopper 85 (rigidly connected to DP). Floating doser 33 is rigidly connected to sliding needle 59. FIG. 26*a* shows the active valve system during backward motion of rod 26 and doser plunger 40 (toward the left, as shown by arrow). Due to friction force between floating doser 33 and doser plunger 40, floating doser 33 moves backward (left), relatively to gasket 29, from maximal forward position at stopper 85 (dotted line) to maximal backward position at stopper 86. During backward motion of floating doser 33, sliding needle 59 moves backward and tip of sliding needle 591 moves from second chamber 63 (dashed needle) to first chamber 62. During this phase, plunger 40 and floating doser are temporarily fixed and are moving together (e.g., little or no relative motion between floating doser 33 and plunger 40). When floating doser 33 touches stopper 86, there is no more relative motion between floating doser 33 and gasket 29, at that point, continuous backward motion of plunger 40 sucks fluid from reservoir 32 (not shown) through conduit 66 into first chamber 62 and floating doser 33 is filled. FIG. 26b shows the active valve system during forward motion of rod 26 and doser plunger 40 (toward the right, as shown by arrow). Floating doser 33 moves forward (right) relatively to gasket 29, from maximal backward position at stopper 86 (dotted line) to maximal forward position at stopper 85. During forward motion of floating doser 33, sliding needle 59 moves forward and tip of sliding needle 591 moves from first chamber 62 to second chamber 63. During this phase, plunger 40 and floating doser 33 are temporarily fixed to each other and are moving together (e.g., little or no relative motion between floating doser 33 and plunger 40). When floating doser 33 touches stopper 85, there is no more relative motion between floating doser 33 and gasket 29. At that point, continuous forward motion of plunger 40 pushes fluid from doser 33 through conduit 67 into exit port 7.

Figures 27A, 27B, 27C, 27D, 27E, 27F:
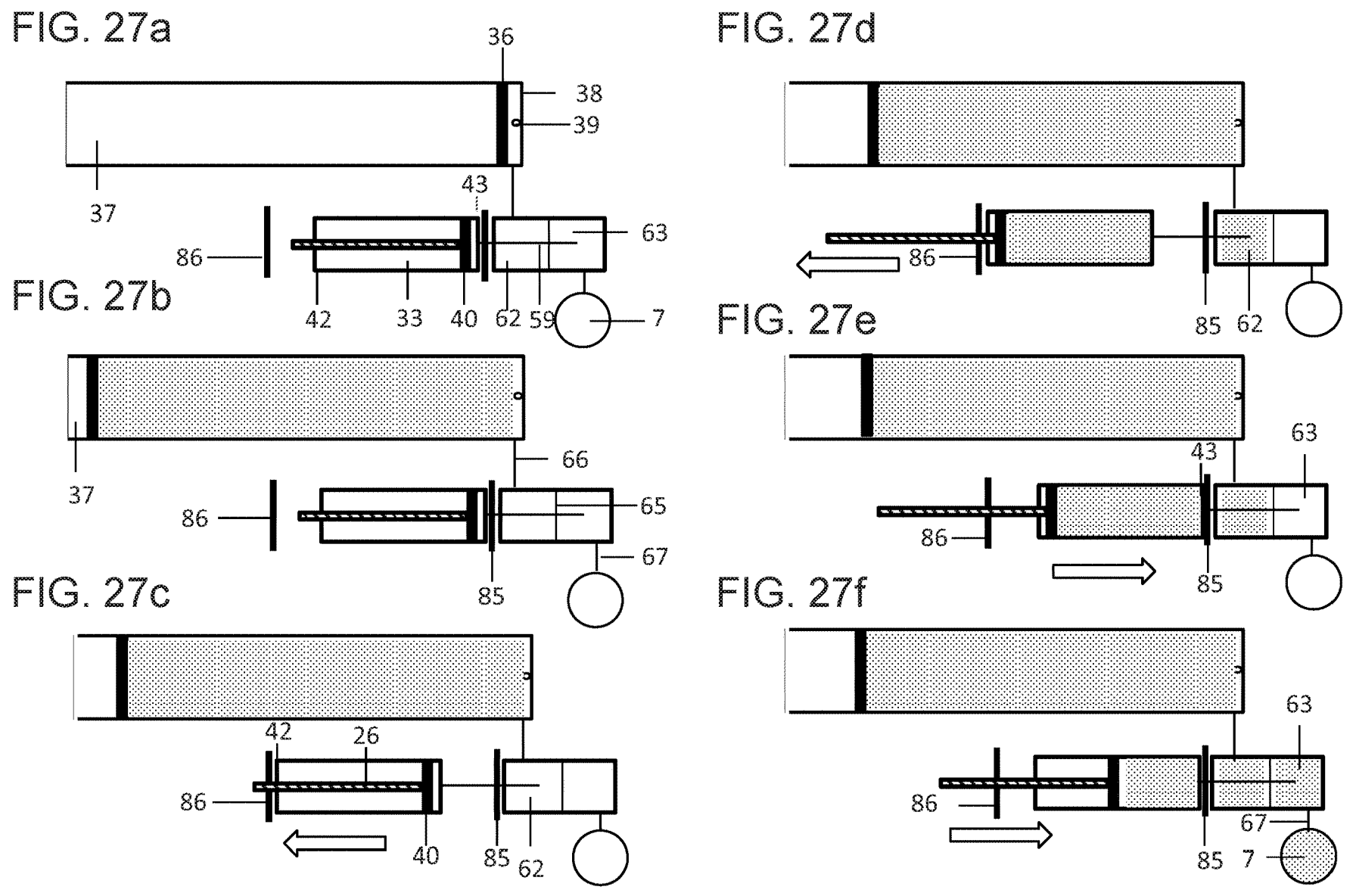

With reference to FIGS. 27A-F, in some embodiments, schemes of a pumping mechanism employing an active valve system are shown. For ease of understanding, only those components of the pumping mechanism that come in contact with the infusion fluid are depicted. FIG. 27a shows the initial state of the pumping mechanism before reservoir 32 is filled with infusion fluid. Reservoir plunger 36 is situated near second reservoir end 38, with filling port 39 disposed between plunger 36 and end 38. Doser plunger 40 is situated near second doser end 43. Second end of floating doser 33 is in physical contact with stopper 85. The tip of sliding needle 59 is situated in second chamber 63. FIG. 27b shows the state of pumping mechanism immediately after reservoir 32 is filled with infusion fluid. Infusion fluid is injected into reservoir 32 through filling port 39 using, for example, a syringe. The infusion fluid fills reservoir 32, displacing plunger 36 in the direction of first opening 37 of reservoir 32. The fluid may also fill first chamber 62 through first conduit 66. Fluid is prevented from flowing from first chamber 62 to second chamber 63 (and beyond) by septum 65. Filling concludes when, for example, plunger 36 reaches a stopper (not shown) situated near opening 37. FIG. 27c shows the state of pump mechanism when motor (not shown) is operated and rod 26 linearly moves in backward direction (to the left as shown by arrow). During this phase, floating doser 33 moves backward (left) with little or no relative motion between floating doser 33 and plunger 40. At the end of this phase first end of doser 42 is in physical contact with stopper 86 and sliding needle tip is situated in first chamber 62. FIG. 27d shows the state of the pumping mechanism when rod 26 and plunger 40 are moving backward (left as shown by arrow) and first chamber 62 and doser 33 are filling with fluid. During this phase, floating doser 33 is not moving and there is a relative motion between plunger 40 and doser 33. FIG. 27e shows the state of the pumping mechanism when motor (not shown) rotation is reversed and rod 26 linearly moves forward (to the right as shown by arrow). During this phase, floating doser 33 moves forward (right) with little or no relative motion between floating doser 33 and plunger 40. At the end of this phase second end of doser 43 is in physical contact with stopper 85 and sliding needle tip is situated in second chamber 63. FIG. 27f shows the state of the pumping mechanism when rod 26 and plunger 40 are moving forward (to the right, as shown by arrow) and fluid is delivered through second chamber 63 and conduit 67 into exit port 7. During this phase, floating doser 33 is not moving and there is a relative motion between plunger 40 and floating doser 33.

Figures 28A, 28B:
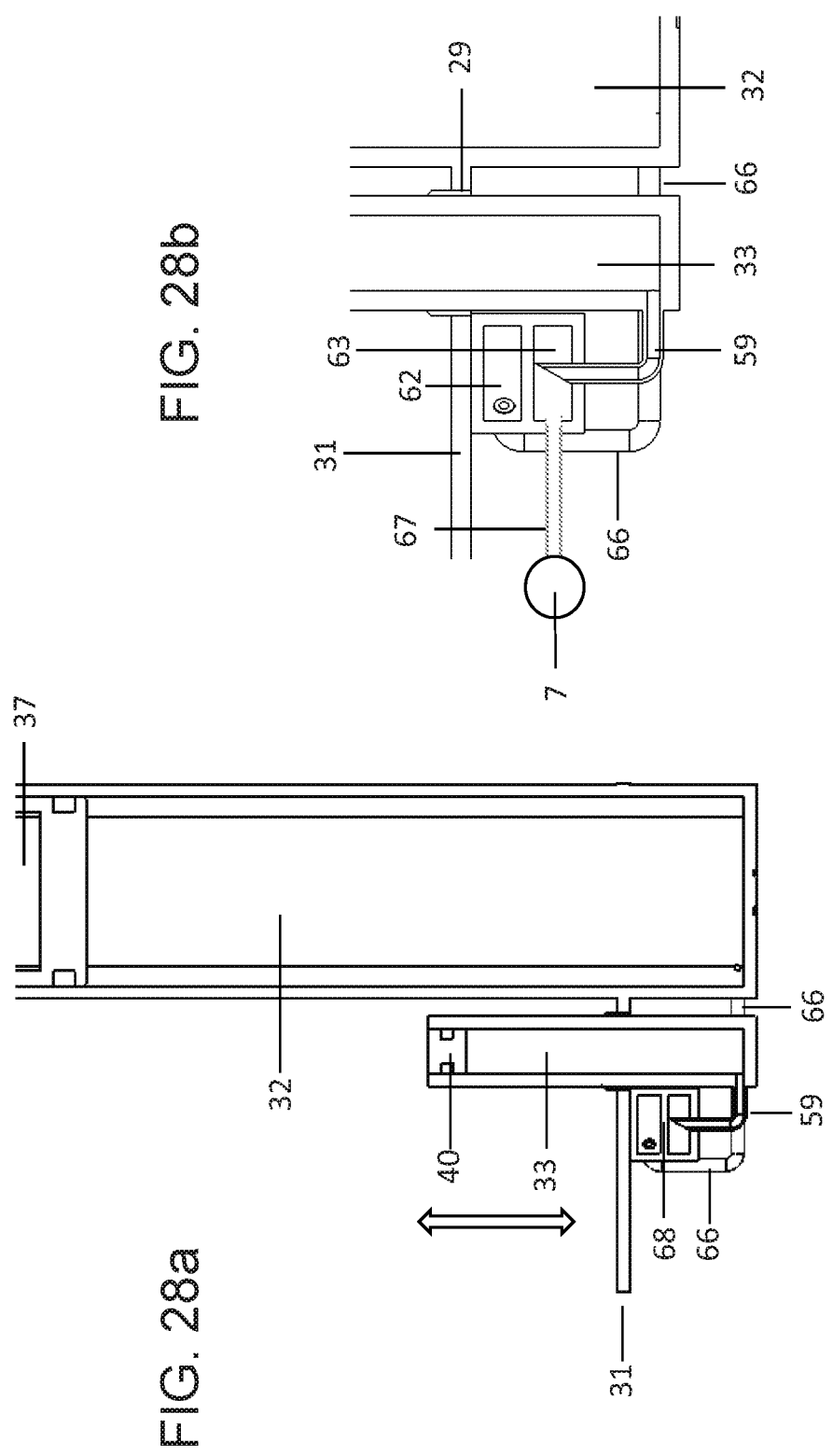
FIGS. 28A-B show cross section views, including a magnified view (B) of active valve system, according to some embodiments.

With reference to FIGS. 28A-B, in some embodiments, cross sectional views of an active valve system are shown. In this configuration, dual chamber 68 is positioned side by side with floating doser 33 and sliding needle 59 is curved. Dual chamber 68 is rigidly connected to base 31 and comprises first chamber 62 and second chamber 63. Conduit 66 is hydraulically connected with reservoir 32 and first chamber 62. Conduit 67 is hydraulically connected with second chamber 63 and exit port 7. Floating chamber 33 can move forward and backward (up and down, as shown by double arrow) relatively to base 31 and gasket 29. Sliding needle 59 is curved and hydraulically connected with floating doser 33 and second chamber 63. Upon backward and forward linear movement of plunger 40 (directions of arrow), floating doser 33 and sliding needle 59 are moving in the same direction of plunger 40. Accordingly, sliding needle tip moves forward or backward in the same direction of floating doser 33 and convertibly resides in first chamber 62 or in second chamber 63.

Figures 29A, 29B, 29C:
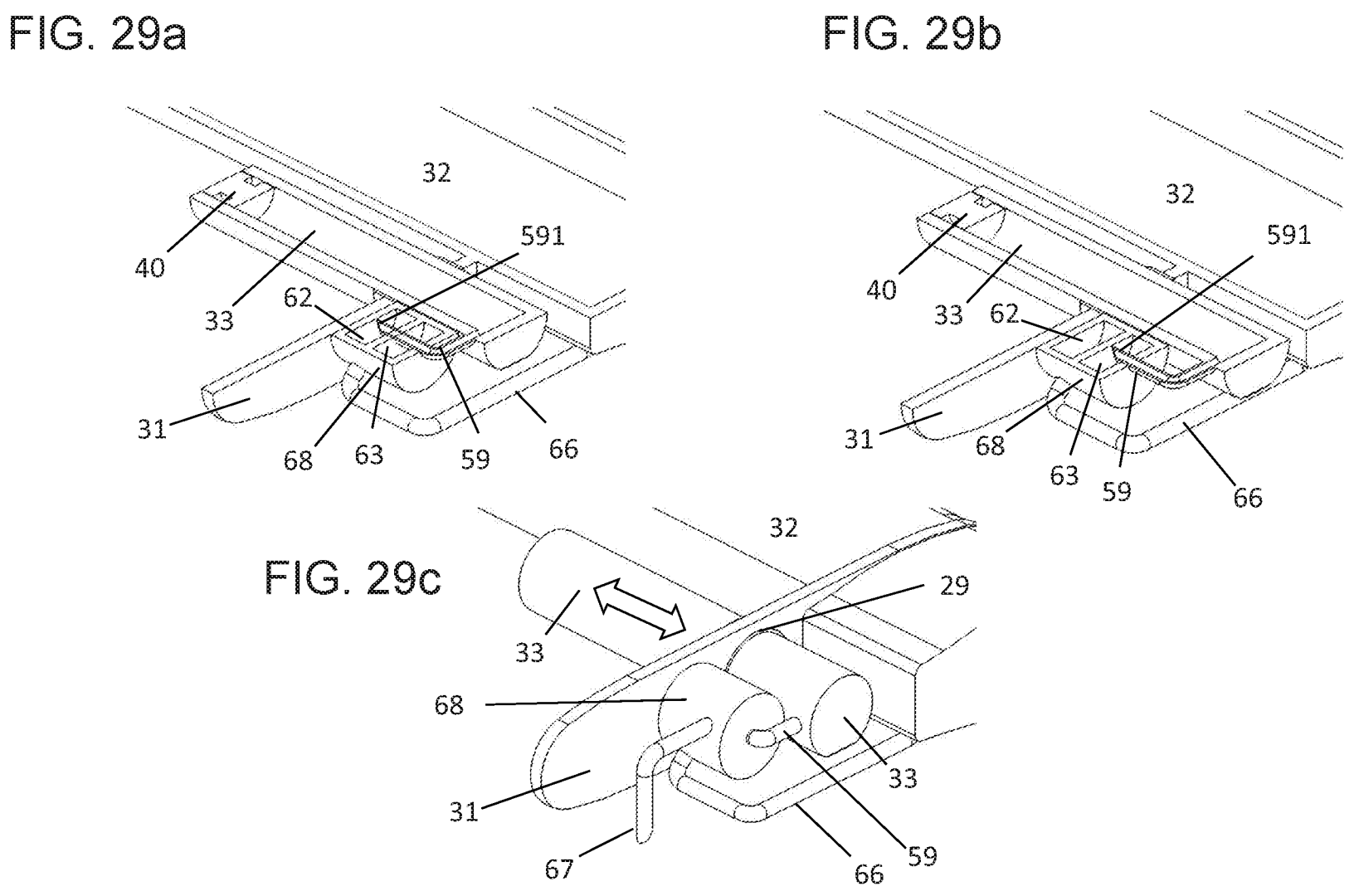

With reference to FIGS. 29A-C, in some embodiments, cross sectional (29a-b) and spatial (29c) views of the active valve system of FIG. 28 are shown. Dual chamber 68 is rigidly connected to base 31 and comprises first chamber 62 and second chamber 63. Conduit 66 is hydraulically connected with reservoir 32 and first chamber 62. Conduit 67 is hydraulically connected with second chamber 63 and exit port (not shown). FIG. 29a and FIG. 29b show the two optional positions of sliding needle tip 591. In FIG. 29a tip 591 resides in first chamber 62 and in FIG. 29b tip 591 resides in second chamber 63. FIG. 29c shows a floating doser 33 that linearly moves (direction of double arrow) in relative motion to base 31 and gasket 29. Accordingly sliding needle 59 linearly moves in relative motion to dual chamber 68.

Figures 30A, 30B:
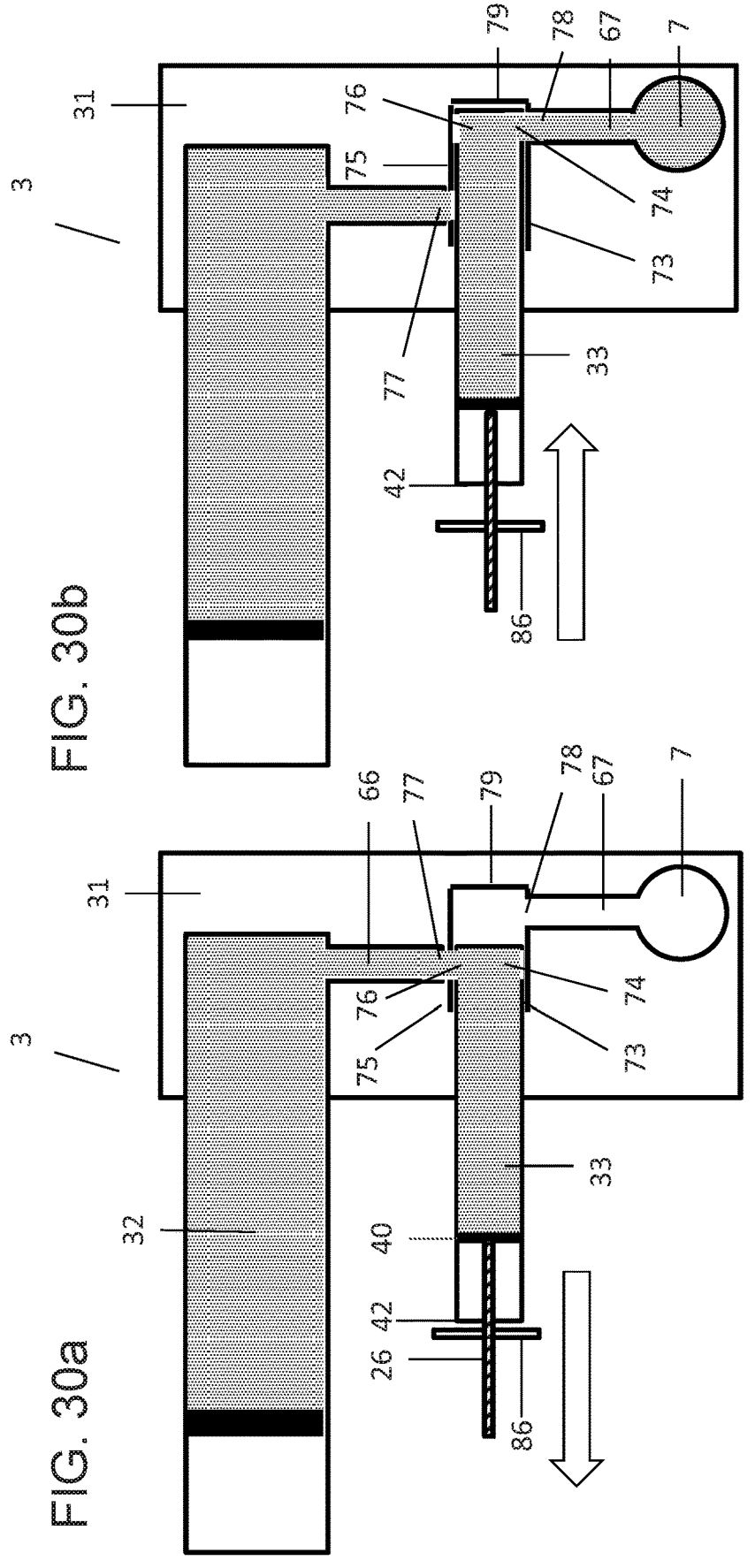
FIGS. 30A-B show schemes of an active valve system, according to some embodiments.

With reference to FIGS. 30A-B, in some embodiments, schemes of some embodiments of an active valve system are shown. In this configuration, floating doser 33 has two openings 74 and 76 (unlike one opening shown in configuration of FIG. 28). DP 3 comprises base 31, reservoir 32, floating doser 33, cylinder 79, conduits 66 and 67, and exit port 7. Floating doser 33 includes two openings 74 and 76, and cylinder 79 includes two openings 77 and 78. Floating doser 33 may move linearly (forward and backward in the direction of arrows) within cylinder 79 according to the direction of movement of plunger 40 and rod 26 (due to friction forces between plunger 40 and doser 33). The concept of the pumping mechanism is similar to FIG. 15, a backward motion of plunger 40 pumps fluid from reservoir 32 and fills doser 33 and a forward motion of plunger 40 dispenses fluid from doser 33 to exit port 7. FIG. 30a shows the process of doser 33 filling. Initially, backward movement (to the left, as shown by arrow) of floating doser 33 aligns opening 76 and opening 77 (opening 74 is closed). When doser end 42 touches stopper 86, further backward movement of plunger 40 pumps fluid from reservoir 32 into doser 33. FIG. 30b shows the process of fluid dispensing from doser 33. Initially, forward (to the right, as shown by arrow) movement of floating doser 33 aligns opening 74 and opening 78 (opening 74 is closed). When doser 33 touches cylinder 79, further forward movement of plunger 40 dispenses fluid from doser 33 into exit port 7. Subsequently, when doser 33 is empty, plunger 40 moves backward and another cycle of doser filling is initiated.

Figure 31:
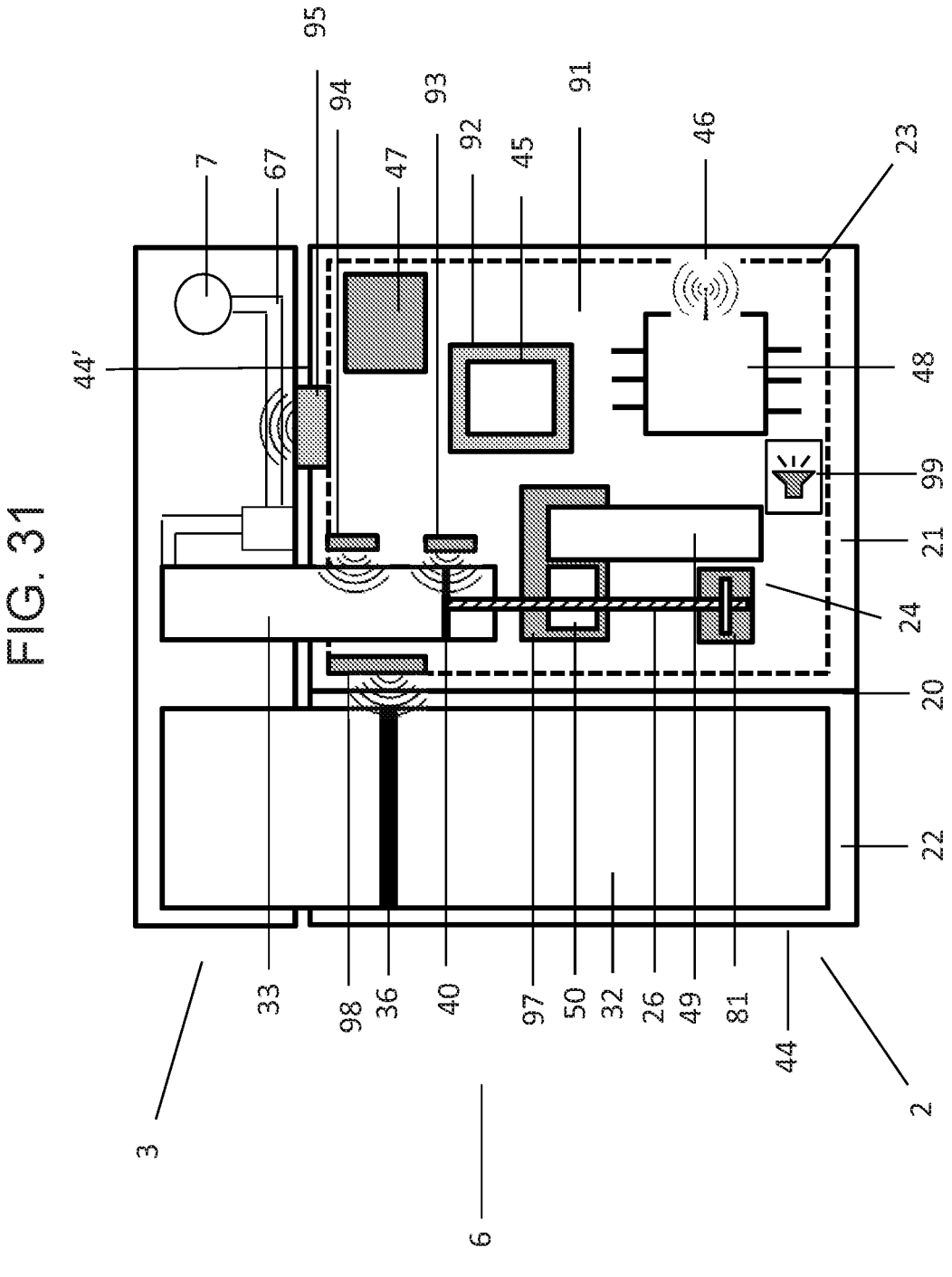
FIG. 31 shows a scheme of pump electronic module and actuation module, according to some embodiments.

With reference to FIG. 31, in some embodiments, a scheme of electronic module 23 and actuation module 24 of pump 6 is shown. Pump 6 comprises RP 2 and DP 3. RP 2 comprises a shell 44 and a septum 20 that divides RP 2 into two separate compartments, sealed compartment 21 and vented compartment 22. Septum 20 and shell 44 may be partially or totally transparent. In some embodiments, septum 20 and shell wall facing DP 44' include transparent windows providing line of site between sealed compartment 21 and reservoir 32, and between sealed compartment 21 and DP 3. DP 3 comprises reservoir 32, reservoir plunger 36, doser 33, doser plunger 40, conduit 67 and exit port 7 (other components of DP 3 are not shown). When DP 3 and RP 2 are connected (forming pump 6), reservoir 32 resides within vented compartment 22 and doser 33 resides within sealed compartment 21. Electronic module 23 (dotted line) comprises power source (battery) 45, processor 48, transceiver 46, buzzer 99, and sensors—acceleration sensor (accelerometer) 47, low battery sensor 92, air bubbles sensor 95, revolution sensor 81, occlusion sensor 97, low reservoir sensor 98, and doser plunger position sensors 93 and 94. Actuation module 24 comprises motor 49, gear 50, and rod (drive screw) 26. Power source 45 may be a single use battery or a rechargeable battery. In some embodiments of the present disclosure, power source 45 is rechargeable and recharging may be implemented in contactless fashion. For example, power source 45 may be recharged using an inductive mechanism. In some embodiments of the present disclosure, power source 45 is rechargeable and recharging may be implemented by providing electrical contacts that traverse shell 44 of RP 2. Power source 45 may provide power to any of the components of electronics module 23 and actuation module 24. Transmitter/receiver 46 may be, for example, a wireless transmitter/receiver. In some embodiments of the present disclosure, transmitter/receiver 46 may be a Bluetooth radio and more specifically, transmitter/receiver 46 may be a low energy Bluetooth (BLE) radio. Accelerometer 47 may be a sensor configured to measure the acceleration applied to pump 6 on all three physical axes (x, y, and z). In some embodiments of the present disclosure, accelerometer 47 may measure gravitational acceleration, whereas in other embodiments according to the present disclosure accelerometer 47 may not measure the force of gravity. In some embodiments according to the present disclosure accelerometer 47 may measure the rate of rotation of pump 6 around each of the three physical axes. Accelerometer 47 is connected to processor 48 which can process acceleration data and calculate patient's energy expenditure (caloric consumption). Energy expenditure data is a major parameter in tailoring patient's insulin basal delivery rate, calculation of total daily, activity related, caloric consumption, and calculation of meal bolus delivery with bolus calculator. Accelerometer 47 may continuously monitor body movements and may be used as a first indicator for detection hypoglycemia during the night. In some embodiments of the present disclosure, accelerometer 47 can be used as a patient interface with pump 6. For example, instructions to microprocessor 48 may be provided by tapping on pump 6 and having certain tap sequences corresponding to certain instructions detected by accelerometer

Figure 34:
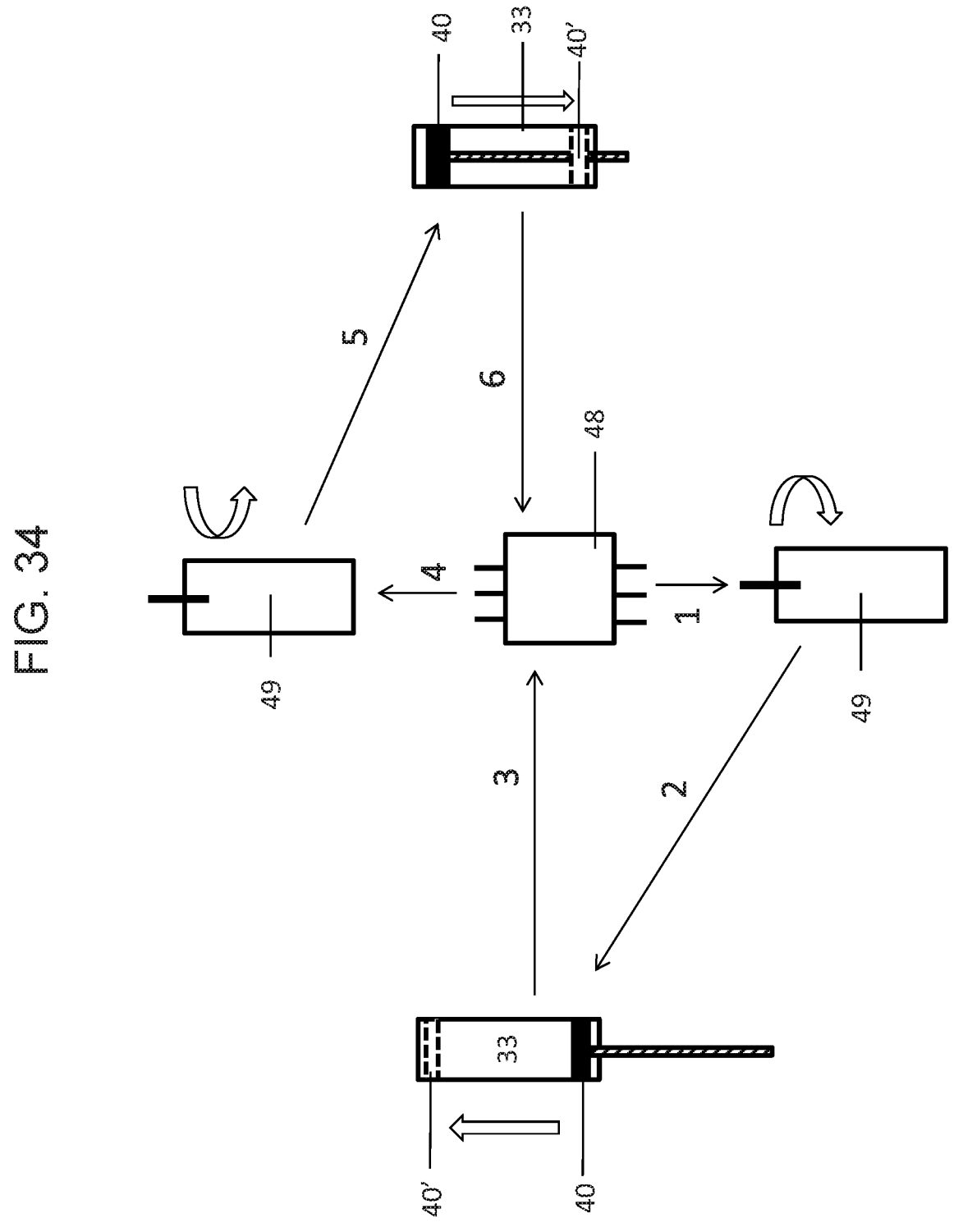
FIG. 34 shows a scheme of motor operation modes during the various phases of plunger movement and fluid dispensing, according to some embodiments.

47 and subsequently processed by the microprocessor. For example, in some embodiments in which the infusion fluid is insulin intended at providing glucose control in a diabetes patient, certain taps may correspond to insulin boluses of various sizes prior to meals. For example, if each tap is preprogrammed to 1 unit of insulin, administration of 6 units requires 6 taps. Microprocessor 48 may be a chip incorporating all functions of a computer's central processing unit on one or more integrated circuit. Microprocessor 48 may accept digital data from transmitter/receiver 46 and accelerometer 47. Microprocessor 48 may process inputs according to instructions stored in its memory, and provide results as output. Thus, inputs and outputs to and from microprocessor 48 may be to and from transmitter/receiver 46, accelerometer 47, buzzer 99, and sensors. Transmitter/receiver signals may originate in a remote controller, smartphone, and personal computer using RF radio communication protocol such as Bluetooth or a low energy Bluetooth. In some embodiments of the present disclosure, signals received at transmitter/receiver 46 may originate from a blood glucose meter, a continuous glucose monitor, or any physiological sensor which may be external to pump 6. Signals originating from sensors internal to pump 6 may be directly received in microprocessor 48. Outputs from microprocessor 48 may be signals directed to actuation module 24 and directed at causing rod 26 to advance or retract linearly. Outputs from microprocessor 48 may also be transmitted by transmitter/receiver 46 to external devices such as remote controllers, smartphones, personal computers, and servers. Microprocessor 48 may store in its memory computer programs directed at causing doser 33 to deliver infusion fluid in predetermined fashion. In some embodiments of the present disclosure, microprocessor 48 may store in its memory computer programs implementing closed loop control algorithms. Microprocessor 48 may receive and process inputs from various sensors that are embedded on printed circuit board (PCB) 91 at designated locations. Data received from sensors and processed by processor may be wirelessly transmitted through transceiver 46 to any remote controller/monitor (controller 200, smartphone 500, PC 600, etc.) and may be presented as alerts and/or alarms. Low battery sensor 92 alerts the patient to replace RP 2 before battery end of life. Upon receiving the alert, the patient should disconnect pump 6 from cradle 5, disconnect RP 2 and DP 3 and reconnect DP 3 and fully charged RP 2 as shown in FIG. 23. Revolution sensor 81 counts motor revolutions by any means known in the art, for example, two or more vanes rotating in between a light emitting diode (LED) and a photodiode. Revolution sensor 81 data (counting number of revolutions) is assessed by microprocessor 48, if there is a mismatch between programmed and real time revolution counting (i.e. missed pulses), patient receives alarm or alert (presented on any user interface). Mismatch (missing pulses) between processor commands and actual motor revolutions may be a consequence of stuck motor (i.e. breakage of a hinge or a gear) or high resistance to motor rotation (i.e. occlusion of fluid path). Occlusion sensor 97 detects torque between motor 49 and gear 50, and between gear 50 and rod 26 (driving screw). Increased torque in gear or motor can be caused by motor or gear malfunctions or increased resistance to motor operation due to occlusion in fluid flow path. Distinction between motor/gear malfunction and fluid path occlusion can be effected by the processor commanding backward motion of rod 26 (reversing motor direction of revolution (i.e. clockwise to counterclockwise), as shown in FIG. 34. If torque is increased due to gear or motor malfunction (i.e. hinge breakage) torque remains high at reversing motor direction of revolution. If torque is increased due to occlusion (high resistance), torque is decreased at reversing motor direction of revolution. Occlusion sensor 97 data is assessed by processor 48, transmitted to any user interface, and presented as occlusion alarm (warning). User operation at receiving occlusion warning is shown in FIG. 35). Plunger position sensors 93, 94, and 98 comprise LED and photodiode; the principle of operation is further detailed in FIG. 36. End of reservoir sensor 98 detects reservoir plunger 36 position when volume in reservoir 32 is low and reservoir 32 should be refilled (as shown in FIG. 23). In some embodiments, additional plunger position detectors may be provided alerting the patient when volume in reservoir reaches predetermined thresholds (i.e. decreasing insulin volumes— 100 U, 90 U, 80 U . . . until 20 U when reservoir should be refilled). In one embodiment a window (not shown) in septum 20 (dividing sealed 21 and vented 22 compartments of RP 2) provides a line of site between end of reservoir sensor 98 and reservoir 32. When plunger 36 reached end of volume position it is aligned with the window and disables light transmission through the window. Sensors 93 and 94 detect doser plunger 40 positions at start and end of plunger 40 movement within doser 33. Detailed description of operation modes of sensors 93 and 94 are further described in FIG. 36. Sensors 93 and 94 provide processor 48 with location of plunger 40 and accordingly controlling motor 49 direction of revolution and forward or backward motion of rod 26 as detailed described in FIG. 34. Air bubble sensor 95 detects air bubbles traveling in conduit 67 toward exit port 7. Air bubble sensor 95 may be operated with piezoelectric ultrasonic transducers. The measurement of the propagation time is based on alternate transmission and reception of ultrasonic pulses in and against the direction of flow. The sensor performs noncontact detection of air and gas bubbles in the liquid through the tube wall, and thus allows continuous quality monitoring. Two piezoelectric ultrasonic transducers work as transmitter and receiver. In another embodiment, air bubble sensor 95 is an optic sensor detecting light transmission through transparent conduit 67. In this configuration sensor 95 is facing a window (not shown) in the side of RP shell 44' facing DP 3.

Figure 32:
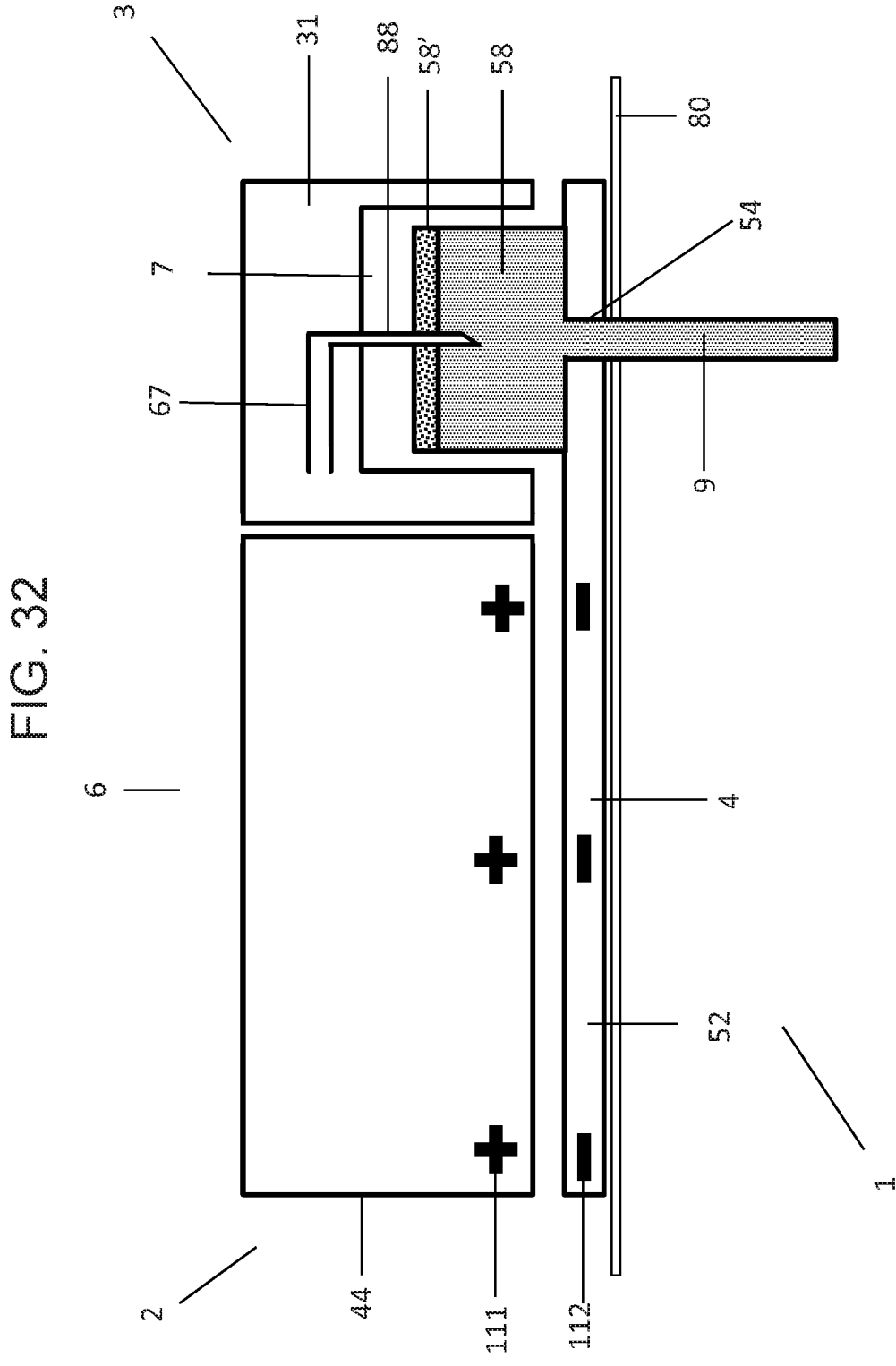
FIG. 32 shows a longitudinal cross section scheme of the device, according to some embodiments.

With reference to FIG. 32, in some embodiments, a longitudinal cross section of device 1 is shown. Pump 6 is comprised of RP 2 and DP 3. Pump 6 is connected to cradle 4 that adhere to patient skin 80. DP 3 includes base 31, exit port 7, conduit 67 and connecting needle 88. Member 58 including septum 58' is connected to cannula 9 that traverses cradle 4 through opening 54. Connecting needle 88 pierces septum 58' and resides within member 58 providing fluid communication between conduit 67 and cannula 9. Pump 6 may be connected to cradle 4 with a snap mechanism 8 as shown in FIG. 17. In some embodiments, cradle 4 is connected to pump with magnets 111, 112. Magnets 111 and 112 can resides in RP 2 or cradle 4 and a ferromagnetic member may be located on the other side interchangeably. Ferromagnetic member may be the RP 2 shell 44. Magnets within RP 2 may be a permanent magnets or electromagnets.

With reference to FIGS. 33A-B, in some embodiments, schemes of magnetic (33*a*) and mechanical (33*b*) reversible connections of rod 26 with doser plunger 40 are shown. During connection of RP 2 and DP 3, for example after refilling, rod 26 and plunger 40 should be engaged such that forward and backward linear motion of rod 26 moves plunger 40 and doser 33 as detailed in FIG. 26. FIG. 33*a* shows a scheme of magnetic connection between rod coupling means 27 and plunger coupling means 41. A Magnet may reside in both coupling means and a counter ferromagnetic member may reside in the opposite coupling means. FIG. 33*b* shows a scheme of mechanical connection, in this example a ball and socket mechanism. Rod coupling means 27 is reversibly engaged with plunger coupling means 41. A combination of mechanical and magnetic coupling means is also possible.

With reference to FIG. 34, in some embodiments, a scheme of motor 49 operation modes (1-6) during the various phases of plunger movement and fluid dispensing is shown. Upon command of processor 48 (1) motor 49 rotates in clockwise direction and causes via gear (not shown) a forward movement (direction of arrow) of plunger 40 (2). When plunger 40 reaches "end of doser point" 40' (detected by plunger position and/or rotation sensors (not shown) or calculated by an algorithm), processor 48 receives a signal (3) and commands motor 49 to reverse direction of rotation (counterclockwise) (4). Motor 49 rotation in a counterclockwise direction moves plunger 40 in a backward direction (arrow) (5). When plunger 40 reaches initial point 40', processor 48 receives a command to reverse direction of rotation (6) and the operation cycle restarts.

Figures 35A, 35B:
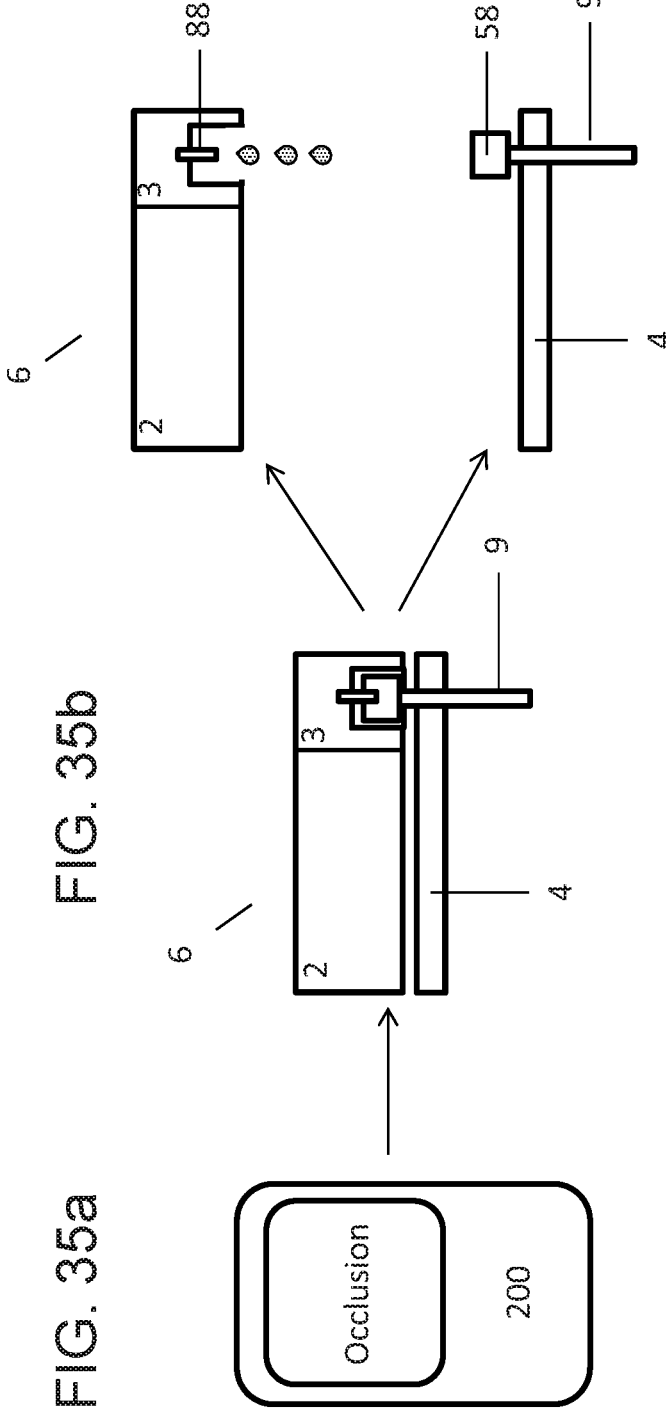
FIGS. 35A-B show a scheme of processes conducted by the patient upon receiving occlusion warning, according to some embodiments.

With reference to FIGS. 35A-B, in some embodiments, a scheme of processes conducted by the patient upon receiving occlusion warning is shown. Occlusion in fluid path can happen within the pump 6 (i.e. occlusion within conduits 66, and 67 shown in FIG. 25), or occlusion of cannula 9 (for example, in cases of cannula kinking or insulin crystallization). Cannula 9 occlusion requires replacement of cannula 9, cradle 4, and member 58. Occlusion of conduits within pump requires replacement of DP 3. When patient receives occlusion warning on controller 200 (FIG. 35*a*), pump 6 should be disconnected from cradle 4 and member 58 (FIG. 35*b*). When pump 6 is operated (i.e. small bolus administration) and there is no occlusion within pump, drops of fluids should be seen emerging from connecting needle 88 and occlusion warning should disappear. In this case, occlusion is within cannula 9 and accordingly, cradle 4, member 58, and cannula 9 should be replaced. If drops are not seen during pump operation and occlusion warning remains, occlusion is within pump and DP3 should be replaced.

Figures 36A, 36B:
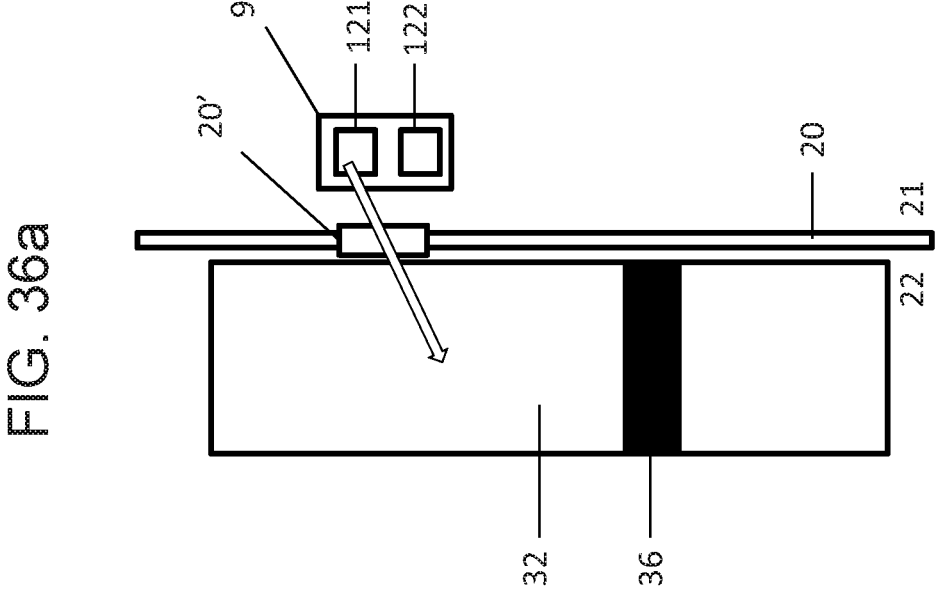
FIGS. 36A-B show schemes of end of reservoir sensor, according to some embodiments.

With reference to FIGS. 36A-B, in some embodiments, schemes of end of reservoir sensor 98 are shown. Sensor 98 detects plunger 36 position within reservoir 32. Septum 20 divides RP 2 into vented compartment 22 and sealed compartment 21. Septum 20 includes a transparent window 20' that provides line of site between the vented and sealed compartments. Reservoir 32 resides within vented compartment 22 and sensor 98 resides within sealed compartment 21. In one embodiment, end of reservoir sensor 98 includes a LED 121 and a photodiode 122. During pump operation reservoir 32 volume continuously decreases and plunger 36 passively moves forward. FIG. 36*a* shows the situation when plunger 36 is not aligned with window 20'. In this condition, light emitted from LED 121 transverses the transparent window 20' as shown by arrow. FIG. 26*b* shows the position of plunger 36 when reservoir replacement is indicated (preprogrammed by manufacturer or patients, for example when the remaining volume is 10 U of insulin). When plunger 36 is aligned with window 20', light emitted from LED 121 is reflected and detected by photodiode 122 (arrows). Accordingly the signal from the sensor goes to the processor, transmitted to the controller and presented to the patient as an end of reservoir alert. In some embodiments, sensor 98 may be comprised of piezoelectric ultrasonic transducers that work as transmitter and receiver. The position of doser plunger 40 may be detected by sensors 93 and 94 of FIG. 31 using the above mentioned light or acoustic detection means.

Figure 37:
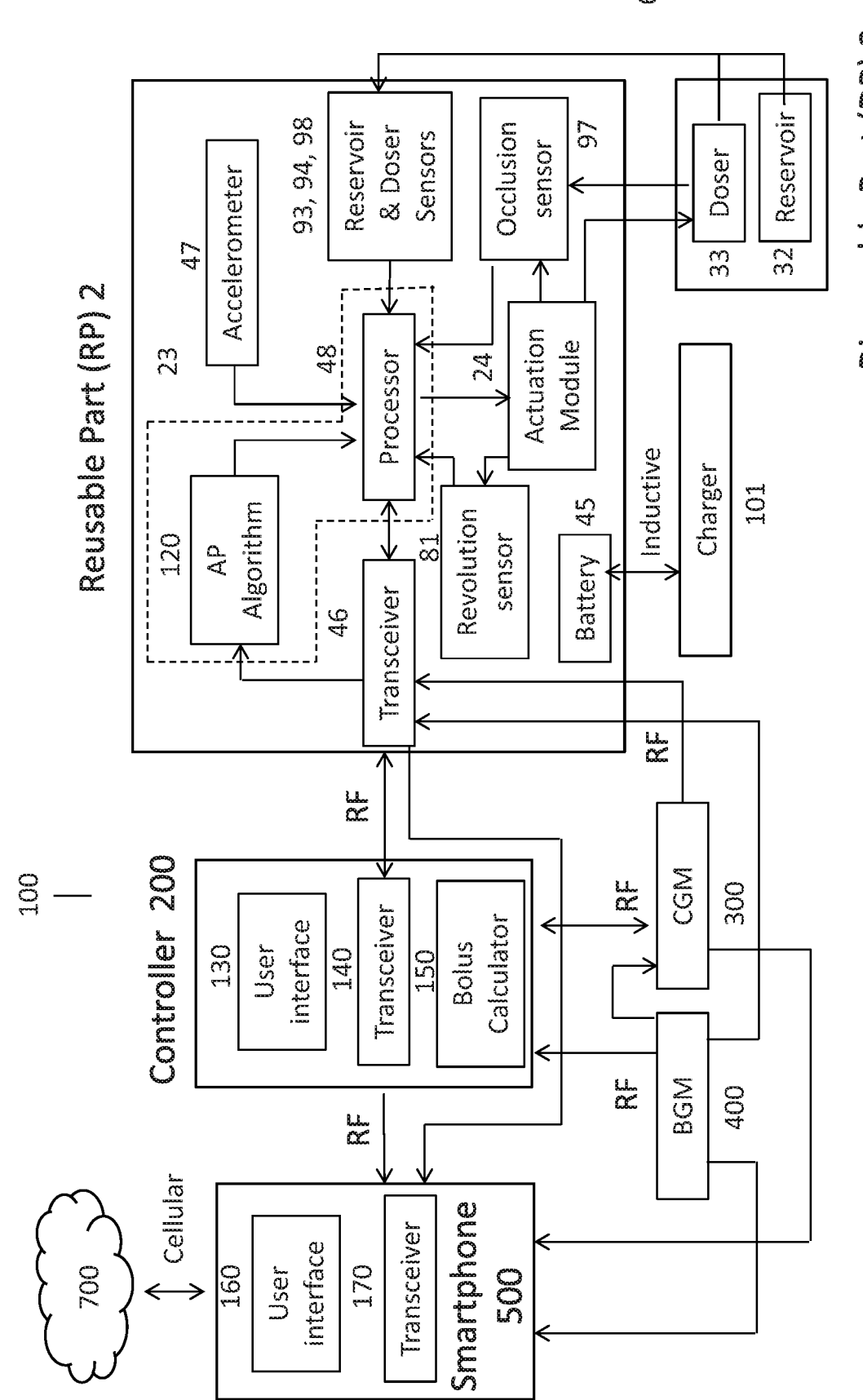
FIG. 37 shows a block diagram of diabetes management system, according to some embodiments.

With reference to FIG. 37, in some embodiments, a block diagram of diabetes management system 100 is shown. System 100 includes an infusion pump 6 that comprises a reusable part (RP) 2 and a disposable part (DP) 3 (when connected forming pump 6), charger 101, controller 200, smartphone 500, BGM 400, and CGM 300. BGM 400 and CGM 300 may function as standalone devices. CGM 300 may receive blood glucose readings directly from BGM 400 for calibrations. Controller 200 may be any electronic device that communicates with RP 2 in any proprietary or public RF communication protocol. In some embodiments, controller 200 is any electronic device that communicates with remote server (cloud communication) and RP 2. In this configuration, pump operation and personal data software may be downloaded from remote server and stored within any electronic device which becomes a controller 200 of RP 2. Smartphone 500 may be any electronic device that communicates with the controller in any proprietary or public RF protocol and has a cellular communication capability. RP 2 comprises electronic module 23 and actuation module 24. Electronic module 23 includes processor 48, transceiver 46, battery 45, accelerometer 47, reservoir and doser sensors 93, 94, 98, revolution sensor 81, buzzer and air bubbles sensors (not shown), and artificial pancreas (AP) algorithm 120 (resides within processor 48 as shown in dotted line). Battery 45 is recharged by induction using charger 101. Controller 200 includes a processor (not shown), user interface 130, transceiver 140, and bolus calculator 150. Controller 200 may include a microphone, a speaker, and a camera (not shown). Smartphone 500 includes user interface 160 and transceiver 170. In some embodiments, AP algorithm 120 may reside in controller 200, bolus calculator may reside in RP 2, or both may reside in controller 200 or RP 2. Reference is made now to RP 2. Processor 48 comprises a CPU, memory, operation software, and AP algorithm. Processor 48 receives inputs from accelerometer 47, sensors 93, 94, 97, 98, 81, CGM 300, BGM 400 and controller 200. Inputs to processor 48 from controller, CGM, and BGM are received via transceiver 46. Processor 48 outputs are commands to actuation module 24 and alerts, alarms, and log files via transceiver 46 to controller 200. Reference in now made to controller 200. Controller transceiver 140 has two way communication with RP 2, and CGM 300 and one way communication with BGM 400 (inputs) and smartphone 500 (outputs) using any RF communication protocol. User interface 130 may be touch screen, buttons, microphone, or camera. Patient's commands (i.e. insulin bolus, basal profile change, etc.) may be received by user interface 130 and transmitted via transceiver 140 to RP 2. Patient's commands may be transmitted to smartphone 500 and further on to remote viewer upon patient discretion (i.e. a child administers insulin and his/her parent receives the data, on-line, on parent's smartphone). Controller 200 may receive and present on-line and stored data from CGM 300 such as continuous glucose levels, alerts, alarms, and log files. Data from CGM may be used by bolus calculator 150. Controller 200 may transmit inputs to CGM 300, for example, blood glucose level received from BGM 400 for CGM calibration. Controller 200 may receive and present on-line and stored data from BGM 400 such as blood glucose levels, alerts, alarms, and log files. Data from BGM 400 may be used by bolus calculator 150. Bolus calculator 150 is software providing the patient with insulin bolus dose recommendations before meals. Bolus calculator software resides within controller processor (not shown). Inputs for bolus calculator include the following data points: carbohydrate content and glycemic index of the meal, and delivery pattern—received from patients through user interface, insulin on board (remaining insulin from previous bolus administration)—calculated by processor, blood glucose—received from BGM 400, and glucose level trends—received from CGM 300. Insulin sensitivity index and carb factor may be received from health care provider or patient through user interface 130 and can be stored within controller processor. If bolus calculator resides on RP 2 processor 48, all data received from user is transmitted from controller 200 to RP 2 and data points from BGM 400 and CGM 300 are transmitted directly to RP 2. Bolus calculation is done within processor 48. Reference in now made to smartphone 500. Smartphone comprises user interface 160 and transceiver 170. Smartphone 500 may receive inputs from RP 2, controller 200, CGM 300, and BGM 400. Inputs may be presented and/or transmitted to remote stations (i.e. family member, physician, etc.) via cellular protocol to cloud 700. In some embodiments (e.g., FIGS. 41-44), smartphone can be used as RP 2 controller. Reference is now made to operation modes of diabetes management system 100. In first operation mode ("manual"), pump 6 is programmed by patient with controller 200. Programing with controller 200 includes setting of basal delivery patterns and on demand bolus command. In second operation mode ("open loop system"), processor 48, via transceiver 46, continuously receives glucose readings from CGM 300 and accordingly adjusts operation of actuation module 24 and insulin administration from reservoir 32 and doser 33. In this operation mode, meal bolus commands set by patient are transmitted from controller 200 to processor 48 and accordingly processor 48 commands operation of actuation module 24 and insulin administration from reservoir 32 and doser 33. In third operation mode ("artificial pancreas" or "closed loop system, or "automated glucose control system"), controller 200 is not involved and insulin basal and bolus administration is fully automatic. Artificial pancreas (AP) algorithm software 120 resides within processor 48 (dotted line) and controls actuation module 24 operation according to patients glucose levels that are continuously transmitted from CGM 300 to processor 48 via transceiver 46. Insulin administration data, alerts and alarms may be transmitted to controller 200 or smartphone 500 providing the patient with ongoing data on pump 6 operation and glucose levels.

Figure 38:
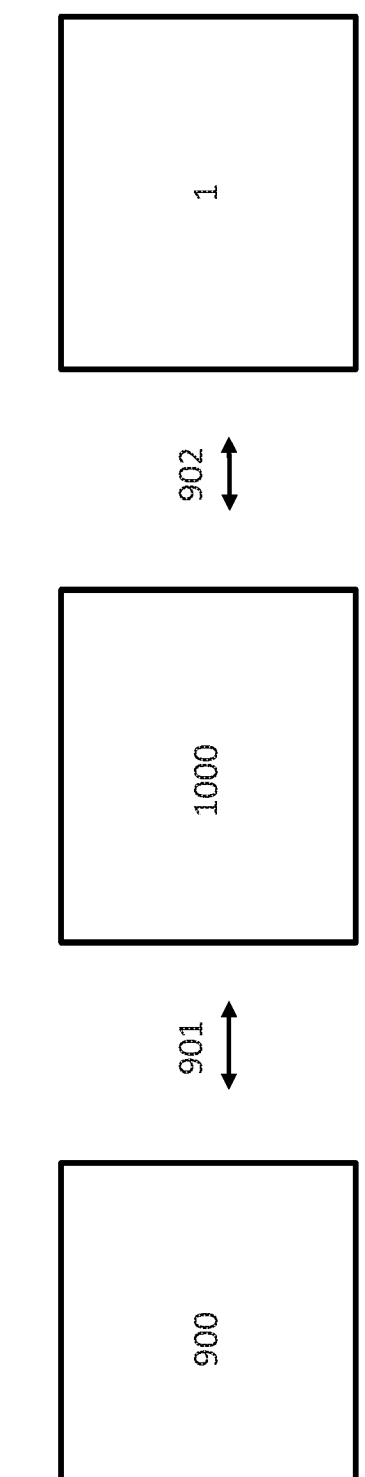
FIG. 38 shows a block diagram of insulin management system, according to some embodiments.

With reference to FIGS. 38, in some embodiments, a block diagram of an embodiment of insulin management system 100 is shown. Insulin management system 100 comprises web server 900, bridge device 1000, and insulin patch pump 1. There is a two-way data communication channel 901 between server 900 and bridge 1000, and a two-way data communication channel 902 between bridge 1000 and pump 1.

Figures 39A, 39B, 39C, 39D:
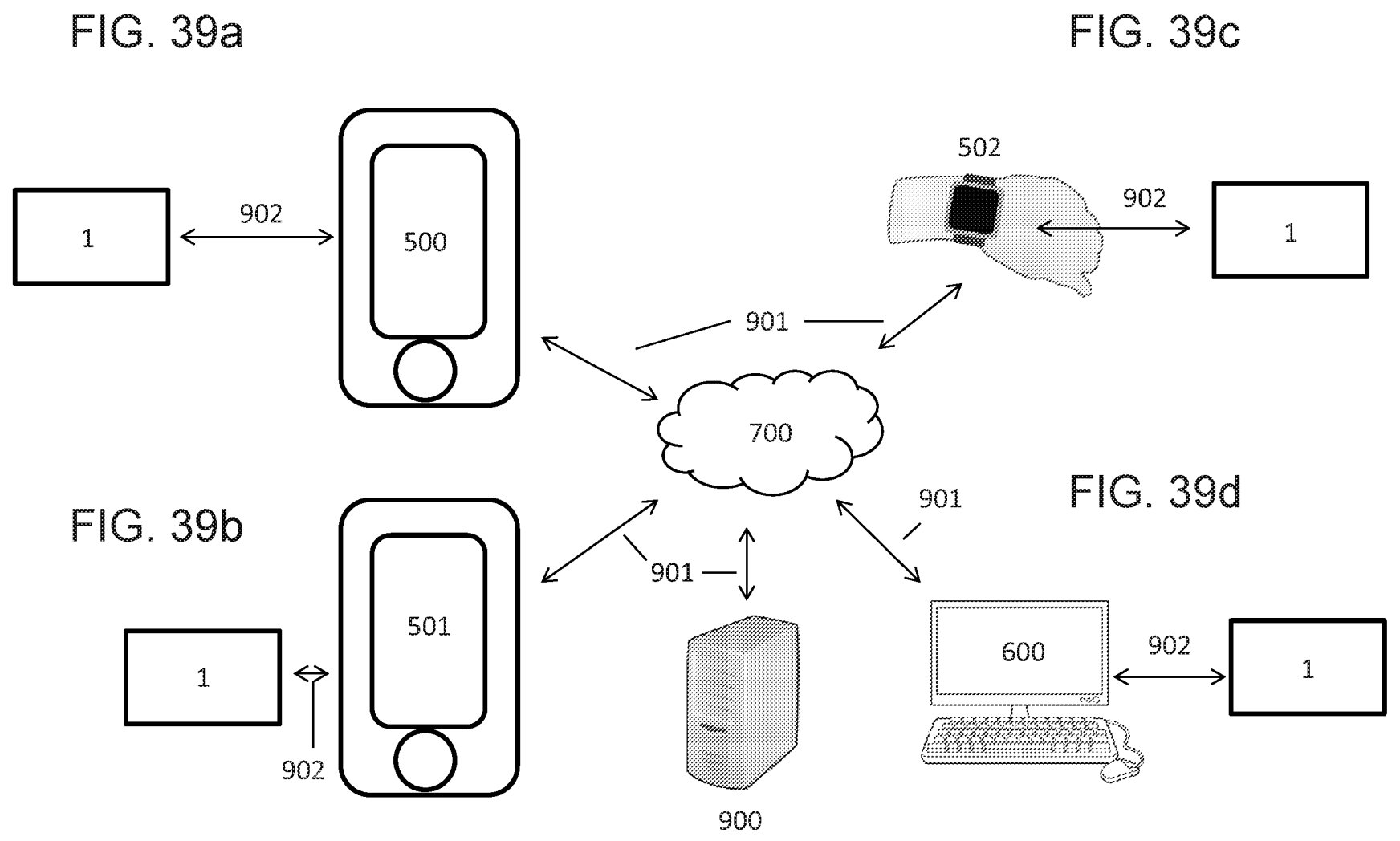

With reference to FIGS. 39A-B, in some embodiments, examples of bridge devices (a-d) are shown. Bridge device 1000 may be any consumer electronic device that includes a user interface and RF transceiver. For example, bridge device 1000 may be a smartphone 500, 501 (39*a-b*), smart watch 502 (39*c*) (i.e. iWatch, Pebble watch), PC 600 (39*d*), and tablet (not shown). Communication 902 between bridge devices 1000 and pump 1 may be RF communication (FIG. 39*a, c, d*) or near field communication (NFC) (FIG. 39*b*). Communication 901 between server 900 and bridge device 1000 through cloud 700 may be cellular or RF (i.e. Wi-Fi).

Figure 40:
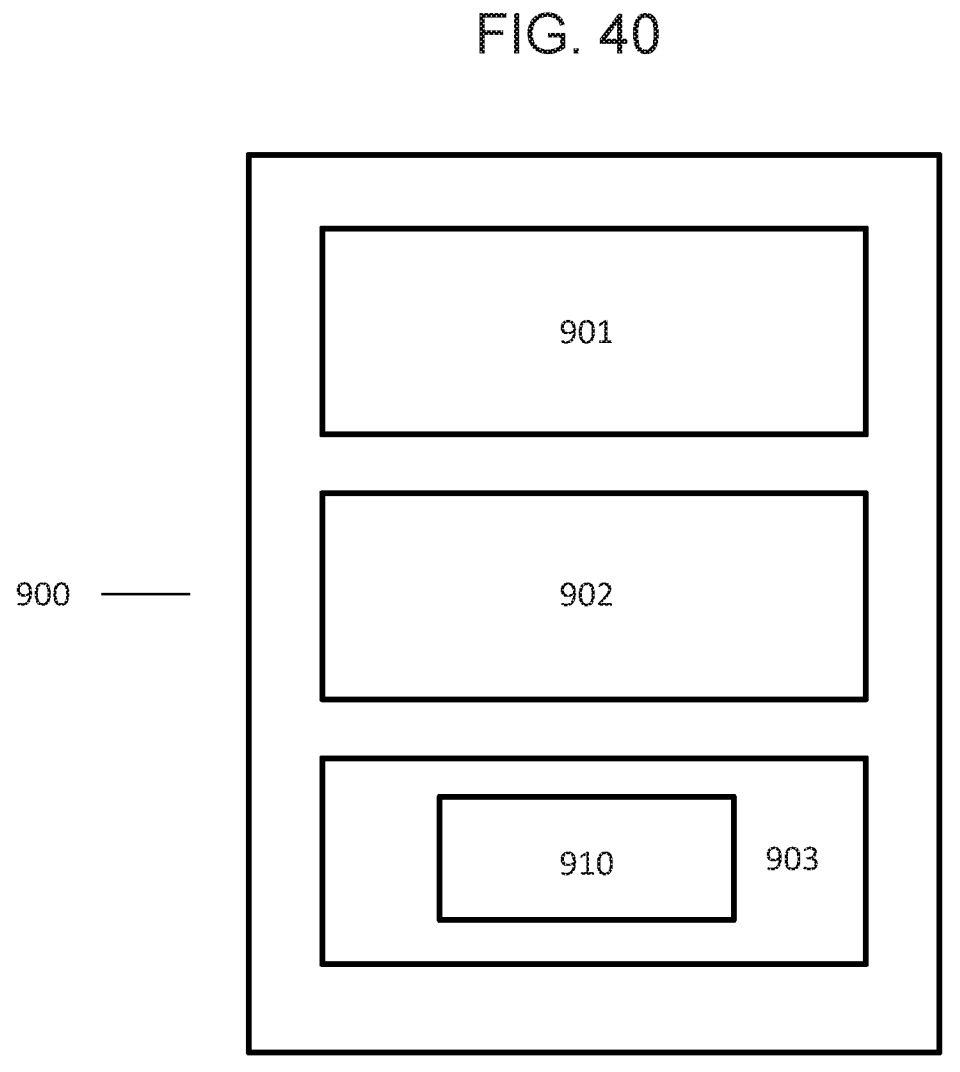

With reference to FIG. 40, in some embodiments, a schematic diagram of server 900 is shown. Server 900 comprises CPU 901, data communication module 902, and memory 903. Memory 903 may store patient data 910, such as the patient's insulin management programs and records and a unique identity for pump 6.

Figure 41:
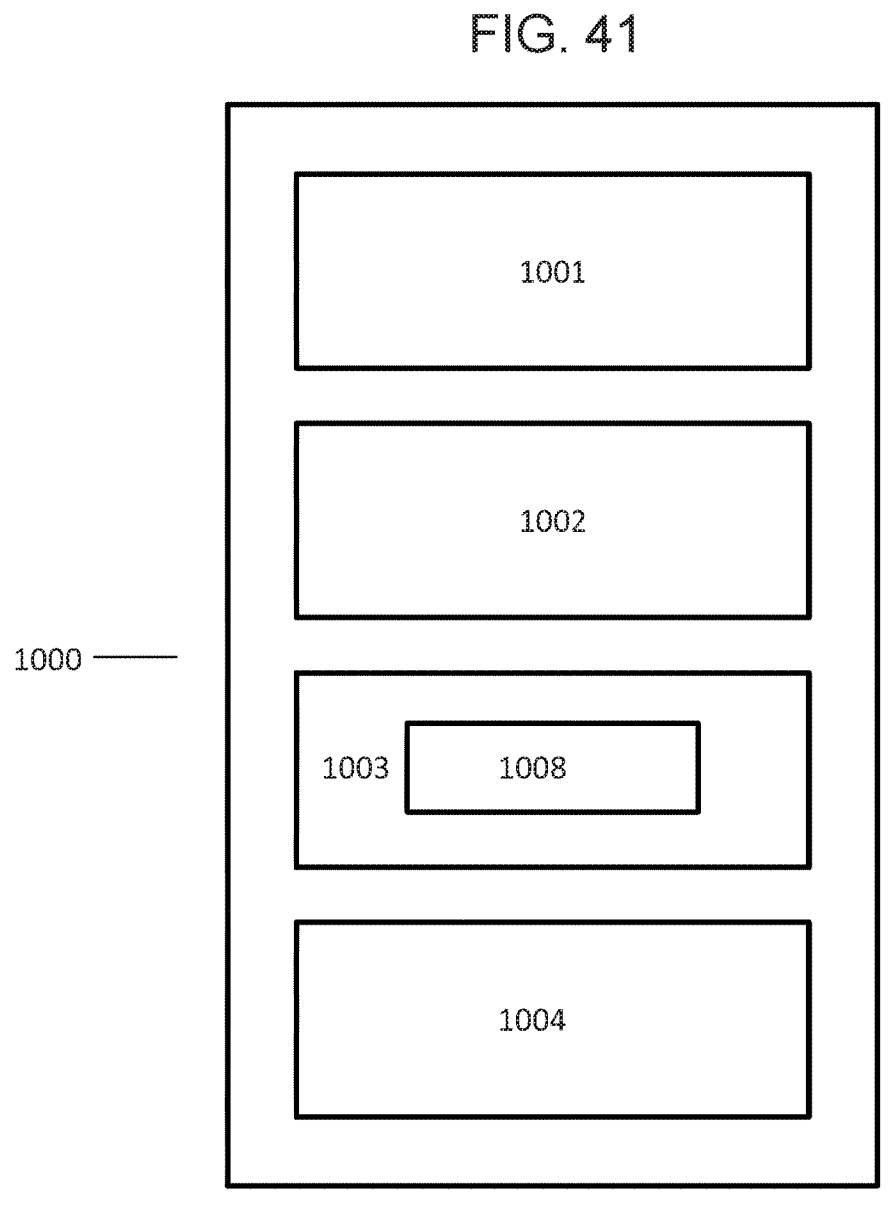

With reference to FIG. 41, in some embodiments, a schematic diagram of bridge device 1000 is shown. Bridge 1000 comprises a CPU 1001, a data communication module 1002, a memory 1003, and a man-machine interface 1004. Memory 1003 stores pump identification, patient data, insulin delivery instructions, and software for pump control. A software application 1008, which may be downloadable from an application store such Apple's AppStore or Google's GooglePlay, resides in memory 1003. Software application 1008 is configured to endow the bridge 1000 with the ability to instruct and control pump 1 and communicate information between pump 1 and server 900. In order to make insulin management system 1 operable, the user performs the following steps:

If software application 1008 is not already on bridge 1000 then the user downloads application 1008 to bridge 1000. The application may verify its own integrity once on bridge 1000.

Application 1008 on bridge 1000 requests user authentication such as a password, a finger print or other biometric data.

The user authentication information provided to bridge 1000 by the user is communicated via channel 901 to server 900 and verified there against the user's ID, which is part of patient data 910.

If authentication is successful then the server sends some or all of the user's data 910 (including pump identification information) to bridge 1000.

Bridge 1000 and pump 1 pair.

Optionally, the user is notified that bridge 1000 and pump 1 have paired.

Optionally, the user authorizes the bridge 1000 to send the user data to pump 1.

Pump 1 stores user data 910. Optionally, pump 1 verifies user data 910 and decrypts the data if it is signed and/or encrypted.

Pump 1 is ready to deliver insulin according to user's data 910.

Note that insulin management system 100 allows the user to endow various bridge devices with controller capabilities easily, securely and swiftly. Thus, if for example, a given bridge device 1000 becomes inoperable (battery is depleted, bridge device is forgotten or lost, and so forth), then another readily available bridge device can be made operable conveniently and quickly by downloading software application 1008 and performing the authentication process vis a vis the server. When using software application 1008 on bridge 1000, user may provide the pump with insulin delivery instruction:

User provides instruction to bridge 1000 via man machine interface 1004.

Bridge 1000 communicates instruction to pump 1 via channel 902.

User is notified that pump 1 received the instruction.

Bridge 1000 records instructions on server 900 as early as practicable in order to make them available to a new bridge device should one be required.

Additional embodiments of the subject application include a portable fluid infusion device, comprising: a first reservoir; a second reservoir having a plunger; an exit port; a first conduit configured to allow a unidirectional fluid communication from the first reservoir to the second reservoir; a second conduit configured to allow a unidirectional fluid communication from the second reservoir to the exit port; wherein displacement of the plunger in a first direction is designed to cause flow of fluid from the first reservoir to the second reservoir via the first conduit, and displacement of the plunger opposite to the first direction is designed to cause flow of fluid from the second reservoir to the exit port via the second conduit. In some embodiments, the first reservoir comprises a filling port for receiving fluid into the first reservoir, and/or a prefilled replaceable reservoir. Further, the first reservoir comprises a second plunger configured to transition between two ends of the first reservoir in the first direction and/or in a direction opposite to the first direction, wherein the advancement of the second plunger in the direction opposite to the first direction is configured to cause flow of fluid from the first reservoir to the second reservoir.

In some embodiments, the portable fluid infusion device comprises an electronic module and an actuation module for operating the displacement of the plunger in the first direction and/or opposite to the first direction. In some embodiments, the electronics module comprises a power source, a processor, a transceiver, a buzzer, and/or a sensor, wherein the power source comprises a replaceable modular battery or a rechargeable battery. Further, the sensor can include one or more of: a motion sensor, a power source level sensor, air bubble sensor, revolution sensor, occlusion sensor, reservoir level sensor, and/or plunger position sensor. In some embodiments, the first reservoir may comprise a first reservoir plunger, and the reservoir level sensor may comprise a first reservoir sensor configured to detect a position of the first reservoir plunger within the first reservoir so as to determine amount of remaining fluid in the first reservoir. In some embodiments, the reservoir level sensor may comprise a second reservoir sensor configured to detect a position of the plunger of the second reservoir so as to determine amount of remaining fluid in the second reservoir. Further, the air bubble sensor may detect air bubbles travelling through the second conduit.

In some embodiments, the actuation module may comprise an actuator and a rod, the rod configured to operably couple to the plunger to drive the displacement of the plunger in the first and/or opposite to the first directions. In some embodiments, the actuation module comprises an actuator and a rod, the rod configured to operably couple to the plunger to drive the displacement of the plunger in the first and/or opposite to the first directions. Further, the portable fluid infusion device may comprise a rod coupling means coupled to the rod and a plunger coupling means coupled to the plunger, wherein a connection between the rod coupling means and the plunger coupling means allows the rod to operably couple to the plunger, wherein the connection between the rod coupling means and the plunger coupling means is mechanical and/or magnetic. In some embodiments, a distal end of the first reservoir may align with or extend beyond distal end of the rod upon maximum displacement of the plunger in the first direction.

In some embodiments, a portable fluid infusion device comprises a first reservoir; a second reservoir having a plunger, a first opening and a second opening; an exit port; a first conduit for establishing fluid communication between the first reservoir and the second reservoir upon alignment of an end of the first conduit with the first opening; and a second conduit for establishing fluid communication between the second opening and the exit port upon alignment of an end of the second conduit with the second opening; wherein displacement of the plunger in a first direction is configured to align the end of the first conduit with the first opening and displacement of the plunger in a direction opposite to the first direction is configured to align the end of the second conduit with the second opening. In some embodiments, the first reservoir comprises a filling port for receiving fluid into the first reservoir, and/or the first reservoir comprises a prefilled replaceable reservoir. In some embodiments, the first reservoir comprises a second plunger configured to transition between two ends of the first reservoir in the first direction and/or in the direction opposite to the first direction, wherein the advancement of the second plunger in the direction opposite to the first direction is configured to cause flow of fluid from the first reservoir to the second reservoir.

Further, in some embodiments, the portable fluid infusion device comprises an electronic module and an actuation module for operating the displacement of the plunger in the first and/or opposite to the first directions, wherein the electronics module comprises a power source, a processor, a transceiver, a buzzer, and/or a sensor. In some embodiments, the sensor may include one or more of a motion sensor, a power source level sensor, air bubble sensor, revolution sensor, occlusion sensor, reservoir level sensor, second reservoir motion sensor, second reservoir position sensor, and/or plunger position sensor. In some embodiments, the actuation module comprises an actuator and a rod, the rod configured to operably couple to the plunger to drive the displacement of the plunger and/or the second reservoir. Further, the actuation module may comprise a rod coupling means coupled to the rod and a plunger coupling means coupled to the plunger, wherein a connection between the rod coupling means and the plunger coupling means allows the rod to operably couple to the plunger, wherein the connection between the rod coupling means and the plunger coupling means is mechanical and/or magnetic. In some embodiments of the portable fluid infusion device, the distal end of the first reservoir aligns with or extends beyond distal end of the rod upon maximum displacement of the plunger in the first direction.

In some embodiments, a disposable skin interface for a portable fluid infusion device includes a disposable part (DP) containing a first reservoir and a second reservoir having a plunger, and a reusable part (RP) containing at least two compartments for receiving the first reservoir and the second reservoir separately. The disposable skin interface comprises a cannula; a removable inserter for inserting the cannula into through a surface of a body; and a cradle for providing support to the cannula and the inserter, said cradle configured to establish reversible connection with the portable fluid infusion device upon removal of the inserter from the cradle so as to allow flow of fluid from the second reservoir of the portable fluid infusion device into the body upon displacement of the plunger. In some embodiments, the removable inserter further comprises a skin penetrating member connected to the inserter for aiding in the insertion of the cannula through the surface of the body, wherein the skin penetrating member is configured to retract into the removable inserter leaving the cannula embedded in the surface of the body. Further, the cradle can be reversibly connected to the portable fluid infusion device via magnetic and/or mechanical connection between the cradle and the portable fluid infusion device, wherein the magnetic connection between the cradle and the portable fluid infusion device comprises a magnetic connection between the cradle and one or more of: a ferromagnetic material in a shell of the RP, a magnet in the RP, an electromagnet in the RP and a magnetic metal in the DP. In some embodiments, the mechanical connection between the cradle and the portable fluid infusion device may comprise a snap mechanism. The cradle may comprise a window for allowing visual access to site of cannula insertion on the surface of the body.

In some embodiments, a diabetes management system comprises at least one of a blood glucose monitor (BGM) and a continuous glucose monitor (CGM), wherein the BGM is configured to measure a blood glucose level of a body and transmit the blood glucose level to a processor; and the CGM is configured to detect data on blood glucose level trends of a body and transmit the blood glucose level trends data to the processor. Further, the management system includes a portable insulin infusion device, communicatively coupled to the controller and/or the smartphone, configured to deliver an amount of insulin to the body upon receiving instructions from the processor. In some embodiments, the processor may be communicatively coupled to at least one of a blood glucose monitor (BGM) and a continuous glucose monitor (CGM), may be configured to: determine the amount of insulin to be delivered to the body based on at least the transmitted blood glucose level, the transmitted blood glucose level trends data, and/or health data of the body from an external device; and transmit the instructions to the portable insulin infusion device indicating the amount of insulin to be delivered to the body. In some embodiments, the system operates in a closed loop mode wherein the processor is a processor in the insulin infusion device, and/or in an open loop mode wherein the processor is a processor in the external device. Further, the portable insulin infusion device may comprise sensors including at least one of a motion sensor, a power source level sensor, air bubble sensor, revolution sensor, occlusion sensor, reservoir level sensor, and plunger position sensor; and the portable insulin infusion device may transmit data measured by the sensors to the controller and/or the smartphone.

In some embodiments, a method for delivering fluid into a body comprises the steps of establishing contact to a surface of the body via a disposable skin interface configured to insert a cannula into the body; providing a portable fluid infusion device comprising a disposable part (DP) containing a first reservoir having the fluid and a second reservoir having a plunger, and a reusable part (RP) containing an actuation module; and operating the actuation module to: displace the plunger in a first direction so as to cause the fluid to be flow from the first reservoir to the second reservoir; displace the plunger in an opposite direction so as to cause that fluid to flow from the second reservoir to an exit port of the portable fluid infusion device; and establish fluid communication between the exit port of the portable fluid infusion device and the cannula inserted into the body so as to allow the entry of the fluid into the body.

In some embodiments, a diabetes management system, comprises a portable fluid infusion device configured to deliver an amount of fluid into a body of a patient upon receiving fluid infusion instructions; a bridge device; and a server, communicatively coupled to the portable fluid infusion device and the bridge device, configured to: provide the bridge device with applications for controlling operations of the portable fluid infusion device; and authenticate access authorization for a user of the bridge device accessing the applications. In some embodiments, the bridge device, communicatively coupled to the portable fluid infusion device, is configured to: receive patient data from the portable fluid infusion device and/or the user of the bridge device; determine the amount of fluid to be delivered to the body based on at least the received patient data; and transmit the fluid infusion instructions to the portable fluid infusion device indicating the amount of fluid to be delivered to the body.

In some embodiments, a method for operating a fluid infusion device comprises the steps of receiving, from an occlusion sensor in a portable fluid infusion device, a warning indicating occurrence of occlusion, the portable fluid infusion device comprising a disposable part (DP) having an exit port, and a reusable part (RP) comprising an actuation module and the occlusion sensor; operating the actuation module so as to determine source of the occlusion; determining a presence of flow of fluid exiting the exit port as a result of the operation of the actuation module; and replacing the DP if the presence of flow of fluid exiting the exit port is not detected. The method further comprises the steps of replacing a cannula if the presence of flow of fluid exiting the exit port is detected, wherein a disposable skin interface comprising the cannula provides an interface allowing the portable fluid infusion device to infuse fluid into a body, and wherein the occlusion sensor determines the occurrence of occlusion based on comparison of torque at the actuation module when a motor of the actuation module is rotated in a clockwise and an anticlockwise directions.

In some embodiments, a method for removing air bubbles from a fluid infusion device comprises the step of: orienting a portable fluid infusion device so as to cause migration of air bubbles inside a reservoir having a plunger towards an opening at an end of the reservoir, wherein the reservoir comprises a plunger; and the portable fluid infusion device comprises: a disposable part (DP) having the reservoir and an exit port, and a reusable part (RP) comprising an actuation module. The method further comprises the step of operating the actuation module so as to cause an oscillation of the plunger until at least a substantial amount of the air bubbles are discharged through the exit port, wherein the plunger is oscillated at a pre-programmed rate. In some embodiments, the method also comprises the step of determining a presence of the air bubbles via an air bubble sensor detecting travel of the air bubbles through a conduit leading to the exit port, wherein the air bubble sensor is operated by piezoelectric ultrasonic transducers, and the conduit is transparent, and the air bubble sensor comprises an optic sensor detecting light transmission through the transparent conduit.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. At least some of the disclosed embodiments may be distinguishable from the prior art by expressly lacking one and/or another feature(s) taught by the prior art. Thus, claims directed to such embodiments may be distinguished from the prior art by including negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

At least some of the embodiments disclosed above, in particular at least some of the methods/processes disclosed, may be realized in circuitry, computer hardware, firmware, software, and combinations thereof (e.g., a computer system). Such computing systems, may include PCs (which may include one or more peripherals well known in the art), smartphones, specifically designed medical apparatuses/devices and/or other mobile/portable apparatuses/devices. In some embodiments, the computer systems are configured to include clients and servers. A client and server are generally remote from each other and typically interact through a communication network (e.g., VPN, Internet). The relationship of client and server arises by virtue of computer programs running on the respective computers and having a client-server relationship to each other.

Some embodiments of the disclosure (e.g., methods and processes disclosed above) may be embodied in a computer program(s)/instructions executable and/or interpretable on a processor, which may be coupled to other devices (e.g., input devices, and output devices/display) which communicate via wireless or wired connect (for example).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A portable infusion device configured for delivering an analyte into tissue comprising:
   a disposable part (DP);
   a reusable part (RP) including an actuation module and an electronics module;
   a first reservoir including a first plunger;
   a second reservoir comprising a doser reservoir and including a doser plunger;
   and
   an exit port,
   wherein the electronics module together with the actuation module are configured for operating the displacement of the doser plunger in a first direction and/or opposite to the first direction so as to cause oscillation of the doser plunger to discharge a substantial amount of air bubbles within the doser reservoir through the exit port.

2. The portable infusion device according to claim 1, wherein the doser plunger is oscillated at a pre-programmed rate.

3. The portable infusion device of claim 1, further comprising a conduit leading to the exit port and an air bubble sensor configured to detect travel of the air bubbles through the conduit.

4. The portable infusion device of claim 3, wherein the air bubble sensor is operated by one or more piezoelectric ultrasonic transducers.

5. The portable infusion device of claim 3, wherein the conduit is transparent, and the air bubble sensor comprises an optic sensor detecting light transmission through the transparent conduit.

6. The portable infusion device of claim 5, further comprising one or more additional sensors.

7. The device of claim 6, wherein:
   the one or more additional sensors include a reservoir level sensor, and/or a plunger position sensor, and
   the reservoir level sensor is configured to detect a position of a plunger so as to determine an amount of remaining fluid in a reservoir.

8. The portable infusion device of claim 1, wherein the first reservoir includes a filling port for receiving fluid therein.

9. The portable infusion device of claim 1, wherein the first reservoir is configured as a prefilled replaceable reservoir.

10. The portable infusion device of claim 1, wherein the electronics module includes a processor, a power source, a transceiver, and/or a buzzer.

11. The portable infusion device of claim 10, wherein the power source comprises a replaceable modular battery.

12. A portable infusion device configured for delivering an analyte into tissue comprising:
   a disposable part (DP);
   a reusable part (RP) including an actuation module;
   a first reservoir including a first plunger;
   a second reservoir comprising a doser reservoir and including a doser plunger;
   and
   an exit port,
   wherein:
      the actuation module further comprises a rod and is operational so as to cause oscillation of the doser plunger to discharge a substantial amount of air bubbles through the exit port, and
      the rod is configured to operably couple to the doser plunger to drive the displacement of the doser plunger in a first direction and/or opposite to the first direction.

13. The portable infusion device of claim 12, further comprising a rod coupling means coupled to the rod and a plunger coupling means coupled to the doser plunger, wherein a connection between the rod coupling means and the plunger coupling means allows the rod to operably couple to the doser plunger.

14. The portable infusion device of claim 13, wherein the connection between the rod coupling means and the plunger coupling means is mechanical and/or magnetic.

* * * * *